(12) United States Patent
Molloy et al.

(10) Patent No.: US 7,074,400 B1
(45) Date of Patent: Jul. 11, 2006

(54) REGULATORY CONSTRUCTS COMPRISING INTRON 3 OF PROSTATE SPECIFIC MEMBRANE ANTIGEN GENE

(75) Inventors: Peter Laurence Molloy, Chatswood (AU); Fujiko Watt, Rozelle (AU)

(73) Assignee: The Commonwealth of Australia, Campbell (AU)

( * ) Notice: Subject to any disclaimer, the term of this patent is extended or adjusted under 35 U.S.C. 154(b) by 0 days.

(21) Appl. No.: 09/914,651

(22) PCT Filed: Mar. 1, 2000

(86) PCT No.: PCT/AU00/00143

§ 371 (c)(1),
(2), (4) Date: Dec. 27, 2001

(87) PCT Pub. No.: WO00/52156

PCT Pub. Date: Sep. 9, 2000

(30) Foreign Application Priority Data

Mar. 1, 1999 (AU) .................................. PP8956
Jan. 25, 2000 (AU) .................................. PQ5268

(51) Int. Cl.
*A61K 48/00* (2006.01)
*A61K 31/711* (2006.01)
*C07H 21/04* (2006.01)
*C12N 15/861* (2006.01)
*C12N 15/63* (2006.01)

(52) U.S. Cl. ................... 424/93.2; 424/93.1; 424/93.6; 435/320.1; 435/69.1; 536/23.1; 536/23.5; 536/24.1

(58) Field of Classification Search ............... 435/69.1, 435/6, 29, 320.1, 235.1, 440, 455, 471, 325, 435/252.3; 536/23.1, 24.1
See application file for complete search history.

(56) References Cited

U.S. PATENT DOCUMENTS 5,538,866 A   7/1996   Israeli et al.

FOREIGN PATENT DOCUMENTS

AU      51725 96        9/1996
WO      WO 98 33903 A   8/1998

OTHER PUBLICATIONS

Orkin, et al. Report and Recommendations of the Panel to Assess the NIH Investment in Research on Gene Therapy, The National Institutes of Health, Dec. 7, 1995.*
Verma, et al. Nature, Sep. 1997, vol. 389, pp. 239-242.*
Anderson, French W. Nature, Apr. 1998, vol. 392, pp. 25-30.*
Palù et al. J. Biotechnol, 1999, vol. 68, pp. 1-13.*
Luo et al, Nature Biotechnology, 2000, vol. 18, pp. 33-37.*
Check, Erica. Nature, Feb. 2003, vol. 421, p. 678.*
"Mapping, genomic organization and promoter analysis of the human prostate-specific membrane antigen gene", O'Keefe et al., Biochemica et Biophysica Acta 1443, (1998), pp 113-127.
Genbank Accession No. AF007544.
"Detailed genetic mapping around a putative prostate-specific membrane antigen locus on guman chromosome 11p11.2", Maraj et al., Cytogenetics and Cell Genetics, Vo. 81 (1998). pp. 3-9.
"Cloning and Characterization of the Prostate-Specific Membrane Antigen Promoter", Good. D. et al., Journal of Cellular Biochemistry 74(3), pp. 395-405, Sep. 1999.
"Prostate-Specific Membrane Antigen", W. R. Fair et al., Prostate, Wiley-Liss, New York, NY, US, vol. 32, No. 2, 1997, pp. 140-148, XP000870112. ISSN: 0270-4137.

* cited by examiner

*Primary Examiner*—David Guzo
(74) *Attorney, Agent, or Firm*—McDermott Will & Emery LLP

(57) ABSTRACT

The invention provides regulatory constructs comprising intron 3 of the prostate specific membrane antigen gene (PSMA). An isolated nucleic acid molecule encoding the partial sequence of intron 3 of PSMA, a vector and a recombinant expression cassette are disclosed. The invention also provides a method of directing expression of a coding sequence in a prostate cell, a bladder cell, a breast cell and a vascular endothelial cell using the said constructs. This invention further provides a method of treatment of cancer using the said constructs.

48 Claims, 14 Drawing Sheets

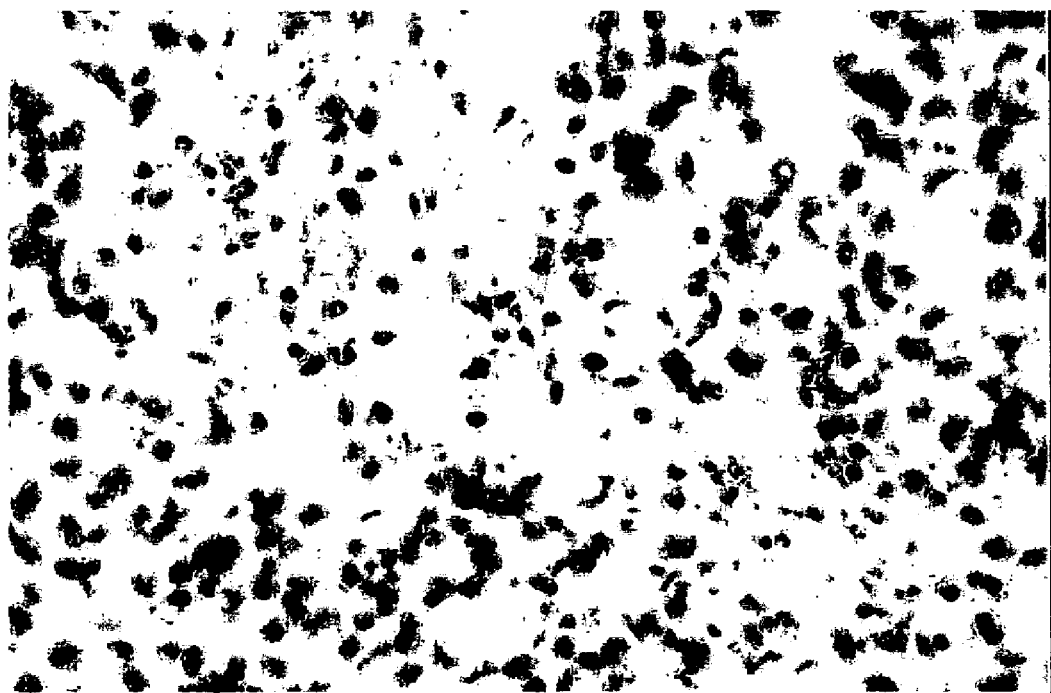
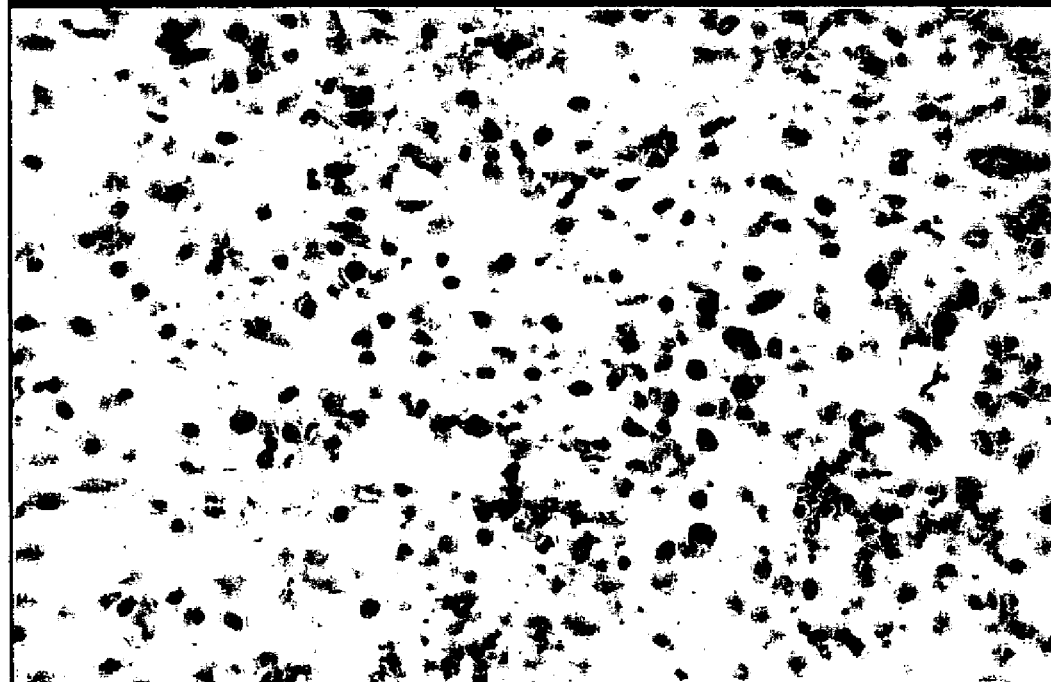
Figure 5

Sequence of 331 base pair core region of the PSME

14760
AATTATTTTTCCTTTAACCTTTCAAACTCAAGGAAAACCAGTTGGCCTTGACTCTGTTT
14820
GTGGAAAATTTTAAACTACTGGTTTAATTTCTTTATTGGTTGTAATATGACTATTTTACG
14880
TCATATAACAATTTTTATTGTTTGTTAAATGACTTTATTGTTTGT<u>CATATGA</u>TAATTTTA
14940
TGTCATAGAACAATTTTTATTGCTTGATATATGACTTTATTGTTATATGGCTATACAACT
15000
AGATTTTTTGTTGTTTTGACCGAGTCTTACTCTGTCACCCAGGCTGGAGTGTAATGGC
15060
ATGGTCTCAGCTCACTGCAACCTCCGCCTCCCGGG

The NdeI site 168 base pairs from the start of the core enhancer is underlined

Figure 11 (SEQ ID NO.1)

SEQUENCE LISTING

```
<160> NUMBER OF SEQ ID NOS: 2

<210> SEQ ID NO 1
<211> LENGTH: 335
<212> TYPE: DNA
<213> ORGANISM: Homo sapiens

<400> SEQUENCE: 1
aattattttt tcctttaacc tttcaaactc aaggaaaacc agttggcctt gactctgttt      60
gtggaaaatt ttaaactact ggtttaattt ctttattggt tgtaatatga ctattttacg     120
tcatataaca atttttattg tttgttaaat gactttattg tttgtcatat gataattta     180 tgtcatagaa caatttttat tgcttgatat atgactttat tgttatatgg ctatacaact    240 agatttttt gttgttttg accgagtctt actctgtcac ccaggctgga gtgtaatggc      300
atggtctcag ctcactgcaa cctccgcctc ccggg                                335

<210> SEQ ID NO 2
<211> LENGTH: 93525
```

-continued

```
<212> TYPE: DNA
<213> ORGANISM: Homo sapiens
<220> FEATURE:
<221> NAME/KEY: misc_feature
<222> LOCATION: (81824)..(81824)
<223> OTHER INFORMATION: n is a, c, g, or t
<220> FEATURE:
<221> NAME/KEY: misc_feature
<222> LOCATION: (88177)..(88177)
<223> OTHER INFORMATION: n is a, c, g, or t
<220> FEATURE:
<221> NAME/KEY: misc_feature
<222> LOCATION: (88179)..(88179)
<223> OTHER INFORMATION: n is a, c, g, or t
<220> FEATURE:
<221> NAME/KEY: misc_feature
<222> LOCATION: (88185)..(88185)
<223> OTHER INFORMATION: n is a, c, g, or t
<220> FEATURE:
<221> NAME/KEY: misc_feature
<222> LOCATION: (88188)..(88189)
<223> OTHER INFORMATION: n is a, c, g, or t

<400> SEQUENCE: 2
```

| | | | | | |
|---|---|---|---|---|---|
| aagggtgctc | cttaggctga | atgcttgcag | acaggatgct | tggttacaga | tgggctgtga     60 |
| ctcgagtgga | gttttataag | ggtgctcctt | aggctgaatg | cttgcagaca | ggatgcttgg    120 |
| ttacagatgg | gctgtgagct | gggtgcttgt | aagaggatgc | ttgggtgcta | agtgagccat    180 |
| ttgcagttga | ccctattctt | ggaacattca | ttccctcta | ccctgtttc | tgttcctgcc    240 |
| agctaagccc | attttcatt | tttcttttaa | ctccttagcg | ctccgcaaaa | cttaatcaat    300 |
| ttctttaaac | ctcagttttc | ttatctgtaa | aggtaaata | ataatacagg | gtgcaacaga    360 |
| aaaatctagt | gtggtttaca | taatcacctg | ttagagattt | taaattattt | caggataagt    420 |
| catgataatt | aaatgaaata | atgcacataa | agcacatagt | gtggtgtcct | ccatatagaa    480 |
| aatgctcagt | atattggtta | ttaactactt | gttgaaggtt | tatcttctcc | actaaactgt    540 |
| aagttccaca | agccttacaa | tatgtgacag | atattcattc | attgtctgaa | ttcttcaaat    600 |
| acatcctctt | caccatagcg | tcttattaat | tgaattatta | attgaataaa | ttctattgtt    660 |
| caaaatcac | tttatatttt | aactgaaatt | tgcttactta | taatcacatc | taaccttcaa    720 |
| agaaaacaca | ttaaccaact | gtactgggta | atgttactgg | gtgatcccac | gttttacaaa    780 |
| tgagaagata | tattctggta | agttgaatac | ttagcaccca | ggggtaatca | gcttggacag    840 |
| gaccaggtcc | aaagactgtt | aagagtcttc | tgactccaaa | ctcagtgctc | cctccagtgc    900 |
| cacaagcaaa | ctccataaag | gtatcctgtg | ctgaatagag | actgtagagt | ggtacaaagt    960 |
| aagacagaca | ttatattaag | tcttagcttt | gtgacttcga | atgacttacc | taatctagct   1020 |
| aaatttcagt | tttaccatgt | gtaaatcagg | aagagtaata | gaacaaacct | tgaagggtcc   1080 |
| caatggtgat | taaatgaggt | gatgtacata | acatgcatca | ctcataataa | gtgctcttta   1140 |
| aatattagtc | actattatta | gccatctctg | attagatttg | acaataggaa | cattaggaaa   1200 |
| gatatagtac | attcaggatt | tgttagaaa | gagatgaaga | aattccttc | cttcctgccc   1260 |
| taggtcatct | aggagttgtc | atggttcatt | gttgacaaat | taatttttccc | aaattttttca   1320 |
| ctttgctcag | aaagtctaca | tcgaagcacc | caagactgta | caatctagtc | catcttttc   1380 |
| cacttaactc | atactgtgct | ctcccttct | caaagcaaac | tgtttgctat | tccttgaata   1440 |
| cactctgagt | tttctgcctt | tgcctactca | gctggcccat | ggcccctaat | gtttcttctc   1500 |
| atctccactg | ggtcaaatcc | tacctgtacc | ttatggttct | gttaaaagca | gtgcttccat   1560 |
| aaagtactcc | tagcaaatgc | acggcctctc | tcacggatta | taagaacaca | gtttatttta   1620 |

-continued

```
taaagcatgt agctattctc tccctcgaaa tacgattatt attattaaga atttatagca    1680
gggatataat tttgtatgat gattcttctg gttaatccaa ccaagattga ttttatatct    1740
attacgtaag acagtagcca gacatagccg ggatatgaaa ataaagtctc tgccttcaac    1800
aagttccagt attctttttct ttcctcccct cccctcccct ccttcccct cccttcctt    1860
cccctttccct tccttccctt tcctttcttga gggagtctca ctctgtcacc aggctccagt    1920
gcagtggcgc tatcttggct gactgcaacc tccgcctccc cggttcaagc gattctcctg    1980
cctcagcctc ctgagtagct gggactacag gagcccgcca ccacgcccag ctaatttttg    2040
tatttttagt agagatgggg tttcaccatg ttggccagga tggtctcgat ttctcgactt    2100
cgtgatccgc ctgtctgggc ctcccaaagt gctgggatta caggcgtgag ccaccacgcc    2160
cggctttaaa aaatggtttt gtaatgtaag tggaggataa taccctacat gtttattaat    2220
aacaataata ttctttagga aaagggcgc ggtggtgatt tacactgatg acaagcattc    2280
ccgactatgg aaaaaaagcg cagcttttc tgctctgctt ttattcagta gagtattgta    2340
gagattgtat agaatttcag agttgaataa aagttcctca taattatagg agtggagaga    2400
ggagagtctc tttcttcctt tcattttat atttaagcaa gagctggaca ttttccaaga    2460
aagttttttt tttttaaggc gcctctcaaa aggggccgga tttccttctc ctggaggcag    2520
atgttgcctc tctctctcgc tcggattggt tcagtgcact ctagaaacac tgctgtggtg    2580
gagaaactgg accccaggtc tggagcgaat ccagcctgc agggctgata agcgaggcat    2640
tagtgagatt gagagagact ttaccccgcc gtggtggttg gagggcgcgc agtagagcag    2700
cagcacaggc gcgggtcccg ggaggccggc tctgctcgcg ccgagatgtg gaatctcctt    2760
cacgaaaccg actcggctgt ggccaccgcg cgccgcccgc gctggctgtg cgctggggcg    2820
ctggtgctgg cgggtggctt ctttctcctc ggcttcctct tcggtagggg gcgcctcgc    2880
ggagcaaacc tcggagtctt tccccgtggt gccgcggtgc tggactcgcg ggtcagctgc    2940
cgagtgggat cctgttgctg gtcttcccca ggggcggcga ttagggtcgg ggtaatgtgg    3000
ggtgagcacc cctcgagtta ggaggagggt agctgggaac ggtgcagggc tgagttctcg    3060
acaagctgct ggtaggacag tcactcaggt tgagggtaga actgagagaa cctgaaactg    3120
ggcgtaggaa ggttccaagt gctggagccc tgcaagacag aggaagtttt ttttttgctt    3180
ttgttttgtt ttgtttttgtt ttgtttttgtt ttgtttgttt gtttgttttt ttacctctct    3240
gtgcattctt tcttccttgg aagtaacaga ggcaagcttg ggaactgtgt gaaccaggtc    3300
agcaatctgg acaggtcttt accagcgggt cttttgctgt ttttcctggg tactgatttg    3360
cagacttgat ccaactttct aagaaaagca gaaccacaca ggcaagctca gactctttta    3420
ttaaattcca gttttgactt tgccacttct tagtggcctt gaacaagtta ccgagtccct    3480
ctcagcgtta gttaccctat tttatgatga ggataatatt atctgcaaat tattggtaat    3540
agtaaataat atagcatgta aatctcctag cacagtactg ggattttcgc cactttattt    3600
cttcttttac caagatactc ctcattggac tttaatacac aggactagtc taaggtatca    3660
ccaggtagtc cactcctgct cggaattctt gaccctcttt cgggatttag aagaataggg    3720
catggaccag atgggtttaa acaaattcaa tatcttccac tagcttcacc ttgggttgt    3780
taaaagattt ttgaaccaca cactgtgctc ataacaatct tcatctctta aaaggatttt    3840
attcttcctg gtattgccct cactctcatc cctgtattcc gtgctcagtg gctgacacag    3900
aagagttctt tattgatgtc cgcccccac ccactaggat tctctgctct ccccttcccc    3960
ctacaggcct ccatcctctt catcctgttc attttcaga tctcagttca agcatctcgt    4020
```

```
cctcagtgtg tgtgtttcctg atccctcact ctaatccaag tctttctgtt ttatgcacag    4080
gtggaatctt atttccgttt gcgtccaatc atgtatttta atatgcatgt atatatgtat    4140
gtgcatttgt atgcatgcga ttaagaacta gaataaattaa taattggaaa gctccatgaa    4200
agctggttgg ggactaattt tgtaactact ttattcccag atcctgtaat ttctctaaat    4260
aaaccctgga atcttgcctt atctccttca ggttaaaagc caactgcaag gtctaatgac    4320
tgcaggatct agctatccat tgtttctggc cgcctatgcg tgcactgggt gtctggcaga    4380
gaggctgggt aaattgtagt ttcattgtag ctgtctgaac ttggatttct cacgcctact    4440
tcactggaaa cgcaaactct cacagcattt tgttttagtt tcagaatcag agcaaattag    4500
aagtctgaat ttccttcaac acttggaaat aatttattta tttgaaatat attcataatt    4560
aattcgttat aaaaatgtat taaatgctta tttgagtcag cagaggaaga tagaaacttt    4620
atgaaagtag aaggtggatc tccttttttgc cttcattttc agaacatctc gtttacaccc    4680
attagttgaa acattaatgt catttttattt tcgtcctgat tatctcataa aacatttctt    4740
agaataacag caatacctat cattgaagtt ggataagaaa tattttgcaa ttggtttgca    4800
acttaaaaat ctgtttgcat gactcttttt cagtgaaagt aggcaagaga aattaaaatt    4860
cagaaatatc tcacctaatg tcagaggtaa tattgataat ttgtgttttta caaataatac    4920
atacaacaat aatgaaaaat aagtcctatc tataggctcg tatctcatgc ctatttttgg    4980
atgtattttt cagggtggtt tataaaatcc tccaatgaag ctactaacat tactccaaag    5040
cataatatga aagcattttt ggatgaattg aaagctgaga acatcaagaa gttcttacag    5100
taagtacatc ctcgaaagtt tatatggaca agttgttaga aaatttatc attctgtttt    5160
ggtccaatat tttatatata ggaactggac ttttttctta aaattttatt tattaaagat    5220
cttggatcat atttcatctg aggaggacta tactttcagc taaattttgt cattacagag    5280
gtttagagca ggagtcagca aacttttttct gtacaaggac cagcctttgt aggccagctg    5340
atctgtgtca catctagtca gctctgctat tgcagcacaa aagaagtcat agaaaataca    5400
taaacagtca gttctgataa acttttcctt atgggcactg aaatttggat ttcatataat    5460
tgatgtgtca aaaatattat ttttaaaacc aatttaaaat ataaaaacca ttcttagctt    5520
gtggactgta cagaaacagt tagtggtcca gatttggcca gtggaaccta gtttgctgat    5580
taatgcttta gagaaagata ttgcatttta gttaaaaaaa tggactttga gttagaattg    5640
agtttgaatt ccatctttgc ctattaatac tttggatgaa tacttaacct ttctgagctc    5700
tcttttccac atctgtaaaa tgggaataat gatcttatta tgatatggat gaagtcaaag    5760
agcatatatt tagcataaat ttggcatatt ttaaaaacta gctccctact tcctgaaata    5820
gctatttcca gtgtaggacg aaagagataa ataagtaaat ttaaaaagca accaaaaaga    5880
aaatacttat atagaattac tatatataat tgattagaat acttgttttt tttctttttc    5940
ttttctttcc tttttttcttt tgagatggag tttcgctctt gttgcccagg ctggagtgca    6000
atggcgtgat ctcagctcac tgtaacctcc gcctcccagg tacaagcgat tctcatgcct    6060
cctgagtacc tgggattaca ggcatgcacc accacaccca gctaattttg tattttttaat    6120
agagacaggg tttctccatg ttggtcaagc tggtctcaaa ctcctgacct caggtgatct    6180
gcccgcctcg gcttcccaaa gtactgggat taccggtgtg agcccccaca cccagcccag    6240
aatacttgct ttttttttaa gcatgagatc cttttgtgaa ttttacaaa ttgagttagc    6300
tcatgtgtcc taaaatactt gaagtccctc taatgattgc aggattcgct ggtgaataaa    6360
```

-continued

```
ggttgtaatt ctaaattaaa agaccattac acacacacac atgcacatag gtatgcatag    6420
atgtgcacac atataatcat acaaacatat atatgtttgt attaattaca acagaattaa    6480
aagtataaat acaaattgat aggatacctc tcaggtcttt ggaagggccg tttcaaatgt    6540
gagactctga agctcaaact tctttatctt tgtggaaaac cctcctctgc ctgttgtgct    6600
tattccactc taataatgta tagtaggtat aataaaagtg gaggtctggc aaggtatggt    6660
ctttactcct tgacagagct gctgttccag ctttcttcct ttcccaatat tagtggtgga    6720
agagatccaa gttactccaa gttatcagca gcctatccat aaggtcagca gcaacttcag    6780
tccttgcctc ttcagaagaa agaattcaac tgggggcaaa agcagaaaaa gagaccaagg    6840
caagtttcag agcaggaatg gaagtttatt ttaaaaggcc ttataacagg aaagaaagga    6900
aggtgtgctt ggaagagagc caagcaggca catgaaggtg agagaaggcc aagtgcccca    6960
cttaactgtg atcgtaggac ttctttacgc ttgcctcttt cccatgattc ttctcttagg    7020
gtgggctgcc cagccctcct aacccttggg aaaagagcac ccgcaatgtg tttagggaag    7080
tatacacagg cccatctgag tctctcttcc ttttttctggt ggagtgtacc tggaagatta    7140
tactatacca tttttgtctc taacacgcat gcccaggaag ttgcttctcc ctggagtctg    7200
cattcagtta acattttggt gttaacaggt gtggaccatc aagagctggc ctctccctgg    7260
cactgctaaa tcatttttag agaggcaatg cgatcaatgc tgaactgaac catcacctga    7320
cattctagag ggtgggggga gagccccctc ctgacttgct cctgtctaac tacttgtaac    7380
actaacttgt gacatagatt gaccaacaaa gaagaaaaat aaatgccttt atttctcttt    7440
ttggaccctc agcaagatta agcagtcagc ttcttgttta ttctccatgt ctctaaccaa    7500
gctcctctaa ccagaacaca gggggatatt cagcataaac acacaaaaga agaaattga    7560
aagaattccc tctcattcct ccaaggacca cagaatctcc agaagcctcc taaactctcc    7620
agattttcaa tttgccattt gtccatcaga gagctttcaa ttaaaatata cccatgggtc    7680
agagactatt aaaacctctg accttccatc tggtccccct ttaaaatctt ttgttctgct    7740
cttaaaagcc cccactgcct ctgaaatatc tgcctcagta gtgaatggga agattaatta    7800
ggagcagctt tttttcactc tgccttgatg tacagggttg tctgtgtttt cccttctttg    7860
aaaacaccca gttgaattca cagatctgtt taccatttttg catctctcta gagggattct    7920
tccttttcca cattgttttg caagataaga ttgttttaaa aggtgtttta gacttttggt    7980
ctcagaattt tactggtctg tatttgaata cataggtctg tatttgaata tataggccca    8040
atgaaatcac atattaaact acacttctta atctattaat cacttgagat gtgtgtcaca    8100
agtaatttgt tgatactaga atatcaaatt ttgttaaaaa gaaaaggtaa gaataagaat    8160
ttacacattt tccagaatag caaaaatcca ttcatagatc tctctcagac tggtttaaat    8220
atattccaag tatcgtcaca ttatctcaat tattattatc attattattt tcagacaagg    8280
tttcactctg ttgccaggct ggagtgcagt ggcacaatca tagctcactg cagcttggag    8340
ctccagcctc cccagtaggt agtactacag gcacatgcca ccgtgcccag ctaattccac    8400
cttttactaa ataccttcgt catcttgaag tcttggaaac actgccaaat tatttgtaaa    8460
caagatgaaa tgtactaaaa cagaaataac agtagctctt ttaaaggact gagataatgt    8520
attcgggcat agtggctcac ccatgtaatc ccagctcttt gggaggacaa ggcaggcaga    8580
tgccttgagt gagactctgt ctctacaaaa tattttttta acttatctgg gaatggtggc    8640
atgtgtctgt agtcctatct actcaggaag ctggagttcc aggttttagt gagctatgat    8700
tgcaccactg tattccagcc tggcaacaga atgagactct gtctcttaca aaaaaaaaag    8760
```

```
agataatgtg acaatactag aaacacattt aaagcagccc tacagtgata tataaacaga   8820
atttggctat ttgggaaaat ttgtaaattc atatttttat tcttattctt gtttattttt   8880
tacaaaattt gatattctgg taggttcaac aacttgtgac acacatctca aatgattaaa   8940
atcattgaga agtgctattt aatacgcaat ctaattgagc ctcaagtctt tgtgaagtag   9000
tgagacagtg atgttctccc catatacaga tgagaaactc aagacacagc tagggttaca   9060
tactgagtta atgacaacac ctgtattata ccacgtacat gatttatgct aattaattta   9120
tttagtgttt gcaatggatc ttttttttctc ctactaatct tttccaggat gtgttttgtt   9180
caaatgagtg agtcccaacc ctgataatag caaaatgttg tttcctagtt ggtagtgaca   9240
agactgttac aagaaaattc acttaatagt agcaaagcct tataatgatt ttctcccact   9300
tttttgtgag taggttcaag attccccata gtaattcctt ttgcttatag ggacagaggc   9360
atagctggca cttcaggata tctgcatcct acattagtta cattgcagtt tgtgatcttt   9420
gtaatattca agaaaatagc gatatgttgg ctgttttttct gttttccctg caggtgctca   9480
ctgataaggg atagagactc cttagctgcc tcttatgttt gtgtcctttt tgttacaata   9540
ttttccatat tagaaattct gtgtaagata ttttgccccct aaacatttac caaacgagga   9600
ttttaatact attttttataa atacaatttta aataactttta atataattat taaagtaaac   9660
aagttacagg aaattccaat tttaaaaaat tgagttactt taattcattg ttgattcatc   9720
aaataaaaaa attaaaatac atggtagaat gaaacttgaa actggaatta tcatagtcat   9780
gttggttatt agttttttta aatcaccata aggatggaat tatgttgatt ttataaagct   9840
acatatttaa aactagaaat ttatgaagtt ccaaaagttt atgaactata tatatata    9900 tatatatata tatcttttca tgctacataa tatcttgtca tgtatttaag ggcttaagtt   9960
aaaaatactt ccaatgagct cttcagggaa acaagaaatt tcccaggagg gagaaattta  10020
aaacaatcaa aagcaccaga atctaaatat attaaatgag aaattagtct actcctgaaa  10080
atatttctgg tagccaaatt ttggccacat aatttctttg ttaaagatat tcctcttcag  10140
actaattatt gtcattgatt ttaagtgtgt cactctgtat gatagatgga gtgcaagaga  10200
ttcattctga acttgtatcg gtatgttcag attattcttt gatgaagata ctttataaat  10260
ggttgctaat caaaaagttt atcacttgtc tataactctc agtatttaaa taatgtaat   10320 tattagtaat tcttgccatg ttacaccttg atcttttgga taaaatattt ttgtctgttt  10380 catatttac acagtgatat aaacagataa ttccatgtaa gttccaagaa gtataggtct  10440
taagaaagaa tatgataatc taccatacga ggttatagta ataggattac acataatgat  10500
acaaaaatca gttctccga ttttttctctt gatttagtac aaattagagc ataaaaattt  10560
caaagcagac tttgaaaatc tatttcatgc aataatacta ccactttaat tttttaacgt  10620
atcacacttc aaagtacttt tgtgtaactc tgctttactt tgttgatttg gaataaaagt  10680
tgattaaaca ttaatatcta accactttca attttttgttc accagtaatt ttacacagat  10740 accacatttta gcaggaacag aacaaaaactt tcagcttgca aagcaaattc aatcccagtg  10800
gaaagaattt ggcctggatt ctgttgagct agctcattat gatgtcctgt tgtcctaccc  10860
aaataagact catcccaact acatctcaat aattaatgaa gatggaaatg aggtaaaaaa  10920
taaataaata aataaaagaa acattccccc catttattct ttttcaaata ccttctatga  10980
aataatgttc tatcccatct ctaaatatta atagaaatca atattattgg atcttgtgaa  11040 taccttttaat atctcattat ccgtgtcaac tactttccta tgatgtttga gtttactgtg  11100
```

-continued

```
ttttagaaag attcgagaaa ttaatgcttg ataacagctg ctgttttta gtttttagta   11160
ctacacacca atatcaaata tgatatactt gtaaacctcc aagcataaaa agagatactt   11220
tataaaagag gttctttttt tcttttttt ttttccagat ggagtttcac tcctgtcagg    11280
caggctggag tgcagtggtg ccatctcggc tcactgcaac ctccacctcc catgttcaag   11340
ggattctcct tcctcagtct cctgagtagc tgggattaca ggtgtgcacc accacaccca   11400
gctaatttt gtatttttaa tagagacagg gtttcatcat gttggccagg ctagtctcga    11460
actcctgacc tcaggtgatc cacccgcctc agcctcccaa agttgtagaa ttacacgtgt   11520
gaggcactgc gcctggccag gagatacatt tttgataggt ttaatttata aagacactgc   11580
acagatttgg agttgctggg aaatgcacgg atccagtatg caatttgacc cagcaagttt   11640
ttattggtac ttaatgatta tgtctcaatt gatcaggttg aactctgtgc gaagaatttg   11700
tgtgtggaca tttggagagg acaagtttgg aggcaaggta ttttagcatg gtatttaaag   11760
aatttgcaat cttgtttgca agttggggca tatacttgag aaagagaaga caatgcagat   11820
aaattgatat atttattatg atgtatgttc aatatgaaag atcacaaaat ataacataca   11880
ttcatcctta cttaacatac ctcagttttta gagctaccgt atgtagaaga gtccatttct   11940
atttaggtaa gttcctttag tccttttatt actgggcact cttaattaca tgtagcttga   12000
aatatgtcca gtttgatcag tgaactgaaa atgtcatgtg atttaagtac atatataatt   12060
tttttcata gtaggtcaat aacctccttt tattgactaa tgaatcagtt tcttcttaat    12120
gattaatacg ttgttatgtt ttacagtcag tgatataatt ccatactaaa ttttctaatg   12180
tgattggagc ttttcatatt aactactgtt ctcaatcata gtagttaaca ataaactttt   12240
aaaaaatatt attaagccag gcgtggtggc atgttcccct aatctcagct acttgggagg   12300
ctgagatagg atgattgctg gagccaggag ttgcagacca gcttgaacaa catagcaaga   12360
ctccatctta aaggaaaaa aaaaaaaaag aaaaacaaac taaaaaaacc ctaaaatata    12420
ttatattgaa aaggcaatac cactacacgt catatagtct cagaatgttt gttaaataag   12480
tggtggcata tctatacagt taaataccga ggggtcttta aaacatgttc agaaaattta   12540
tttaaagaaa taaaatattg acaatgttaa aatgtataca tatgcttaaa cgtctctttg   12600
atctatcaaa tttgagaatt gtctaggtac aatgtggaaa agagcagaca tataatatat   12660
tttagttttt gttttttttt tttttgaga cggagtctcg ctttgtcgcc caggctggag   12720
tgcagtggcg gtatctccgc tcactgcaag ctccgcctcc cgggttcaca ccattctcct   12780
gtctcagcct cccgagtagc tgggactaca ggctcccgcc acgacgcccg gctaattttt   12840
tttgtattt ttggtggaga cggggttttca cagttttagc caggatggtc tcgatctgct    12900
gacctcgtta tccacccgcc tcggcctccc aaagtgctgg ttagttttt tttaagatgg    12960
ggtcttgcta tgttgtcgtt ttttttcttct cttttccttc ctcctcactt cccagttttg   13020
actataccat tgcttatttt atttcattat ttacttttgt attacaaaca tgcataatgt   13080
taccaaagcc tgttacataa tacaaaatga atcatgtaaa agtttcactt gggagatttt   13140
cctgaatagt gttagatacc tagtttctta attttttaaa tttatatcat tagttctttt   13200
ttattttat ccaagttata tatgtacata accacataat tttcctgagt gcttgctttt    13260
tctctatttt cctcttttcca gaggcaatca ttattcaact ataagttaat tctttttata   13320
tttacatcta tttctataaa ttacatgctt atatggcttt tatttcagat gcaggcatta   13380
tctattgaca ttgtgacaag tcagctccct gttcatccct tggccccaac caccatgttc   13440
tcttactacc tcccatctcc cagtacaatt taattgttat gaataacagt tcacagctga   13500
```

```
gctatgtggt aaactatgat ttctttttata cccctgcaca aaacagacaa gttctccatc    13560
cgtaggcaac aaatatgatt agtattttgt ggatcctatg agaaatattt ttaatgtata    13620
cagagacatt gtttcacctt tgattatgca gaaataacat cccataaaga tttaactata    13680
tattgacttt tttatgtcac aaaatgtaaa cagaaattat aaactaatat tgttttagtt    13740
atactcagaa tatataattt gaggctacca gtgcattttg gaaagtaaaa aatactctaa    13800
gactgaaatt taatctaact ttgataaagt caaccaaaaa ggcatttcct tgacattaaa    13860
aacttttctt acttgttaga atagctcata aacttgctgt aaaattcagt gtggcatagt    13920
ggtgctgcaa aattgattac cataaaggca aatcaagtga gacaagtttg aatattccct    13980
tgcctgaaag acatgcttat ataatgactt tgttccttta ttgatttttta ttgcacctca    14040 gcataatttt tcttttaatc ttacctagtg attcagatga gttcatttct catgtgaatc    14100
acagaaaaaa atatgggaaa tttgaatat gtggggatgt ggcaagtcgt agttgatttg    14160
gtttcatttt agcttctatc catgtcagaa aagggaaata actactgctc tagtcagtac    14220
aatgtaaaat ctgcccagat cccctcctca tctccaaatc cctcccattt gtattactgc    14280
actgaccaag acctatacaa tataatgttg aaaagaagtt ttgatagcag atatccttaa    14340 cttcttctg gtcttgaagg aaataccttt aattctttct caccattaat tatggtatttt   14400 actgttttct ttttctggtt atcttaaagt acatcctttc cacatatact aaaattttttt   14460 gctgtatgga tttatattaa acacattttt ctttaagatg agcatgcgat ttttctttct    14520
tgatctgaag atgacattca gtgatattct aatgttagaa taatcttata ttttttgaac    14580
ttgtaatatt agcattaggg ttttaaattc atatattgat atatattatg tttatactca    14640
tagcatgttt agtctgtgtt tttgcaatct atttgttggg ttataatttc aatattctac    14700
ttgccttcta aaatgagttg ggttttaat attttctgaa gtaggtttta ttgcaattaa     14760
attatttttt cctttaacct ttcaaactca aggaaaacca gttggccttg actctgtttg    14820
tggaaaattt taaactactg gtttaatttc tttattggtt gtaatatgac tattttacgt    14880
catataacaa tttttatttgt ttgttaaatg actttattgt ttgtcatatg ataatttat    14940 gtcatagaac aattttttatt gcttgatata tgactttatt gttatatggc tatacaacta   15000
gatttttttg ttgttttttga ccgagtctta ctctgtcacc caggctggag tgtaatggca    15060
tggtctcagc tcactgcaac ctccgcctcc cgggttcaag ccattcttcc acctcagcct    15120
cccaagtagc tgggactaca ggcatgagcc accgcacccg gctaattttt gtattttag    15180 tagagacgtg gttccactat gttggccagg ctgatctcga actcctgacc ttgtaatcca    15240
cccgcctcgg cctgccaaag tgctgggatt acaggcgtga gccattgtgc ctggccgatt    15300
ttttaaaaaa tgtattctta tgtcagtttt cataagtttt atttaaaatg cattttccat    15360
ttgatgtaag ctttcaaatt tatagtatag ttgttcctag tattttctta tcttttgtaa    15420
tctgttcagc gtctgtagat gtgcctcttt ttaataaata atattatttg tttgcgctttt   15480 tgctatttttt tttcttattg ctcttgagag ggatatgtca aatttactag tgtatccaaa    15540
gaataaactt tggcgttggc aatcttttct catctatctt tgctttatat tttattaatt    15600
ctgttcttgt tttataattg cctcttttat cttcttttgtg tttactttgc tgttctttgt    15660
aaaatcctca gtagaatgct taacttattg acattcagtc tttcttcatt tctactatga    15720
gtatttagag ccataaattt ccccttttaac ttcccttttcc acttcaacta catctcacaa   15780
atttggatta ggagtagttt aattatcatt agtatctaaa tattttttaa tttctgtatt    15840
```

```
ttcttctttg atcctgcaac tatttacaag tattttttaa aatcctgaat ataaagattg   15900
ttattgttat ttgtttgatc tgatctctaa attgaatata ttgagatcag ataatgtggt   15960
ttgtaggaca ctaatccttt gacaattgtt gaggcttcct ttggaaccta atatgtgctc   16020
aatttttata gacgttctgt gtttctttgg gaaaaacatg tatttgatgg ttgtttggtt   16080
taatattttg tatttgtaca ttagtttgag tttgcttatt atttggctga aatctccatt   16140
atccttaatg tgctctctca ttttgtctgc ttcctttatt aattagagat aaatgttaaa   16200
ttatctcacc tcactatagt gatgtctgtt ttatactata tatataaaat ttataattcc   16260
ataaatttat gttatgtata atttggagac ctattatcat atataaacag aattgttgat   16320
gaaatgacag acttatactt atgtagtagc cttttttatc tcgtcataat gttatttgac   16380
tttgtcctaa aattttttt aattaatatt tgtttggtat ttcttttca gcgggtttat   16440 gtcactgctt gtcaattggt acacagctga ttttatttag acatgctacg cttttaatt   16500 attcttttt ccattttcat tttttataat tctgatatac aatatttagg tcacttttac   16560
cttcctctag tgtgaatttt actcttcctt ttttccccta aagctttggt gtcataattc   16620
aatcaatatt tctacaatat agaaaccttta gaacactttc acttttgtta tatattacca   16680
atttatatgc ataattttaa ttcagtcttg tttcataaac ttgataaata tgtttattaa   16740
tatgatagta ataagaattt gggaattctt taaggctaat ttgaaggctg attcctcctg   16800
atcatttctc ttaggccca gggagcacta caaacctggc actgctttaa aataaatatt   16860
ttcgcttgag gcatactata taaacagtga atggaaattt gtagggttat gaattatctg   16920 gaacccttt ttcctgcttt acgctaagcc attactttcc atggagcaag tttatttga   16980 atttatcctt aaccctgaag gatattgttg ttcttttttt tttttttttt ttttttgtca   17040
cccaggctgg agtgcagtgg catgatctcc actcactgca agcttgcatg ctgggttcaa   17100
gtgattctcc tgtctcagcc tcctgagtag ctgggattac aagcacgtag gcccggctaa   17160
tttttctatt tttagtagag acgcggtttc accatgttgg tcaggctggt ctcaaactcc   17220
tgacctcgtg atccacccac cttgggctcc caaagtgctg ggattacagg cgtgagccac   17280
ctcacctggt caggatattg ttgttcttag accagcttta tgcacagtct tctgctagat   17340
tccattatgt gaaccagctt taaactaact cctgaatcct tttcatgggg ccataggctt   17400
tgatagatcc atctaaggca aagccaaatt tcgtgctacc tctgaggatt cttgctttca   17460
tttttatttt tttgcttctga atattcctta ctatttttt tccaattaa ttttaaactt   17520 aaaaaaacat atatttggtt cagtgttttt cattcttttc agtgcatatg ttgttcagag   17580
aatctagata aggccagttg tggattcccc aatcatgtac ttttttttaa agtaaattta   17640
atatttaatt tgttcctagg taattatcta agcactatta taatgattga gattaccaaa   17700
caaaggtact ttttatttgg tgattaaaat ctttctccaa aatcgaaagc tagtccttac   17760
aagttctctc aagaaattca tgaggttaat ttacttctaa ccttctgtga agcaactaca   17820
tatttaggct tgtgttcaca ctagcttagt atgtatgcca cttacaaaaa ataaatttct   17880
aattcttcct tctatcagta cacagtttac agtatatagt attccttttg gaagagtatc   17940
tttttacctc ctctgagctt ttcttctat agtacttact tattttatga ttgttgtttt   18000
tcatttggtt gattttttagt tattggtggg gtttttttag ctttgtttcc ttgaatagat   18060
ctaaccattt tgaggacaga atctgtgatt tattcatctc gtgaattctt cacaacttct   18120
agcatagtgc tgggtatctg atactatcat caaaatcctg aaggattcat tcaccctcta   18180
ctgacataaa agataatatt cattttttt gtgtttgatt atagtaatca aactttaact   18240
```

```
gttttatttt gattataata ttttgtttct ctagattttc aacacatcat tatttgaacc   18300
acctcctcca ggatatgaaa atgtttcgga tattgtacca cctttcagtg ctttctctcc   18360
tcaaggaatg ccagaggtaa aaacacagtg caacaaataa aaatgacaaa aagaagcctt   18420
ccttctcttc atatgttcag ccgataatta aagggtcata aagggacttt taatgtaatc   18480
caattcattt ttccacattt aagtaatgag aatgtcttag taagaagaag gaatattgat   18540
tatattttat taatggtatt tttaaagata caacttactg caatgagatg cacaaatccc   18600
aaatgcacat ttattgattt ttgacaaatg ccaacatctg ggtgatccaa atcccatcaa   18660
tgtacagcat attaccttca cttcagaaag ttcccttatg gttcttctta atcaactcta   18720 catacccag aggatatctt tctttgacat ttctgccacc ataaattagt tttgcctatt   18780 ctaattttc atcttttgt tcactctgtg ttttcctttg ttgaaaagag atccttaatt   18840
ttgacgttgt caaattattt tccttatgtt tttgcactt gggccttctt tattaatatt   18900
ctccttcttt atgatttaca gtgatataac ttcatgactt atgtatacca aaaattaaca   18960 atacatttt atttaaaaat agtattaata ttatcagatt gaagctaaat ataaaagacc   19020
agatagtata tgatagcaga aagtataatg aataaattta atttaaaata gctaaaaaaa   19080
tataaaatat actttaaaaa tcttaaatga atgtgatcta ttgaagaagt tgaagtgtga   19140
agtgtgaaat tgaagaacac tgaaatgtat tgagcagtga aaagactgtg tataaaaaaa   19200
caggttggcc gggtgcggag gcaggcagat caactgaggt caggagttcg agatcagcct   19260
ggccaacatg gggaaacccc atctctatta aaaatacaaa ataattagcc agatgcggtg   19320
acacacaact gtagtcccag ctactcagga ggctgaggca ggaggatggc gtgaacccgg   19380
gaggcggagc ttgcagtgag ctgagattgt gccactgcac tccagcctag acagagcga   19440 gactccatct tagaaaaaca aaacaaaaca aagaaaaaa cagttaaacc gtttatgttt   19500
ctggctgaga agacatcata ttataaggag aaaattacac ctagattagt ttgtaggttt   19560
actgcatacc caattaaaat cttccaaata attttttggac tttgacatta ctattaatcg   19620
taagaaagag ttataaagac cgttgtctct tatttccttc aaatagactt aaaatcttcc   19680
agatcaatgg ctaaatacaa agagcacaca tgttgtatgg gtttgctgtt tatgttcaaa   19740
tatcagatga gtttgctgat cggtgttcct cactggatca tctgtaaccc agccagtgga   19800
atgtcaattc tttcaaaact atgtatgtcc atatgtgtgt ttaaaacgtt ttacaggcca   19860
ggcgcagtgg ctaacgcctg taatcccagc actctaggag gccgagggg gcggatcaag   19920 aggtcaggag atccagacca tcctagctaa cacggtgaaa ccctgtctct actaaacatg   19980 caaaaaatt agccgggagt ggtggcgggc gcctgtagtc ccagctactc cggaggctga   20040
ggcaggagaa tggcgtgaac gcgggaggtg gagcttgcag tgagccgaga tcgcgcctcc   20100
tgacctcagg tgatctgcct gcctccgcac ccggccaacc tgttttttgta tacataatct   20160 tttcactgct caatacattt cagggttctt caatttcaca cttcacactt cagcttcttc   20220
aatagatcac attcatttaa gattttttaaa gtatatttta tatttttag ctattttaaa   20280 ttaaatgtat gcacttcagc ctgggcgaca gagctagatt ccgtctcaaa aaacaaaaca   20340
aaacaaaaat tcacgatcag taatctttga atttacgtct gaatcctgtg gaatatgaaa   20400
tatgggactc tgctttatgc tatttaaaat tagcaatttg cgatgttcat aaaatatagt   20460
ctatctagtg gttctcaagc tttagtgtct gtcacaataa tctggatggc ttgtaaaaca   20520
cagattctag tttccactcc ctaagtttaa tggggtggag cctgagagtt tgtgtttgta   20580
```

-continued

```
acaagcgtga tattgtttct gagggtccaa ggaccatctt tgagaatcac tggttttgcc    20640
tcccaattct gtctctataa ataagagtta gggagatgga agcttaagga aacaaagaaa    20700
attccgggct aagagtgcaa gattctattt attcacagtc atagaacaat ggatggtaca    20760
gtgtaagttg tacaagaagg tctttgtcta aaaacaaagc tcttttctaa cagtgacaac    20820
ttgcatttga gaagtgctga gagggaatat ctgtcacact tgttttcatt ttcaaagttt    20880
actctcattt ttaagctaat atgttttca gtttcctctc cctcacagtt tgttttgtga     20940
ggattgctga tatatcaaaa gacagccaca tttagagaca tttaaaggta caatctcctc    21000
aaagttactt atattaaggg taaagaaagt aggatattta cactaaaaaa attattttgc    21060
tgaaatcaca ttggttaatg actttgtagc cacagttaaa atagaatgag tgtgctccag    21120
agagggttaa caatgataaa tcagacatat agtgttatga ttaatagtgc attaatatta    21180
cattggtctt aggaagaaat acaagagcta aatgtaatcc ttttacagag gcaaagattc    21240
aaatgtcagt ttcccaatta gactttcctc attttattta atattacacc cacttaagct    21300
ctagttcacc atttgtatac tctatttaaa tgcttttta ttttttctat actacttatc     21360
accttttaat ataatgtatg ctttgcttag ttattaactt taatgctcat tattgtatta    21420
tcccatccac attacaggaa accccaact taagatggct acttaaaatt ttttgacttc      21480
atgatggtgc aatagccata ctcattcaat acacttctca acttaccatg aggttatgtc    21540
tggataaacc cattataaat tgaaaatatc ctaagtcaaa aacacacttt aggtgtataa    21600
ttattttcaa cttaggtgag tttagtaaga cttaattcca ttgtgagtga aggaggacct    21660
gcagtgtaag ttccttcaag ggcagagatt tgttgtatta cataggggcac tgcctaacac   21720 ataatagatc ttcaccaatt tgtcaaatta atcctagaat cagcttggaa acaattctat    21780
tttaatatct tatgtatatt tgtcgtgtac atgctatgaa aaatgtagtc aaaaaggaaa    21840
acaataacca aaataaaatg ataggatatt ggaaatcatc tgggacaggg gtttcaaact    21900
aggctgtgta aagactttcg aaaggcaagc atgacatggt tttaaagaga tcagtttgca    21960
gatcatcaat taccctgtgc gcttttttcat ggtattgaaa gctagcctgt cgtgaggtcc    22020
tgctccctat ttacaagcat tttcatctta ttttataaat gaaaaacatc tcctacccat    22080
tctaagtcaa tatgaagcat atatctgtgt tgtaaaaatc tctggggctt caaaaaaaga    22140
gacaattaga aatattgttt tcaatgttaa gatagtgaat ggttctaata gctacgtaac    22200
aaattcttag caattcaaat ggtttacaat tgagcaaaat taaaggtaaa cccaattgag    22260
tttccagcta atatcattaa aagacacttg aatgatggat caatttgtga ttttcagatt    22320
ataacttgaa agaagtttaa ataagttagt aacaattcca taacaaatct ttcattccta    22380
tccaagtttt ctcagaactt actgtaaaaa caagaaatgt aaattgaact gttgttgctg    22440
atcccagtct cattctagca ataatttgtt cacccactga acaaatgtgt taagataacg    22500
cttcactgtc ccactcattg cattaaaaga tatatttcta atcaaatttt atggttatgc    22560
attatatata agaattgcaa tgatgttgtt agacttaatt tgatactgct agtaattata    22620
attataactt aatctatctt tttttttttt ttttttgaga ccaagtctta ctctgtcgcc    22680
cgggctggag tgcagtggta tgatcttggc tcactgcaac ctccacctcc cgtgttcaag    22740
caattctcat acctcagccc ccgagtagct gggattacag gcgtgccac cacgcccagc     22800 tgattttttgt gttttttagta gacatggggtt ttcactatgt tggccaggct ggtcttgaac    22860
tcccaacctc aagtgatcca cccaacccag cctcccaaag tgctgggatt acaggcatga    22920
gccaccatgc ctggcctata attataactt actcttgaag ctgtttctta acacaatctg    22980
```

```
tcacaaaaat aaattttaa aaaaatttga cttataaaga tatactgatt caaggaaatt    23040
tgacagtgat taataaaaga cttcaagca tacccatatt taaggtaata gattctgaat    23100
tgaaatttag aataatgtgt gataattgtg gagtgttctc ttgggatcaa catctgtgaa    23160
aagcagagct ggattaggca gagggagaag tcaccctgca atgccagctg aaggatagcc    23220
ttggctaagc ccataaggag gtctggaata gtttctcaga attgtcctac gttagactga    23280
gatgtccagg tctctgtacc ctcacatcaa tcagtcactg aatgtgtggc attctagaaa    23340
gggacatgac cttgagcaag ggggctgtct acagctgagg caatccttga aggggctgac    23400
agatgaagat tgtctgcaga gagccttccc tgcagctgga gcaaaaagtc cttcattgac    23460
cgtgaatctg gacagctcat ctggtgccca gcacaaatat attttacttt agagtaaaat    23520
tctgtggggg aagatggaca atatacaagt tcaagaaaaa aaagagatg acaaaatttt    23580 gactgtaaag aacagcatgt tcatgtattt tttaaaattg atgatgttga atagtaaata    23640
aatacagtat ttaaatcctt tggatcaata taaaagttgt atacaatttc ttctaaaaat    23700
attaatattt atagtaagct agatattgca tgctttgcag ctacttaaag gtatgataaa    23760
aaattttaaa ttttagatga aggggtacat tgtcaaaatt aatttaggga ataggtgagc    23820
aaaaaaggtt ggaagatcac tgatttaatc taacagatca ttgagccaat gagaatatcg    23880
agactcaaat atgttataag atttgcacat aatcacttaa tgattgaaat cagacctgtg    23940
aagcaatgat gttacctgtg cattttctt tacttggtgg ttgttaagaa ccattaagct    24000
actccctgtg aacacacact gaagagagaa aaggtctcat taagggcttc ttagcctagg    24060
gtatctggac accttcaagt tgcgtgcagc aatgtgtaca cgtatatgct tttctgtgtg    24120
tgtgtggggg gggtgcttct gtagcttcag cttcgtagcc actaaatatg ggacaaatac    24180
aaacaaatat tactttattc atgtgcttct agcccatcta attccattct caatttaaat    24240
tcatttttcc cttgaatctc ttctttggag ctcatgcatt tctgaccttc ctgtgtgctc    24300
tgacctcttc cctctttcaa aaatgtccaa cagtccccat gcagaaaaac ctccttgttt    24360
tatatctgac tcatattaag tcattcccga tctcaacagg gcgatctagt gtatgttaac    24420
tatgcacgaa ctgaagactt ctttaaattg gaacgggaca tgaaaatcaa ttgctctggg    24480
aaaattgtaa ttgccagata tgggaaagtt ttcagaggaa ataaggtaag gtaaaaatta    24540 tctcttttttt tctctccccc aatgtaaaaa gttatagtgg gttttacatg tgtagaatca    24600
ttttcttaaa actttatgaa taccattatt ttccttgtatt ctgtgacatg cccaccttac    24660
agagaggaca catttactag gttatatccc ggggttaaat tcgagcattg gaatttggcc    24720
agtgtagatg tttagagtga acagaacaaa tttttctgtg cttacaggtt atggctgtgg    24780
cctacaaaga agcatgcact gggtttatta ttaactttca gtatctttgt tttaaatatt    24840
ttctacaaaa atgtttacta aattaaattg tagtatgaat tgtttataaat aatgagggaa    24900 aacaatttac acatagcaaa tttaaaaatt actgtcattt gatttgttaa tatattttc    24960 tctttagtgg gaaattaaat tttaaaaat tcccttcga ctgtagaaca ataggaatt    25020 tggcctgtgg ggtctacttg cttattatat ttgtaagcta gtggtaggaa atagcaaatg    25080
ctcactacca ctaataagaa catttctaaa tctgatgttc tgaggatttt tagagcttat    25140
agtagcaaaa agaaaaggga aattctatcc gagatgtcct tgttgtagg cctaatgaga    25200 aaaggttgaa gataaagttc tggtactcat ttaagtgtaa tattgaaaat tgatattacc    25260
gaatctggaa caaccaattt aaaataagga agaaagaca ctgtgttttc taggttaaaa    25320
```

-continued

```
atgcccagct ggcagggggcc aaaggagtca ttctctactc cgaccctgct gactactttg    25380
ctcctggggt gaagtcctat ccagacggtt ggaatcttcc tggaggtggt gtccagcgtg    25440
gaaatatcct aaatctgaat ggtgcaggag accctctcac accaggttac ccagcaaatg    25500
gtgaatgatc aatccttgaa tatcatagga aacttaacat ttgaaagaga ctttattaaa    25560
gaatttcctt tggtacaatg gactaagcat gtcttttttt attctctttg catttaagaa    25620
tgaaagaatt ttgaactcta aagtgattgg ttcaggcccc ttaccccctt attttgaaac    25680
ttgggcctgg tgggctttca aattcagact tattcagcta tttaaaaaac attatggtgt    25740
tacacatata ccataacttg cataacagtg acatagggggg ctgggacaga atatggggaa    25800
aaagcatata atattttttg ttgcagagtg tatgaatact tacgctaagt agtaagtggg    25860
gggcggggaa taaggaatat aaacagactt atgtctactc aagtcaaatt ttgctttcaa    25920
atgagttcag gtcagatcag gttttgctgt taaataaatt ccccccagat ttacagattt    25980
cacagtgtgg gtaagggaca ggagagcaga agttccataa acttttttaaa tggccaattt    26040 aggatatagg gcccaggaaa tgcatattgc ttcatttctg taagataaca gagataactt    26100
tcaaagagtg tttcctaaat gccagcattt tacttgcatt aacaacccta aagctagggg    26160
gtgttattat ctcttattca cagggaggaa agtgagacta gaagtcagcc caagatcacc    26220
cctcctctga atgggcagtt ggattcaaat tcaggcagtc tggctcacag agtccacata    26280
gtagtcttat gctgaaaggc tcccctgtaa acattaaca aagggagcta atttattttg    26340
aatgtgctca actatttaat gatgtttaca aaaatctgtg atcattaagt ttgtggggtt    26400
taaagctaac taaattttta aaacttgtat aaaatacttt gccaagtttt ctatgacatt    26460
tatgtcttca tctggtttta ctcttaaatt gtagactcct gtaaagagta tgtattttttt    26520 ttggctttgt aaatcttctt agaacataat acattgtcag agatttttttt ctttttttaaa    26580 aaatgacaca tattacccta tagtaaaatt atataaatct acctgaactt catttgctcc    26640
acctttttat ttccaagttt taaaaatgc agcttagcct aagctttatt agttatgcaa    26700
agtcaaaata atgaaaataa aatgagatta actggaatgt ttctgttgat tttcttcaaa    26760
tttgaatgat ggtattttag ggggaaatta tgttatttct atgggctaa tgtttattga    26820 attatatttt gtgctctata cattttttatt ttcttttctaa ttttacttttt tattatggca    26880 taattctaac atatacaaaa gtagagacag tcatcaacat gttgtcaatc ttgtttttatt    26940 tgtttatctc tccaattttta ttttgctatt attctaaaga attttgaaaac aaatcccaca    27000 cagcatatca ttgtgtcatt ttacccataa aaacaaggat ttgcagttac ctaagtttct    27060
tattagattg ttttaaaaac agagaaaaaa atggaaaaac aactctgatt tttcttaagt    27120
ctgaagaaat gataggatgt gtgtgcttat tttgaggtac agtttacatg caataaaata    27180
catagatctc aagagttcag ttcaataaat tttgcaaatt gcatgtgttt atgtcactta    27240
aaatagaata taagggcctt tccatcactc tggaaagttc ttttgtaccc ctttctggtc    27300
aattttctct gtgtccccta gaagcaatca ctatctagta tctagcatcg tgtattcgtt    27360
tgcctgggtt tgaacttcaa gtaagtggaa tcaaacagta gatttttttt taaagccttg    27420
cttatttcag tgtagtaatt tgagattttc tatcatattg tatgtattag ttttttttctt    27480 ttgatgattg agtagcattc cattgtggga ttatactacg gattgtttat tcattcttct    27540
gttgttagaa acctagactt tgtctaatat ttggctaata taaatgtggc tgttatgaac    27600
aattttgtac acgtcttctt gtgggcatgt gctcatcttt ctagagtacc caggagtgga    27660
attgctgtgc catagtgcac atttctgctt gacattgctt ttcaaaagag ttaccttaag    27720
```

```
tgattgtata attttagcct agattatcac aagcaatgta tgaggatttc agttgctctg    27780
cattctcgct aacatttgaa ttgttaatct gttttacttt aacaattcta gcaaatgtga    27840
aattagaatg tatttaatgt gatttataga gaaccgtttg aatgaaactg agtttttact    27900
ggaaatatgg caattttttt tttcagaata tgcttatagg cgtggaattg cagaggctgt    27960
tggtcttcca agtattcctg ttcatccaat tggatactat gatgcacaga agctcctaga    28020
gtaagtttgt aagaaaccat ggatggctat ttgggtaatt ttcttattga cagttttcaa    28080
atgttaggct tttatctcca ttttttagta cttaaatttt ccaacatggg tgttgcttgt    28140
aattttatca gtataaaata aagagtggt tctgttctgg aatttagtat atacatgagt    28200
atctagtgta tgacagccat gaaaatgaac ctttcagatg tttaacttca gggaacctaa    28260
ttgatcaatt gctccagaca ttgtgctttg aaaccccact atatttgtgt caagaccatg    28320
cttcctgtag gtgttctcgg gcaatgactc agtgtggcaa ggatactact gcaggcctgt    28380
ttctggaagg cactggactc ctctgatgca aaactttggc ccagggactc cttgatagcc    28440
tcgcttaaat agatgctgca cccaacactc ctctttcttt tcctcctccc tttttccttt    28500
attcaatatt agacctacct tgcagtctaa ggactttctc agggtttcct agctctctcc    28560
tcatttttcca cacatgcttt tccctagtaa atctcttact catatattcc tcttactggc    28620
tacgtctggg aggacccaga ataacacact atgagagcaa cttccatttt gtttttatct    28680
ctattcttct tcccttctg ctttcattat tgaaactttc tgctttcatt attgaaactt    28740
tcccagattt gttctgctta acctggcatt ggaactgttt cctcttccct gtgctgcttt    28800
ctcccattgc catgtccttt tttttttttt tttttttttt tgagacagtg tctcactctg    28860
ttgcccaggc tggagtgcaa tggtgcaatc ttggctcact gcaaccccg cctcccgggt    28920
tcaagtgatt ctcctgcctc agcctcctga gtagctggga ttacaggtgc ccaccactat    28980
gcccggctga ttttttgtatt tttagtagag atggggtttc accatgctga tcaggctggt    29040
ctcgaactcc tgaccgcagg tgatccgccc tccttggcct cccaaagtgc tgagattaca    29100
ggcatgagtc actgcgccca gccaccatta ttctttagag gtgagagaac actggctttt    29160
ctaaaagtga aattgataga gaccaaagcg tctggccagg tagtcccttt tcttctttaa    29220
gttcaagcct ttcttactaa ttttattcca gtatctatga ggaagcactt tttgaccaag    29280
ggcaaggcac tcatttttag aggtgaggag gctgacgtct ggggagtagg acacatctgt    29340
tcaatttaag ggcagattaa gaaagtaccc tggtctttct tccttgggc ataagatttt    29400
actgcattgg ttaagattca ggaccaggca caacttttga tagcaccata gactatgcat    29460
ttgcctaaaa atatgtataa ataaagacta agtattcatg acatttaaaa gataaaagtg    29520
attttagcat tacttgtaat agtggaaaac tgtagacaac acaaatcttc aacaatttat    29580
atgtactcga ataatacatt aattactctg atagtaaatg aagtgattaa aagatatat    29640
atgtagtacc agaataatta ataatataga aaaatgctta tattattaag tgaagaaaag    29700
caaatttcaa aactatatat atatagtatt atctcagttt tataaaaat taaacatgg    29760
ggctgggcgc ggtggctcac acttgtaatc ccagcacttt gggaggccga ggcgagcaga    29820
tcatgaggtc aagagatggg gaccatcctc gccaacatgg tcagtgaaac cccgtccgta    29880
ctaaaaatac aaaaattagc tgggcatgct ggtgcatgcc tgtagtccca gctactcagg    29940
aggctgaggc aggagaatca cttgaacccg ggaggcagag gttgcagtga gccgagatcg    30000
cgccactgca ttctagcctg ggcgacagag tgagactccg tctcaaaaaa aaaaaaaaaa    30060
```

-continued

```
aatttaaaac atgaacctgt attatctttg taattacaaa agagggatgc ataatattat    30120
ggaattagat gtgagattta tttagacgtc tacgatttgg tctggtttac taggtcaata    30180
tcagctgtgc tctgattgtg taatggaatt atctgattga ttgaaaaata acaaacacaa    30240
ttcatctgac attactgtgt cagcctctgt aagccatttt acaaatacaa tcaccattaa    30300
taacataact ttcatgaaaa agtgcatttt acattcaaaa tttcataatt aaaaatagac    30360
actatttatc cacctatact ttctaagcca taatgaaaca gtccatataa gtggaattta    30420
gttttaaaaa attgtttaaa agaacatatg gtttgtttat gaatttcact gtgaaaattt    30480
actctcttgg cacacgtacc ttgggagtgt gccaagatac tcaattctga ggttctctca    30540
agtggttagc agtttagcat tgtgcactaa ttagaaaaga cagtgtttta caaatggaat    30600
atatcatgaa ataaaagttt attaataaat gtgtgagtaa atgaggagag atataaagtc    30660
atataatggc cgaagaatgc tgagaactta aataaaagt tgatgaaatg tgagtgatgt    30720
taaaaacttc aatgttgact tgagtgggac agaaagggga caccatatat actgtttcct    30780
attttttcttt acatgtaccc tgaacacagt gtgattatgt ggttttaatt tgccttctac    30840
agtaacttcc aggacgataa ttatagtgcc aacggcaaca gtaatagcat gtatcctgca    30900
tggagtgcta attacgcttt agcacttact gttgtgctaa atgctttaca cacatctcct    30960
caattaacct ataaacaac aatatgagtt agtattgtga tactcattgt aaccaatgtt    31020
cagagagtaa gtgagagagc cagggcccaa attcatgtct gatgcaaaag cactttggt    31080
aaacactact tactctctac tcaatgacgc aagcatttag tagccacctc tgttgattat    31140
agtattggct cattcttatg cctctgctcg ggagaccttt aatggcgtct cacagcccac    31200
tcactcaaga aacatttata gaatgacttt tatatttcag gcactgtggt agaagtagga    31260
attaggtaaa gtcagtagta atgtcctatc ttgtattctt gattttagta attactttt    31320
aaacttggtc agtttaacta atggtttgct aattttgttg atcttttta agaatcaccc    31380
ttggtttcat tgattttctc tatttatttt attatttctc tttcaatctt tgtaatttcc    31440
tttcttatgc tttagagttt agtttagttt tctttgtcca gtttcttaag gtgaaagctt    31500
agcttaatga tttgagattc tttctatata ggtgtttaca gctatgtatt ttccttaag    31560
cactgttttt gctgcatctc ataaatattg gtatgttgtg tcttcatttt cattcatctc    31620
aaagcatttt taaattgtat ttgcaagttc ttctttgacc cattggttat ttaggagtta    31680
gttgtttaat ttccatatat ttgtgaattt cctaaattta cttttgttat tgattgctaa    31740
attcctttta ttgtggttgg attagtaaaa gaagtatatg agtaataaaa tgattgtata    31800
atttcaacct tttaaattta tccaggctcg ttttacagac atgatttatt atgaaaaatg    31860
ctccatgtgc acttgagtta cactattttt caatttcttt ctcaaggaat cttagtcatt    31920
ttatatccca gccagaatag tcatcatgcc ttacacttgc tctatgcttg cctgcctctg    31980
tgcctggaag gctcttcgcc ctcatttttc catgcccggc ccttattcat ctttaaaatc    32040
cagatcaagt gaaaccttct ttagaaagta attcctgatc tcacaagctg attcaagctt    32100
tcttttgtcc aaattttta gaattttacc tttgctctgt gatgttctgt tttatattat    32160
gattggtttt atatgtattt tcttctgagt gatttataaa ctctttggtg gaaagactga    32220
gtcttgtata tatttatatt ttttagtgaa taaaacacag tgccttaaac atagtagaca    32280
acaagtcttc tccaaattgt caaatcaaaa ttaatatgct acaagataca gaattataaa    32340
ctcaatactg tctatacatt aattactgga catctaccat ctaccaaata tgtttggaga    32400
cattttccaa catttaatgg tactttctaa tatttttgtg gtttgaaatt ttaatattca    32460
```

-continued

```
actattaaat atttgtggaa tttattttt  atttataaag tgagaaaatg acctaaagag    32520
atttatttct aaagagaacc taaagagaac ctaaagagaa atttcagtaa cattttcaa    32580
ctgaaacttc tccatgtatg tgcattattt ttttcattgg tatattagat tcttatatat    32640
aactattatt atgttctctt ctagttattt gtttacctcc ttgtggggac actacaatcg    32700
tggttttata ttgtgttgtt ttatggaaat atggactatt aattttatt  ctgaaaagga    32760
aatacattta caaagttcac aattcaaaag gatttatagt aaagttttcc tctcatccat    32820
ttacaccccc aaagcaactg atgttattag tttatagtgt attagcatag ttctctgctg    32880
cagagagagg tcccggaaaa agtgtgttgc tggtccactg caaaatgcag agggttttat    32940
agatgagctg gtgaagaggt agtgtctgat ttatataagt catggacaaa ctggttagac    33000
caggtgtgtc atttgcatag ggtgtgaatt tctggtggcc ccaccctaat cttttattat    33060
tcaggtgagt tctctgcctg agctgcgtca tagtgctcat ttctctgtta ctgtgcatgt    33120
gataacaaaa ccagggaaga tagaccctct atgtgtacat gcctggcccc caggtagcct    33180
ttttttttctt ttgttttttt tttttgagac tgagttttgc tcttttttgcc caggctggag    33240
tgcaatgacg tgatctcgct tcaccgcaat ctctacctcc caggttcaag tgattctcct    33300
gcctcagcct cccaaatagc tgggattaca ggcatgtgcc accatgcccg gctcattttt    33360
tgccttttt  tttttttttt tttagtagag acggggtttc tccatgttgg tcgggctgat    33420
ctcaaactcc cgacctcagg tgatccgctt gcctcgccct cccaaagtgc tgggattaca    33480
ggcgtgagcc accgcgcccg gctccaggta gcccttact  attggcacag ctgccagcat    33540
tctcccgcac tttcagcttg ctaatctatg tttgcagctc gattttcag  gctgcttttt    33600
gttagaaaaa aaaaataatt tattgggctg cttttgttta aagggaagc  tctgctgagg    33660
actctgttgc ccccattatc tgcttactaa atttctttct acctcctgta tcaatatttt    33720
atgtataatt aagtatatgt atattcttta cttgcctttt gcaaattttc tgtttattta    33780
atactctgct gttttgacta tgtattgtgc tttctaccaa tgtaaaatgc ctcttcatgt    33840
tgcttgatgc tttatacgtg gcatttattt gtaaatagtt taaataaatt ttataataca    33900
ttacttgaaa ttctgtttaa tatacaaact ccttagtgaa aaagggaaaa gagagaggaa    33960
ttatttcacc tttgatagag cattttaaaa cgagatgtta attctaatga attttccacg    34020
agaaagtgat cttactgatt gtttccttat tgcatgtgca gtagattcta ggttaagttg    34080
agctattcat atttcctcaa acaggtagac agggaacaac cacccgtgta caggcacaga    34140
agaaaacagg acatgacaga gcatgctgca ccgcacagcc tggagtgcat gagggtgcgt    34200
gaccgcagag aaagccttac aggacagatt gaaattctcc acttttgatt tcataactaa    34260
acatctcagt ataatatcag ataatgacat ttatttttcc aggccattat ttaagtggag    34320
ctgggtttaa ggtttggagt attcattaa  caggaacaaa atgcccgtgg taggcccaaa    34380
gaagtctgtt tttgccttac agctggattt tcataaaaat atagttacaa ttaaggtcga    34440
gattattcag tttgaacact cagtctctta agtttgtctg gaaacacatt tgtctctctg    34500
tagctgttta gtaaaagtat attgttttac atgcccatat caagaataag ttaatccatc    34560
atcttaatac agtaaaggca gatatgttga agtgaaacta caagaccccc accatttcat    34620
aaacattacc atgttttctt tctcggtcac ctgctgaaag ataaccaggg accatggcat    34680
atactgggtg gtctgcctga atctttattt ctgaattttta aaaatagcg  tgaagctttt    34740
aggggcttct gaaatgaaat cctttctttt gatcctcctg tcttcttagt aggtgtgtat    34800
```

```
gaaagtactt tgtaaaaaat aactatatac cagtgagaca aataagaatg gaaaatttca    34860
gagagttaga catcaagctc tttcttcagc acatgctctg gaaagcactt ttagatttac    34920
tactagatac tggtaaggca gatcaaattc ttatcaataa tttgaatctt aattatacca    34980
tttactagtt gcatgacttt gggcatgtta tctaagcctc ctgtgcccca tctgtgaagt    35040
ggaggtagca attcctcaga attatggtaa ggtttaaatg acgtattata ttcaaagcac    35100
tttgcactca ttaaagatat tatgagcaga tgctcaataa agtgaatcca ttaacatttt    35160
aatgcgttac ttcaaggttt ttttgtggct aataatgttt ttttgtgtcc aatagaaaaa    35220
tgggtggctc agcaccacca gatagcagct ggagaggaag tctcaaagtg ccctacaatg    35280
ttggacctgg ctttactgga aacttttcta cacagttaag agactatttt aatttttaact   35340 cttttaaggg ggagacttaa agaaaaaaat actatagagg atgacagaaa aagtaaaatt    35400
tatgtaatac cagcaggaaa caaaactgca agttagaacc agtgtaattt tgcctgtga    35460 acaattagaa atctttaagc aagattgaag atttaaaaat tatgagtgtt gctggaactc    35520
agaaaatgaa taacccaaag tatggtgttt tgacatgctg agcactttga actaaaggat    35580
aaaagtcctt agatgcagct tcagaatcaa taattctgac ctcttacttc accccacaag    35640
agcagagtgt aagtttctct ctgaagttcc cttatctgaa gctcctgcag aaggaagaca    35700
atgactttcc ttcccctccc tgaaatttta ttaaccaggg aagattgaac tcatgtagtg    35760
ggaaggaaga ctgaggcata tcactttatc tgcacaggct ttgtcacaag ctgttgactg    35820
ttctctagtt ccattcaagt tccaaagaga attatttata aactattgcc tgctcttggg    35880
gcccatttaa ctctcttgaa aaccatttac caccccctcaa aaccacctgc actcccccac    35940 ttcccccctcc tctatgaaga gggtgctagt taaactttag ccatttggcc tttgtttgag    36000 tctcatatt tgtttggctc ctgtatacac tggtgtgtta gtaagtttgt atgccttttc     36060
tcctgttaat caattttcag tttatttac cagacttgaa ccttcaaagg cagagggaa     36120 aattccctta aaccttatag tgttaatctg ttaaccagtt ttttttttta agaatgtctt    36180
ttatttttgc attagaaaag tcaagatgca catccactct accaatgaag tgacgagaat    36240
ttacaatgtg ataggtactc tcagaggagc agtggaacca ggtaaaggaa tcgtttgctt    36300
agcaaatatt gatcaagtaa ctgttatgtg ctggatacta ccaagctctg ggagtgcaaa    36360
gtgaatcaaa acaaacaaac aaacaaacaa acgaagaaaa tcggtggaac tcacctaaaa    36420
acaaaggaaa taagtatgaa ataattttgt attgtggtac agtggtgaa taaaagtgaa    36480 tgtttggtgc taggctgggc agatgaccaa ggtgaatgat aaattgtgca ggcctcaatt    36540
aaaggatcaa gggaagcagg gtagggaaag atgtgttttc ttccgagttt tctgaatttt    36600
tttttaccat attttttgcat aaatatcttc atgataacta taaacatcta tataaaatat   36660
cacactctta gaaattaag ataatcttgt attaatgaat cctttcatag ttttatttttc    36720 taccactaaa gccactgata aaatatatgg acatatgatt ccatagaag ttcagatgat    36780 ctactgatta atacatttta tacgtagtct tagttcatga aggctcagtt tcttatgaac    36840
tattttgttc tgtatttctt accaaaacag atactattaa atgcatatta aacatattaa    36900
ttgcatgttt cttacaagca gccagtgatt tattttagat caagaatatt gatatccttg    36960
ttgtttgcat attctaaaga gtactaaaca atatataagt ggctactgtt gaataatacc    37020
gagtacctat tttgtgccag ttccatgata agcattggaa atgggagat aaaagaagac    37080 acagacccaa gacaaacaac tgacagttg tgaagggagc catatgctta agggtgatca    37140
atgctttatc actcctgaga gctgggtagg caaagaaatt ccctcttcta tagaaaatac    37200
```

-continued

```
ttgagctgta ctttaaaaac tgcatagagg gagaaaatat ttgagctgta ccttaaaaac   37260
tgaatggagg gagaaaatat ttgagctgta ccttaaaaac tgaatagaaa gaataggaat   37320
tggagaactt cctatgtggc cactatgttc tcttactttg aatatattag aaagtggtaa   37380
gttaggtaag agaggagtaa tagagttaca aaaaatgtga acaaggataa ccttaaactt   37440
tcttaattac ttaatgtagt acttataatt atagtaatac attgaaatat atatttgctt   37500
tatcacattt atgctttctc agatagaaga aacacatatt aaaatcagaa ataacatatt   37560
ttcacaaatc ttggggaacc tagccttttt tttttttgag gcgtgagtgc tttgtattta   37620
gatgctattg agtcgtttgc aattttctct tttattgacc tgaaatgaca aataatcttg   37680
tatctatgct ttctagacag atatgtcatt ctgggaggtc accgggactc atgggtgttt   37740
ggtggtattg accctcagag tggagcagct gttgttcatg aaattgtgag gagctttgga   37800
acactgaaaa aggaaggtaa tacaaacaaa tagcaagaaa aaaaacagcc tatctgagtc   37860
tcagtttagt cttctgtaaa gggagtataa aaatactacc tcaaccatta catgtgtttg   37920
gtaaaaatac taatcaatt ttcagtgttg gttggttaat tatattgttt atttattttt   37980
gcatttattt atataacaca tatattattg atatttatgt attaagtgat aatctgaaat   38040
aaaggaatta tactgttaat ggttgttctt ggcaactaag aagatgaaga tgggttacat   38100
cactagagaa aacacactga aattagatta taagccaaag cttcctagtc agagactgta   38160
agcagacgtt cctccgtctc ttctaacccc agacctcaga ttacgtgtac aaagtaatta   38220
aggagataga tgctctattc agagaaatac aggtcttagg tctaatggga ttctgtcaaa   38280
agtttggaat ctgtgttctc acatcctgag ccctggtgtg ctctcacaaa aattaggttt   38340
acactcgtaa catcaccact ttagtcattt tagaatcttc atatgaaagc caagtaaaa   38400 tttagttcaa atgtttgctt tttaaaataa taattacaca ttgagagcag gaagttcatt   38460
ctctttattg accctgcaaa caaggtgtct ggggctgtaa aatgtaatct atatatttttt 38520 atcaaccata aaaacaataa tgtatgttgt ttgcatagta tttactttttt ttttgagaaa   38580 ctttttatat gtcctatctt ctttgaagtc atagcaacta gggagaagac atatttactt   38640
atcttctcat gttacagata ggttaaccaa ggtttagaga atcaagtaat ttccccagga   38700
ttatgtagct agcatgtggc agcataagag aatcagggct gaaactcaaa tttctcacta   38760
ccagtcctca aaaccatgat gtctctatt aaaataaaat gtaaaggcgc tcagttcttt    38820
tttctacaca gctatcttat atttgaagaa acaaacaat ggagacctaa atttacataa     38880
ttcatgaagt aggtagtgtt taattttatt acaaaaatgt ttcatgattt ttctaggaaa   38940
ttcctgtggt aactatacaa aacatcactg tgacaattac agaatatgcc aaagaaatgg   39000
aatgctgatg aataataata ggaaatttga ataatactat tgacaaaaac aaaagactcg   39060
agttaacagc tatagtatac acattcttaa gcacacatga atatttacta agatgatgac   39120
tactcgcaat tttgaaagca cctactcagt gctttctaaa cattattcca tttaatcctc   39180
ccacaatcaa gtggtgtctt catctttact ctccttgttcc ttgtatacag atgaagaaat   39240
ggaagtttag taggtttgaa taactttccc tcagtcacgc tgctagtgag agaaccaggg   39300
tttgaaacaa gatcttgcct taactccaag gtcagtgttt ataacctccg agacacatca   39360
cccctctgct gaattatgtg gttttcagca acagcaaaca ttgctgttgc taactgagcc   39420
cttgttgatt aattctggca gagaatggt tgaaatcata cggaccagct gatattgaac    39480
aattgttcat ttgatgtcag aacaacagga aagagttcta aaggattttc tttcagttat   39540
```

```
atctgctttc agaataccaa atgcatctag aaatttcttt ctttgttcta ggcagttgca    39600
gaccaccaat gacttcctat gcatagcgaa tcattataaa cctattagaa tgttttatga    39660
tcttgcaaga ttttttactgt cacatgtccc ccctttttcta tgtaattgtg ctattttgta   39720
ttgacaactt taaaatctta caaaaaaagt tacgtaagta aagattttttt actacaattt    39780
gcccttccca aaccatcaat gactttttttt ttttttttttc caatctgggc ttggtagtgt   39840
cctgggtata ttatgaattt ttttttctatc atttatatat acacatacat tttagggtgg    39900
agacctagaa gaacaatttt gtttgcaagc tgggatgcag aagaatttgg tcttcttggt     39960
tctactgagt gggcagaggt tagttggtaa tttgctataa tataaatttt tataaaataa    40020
agtagccagg acttgtttgc caagcacata aaaataagaa gtgaatataa tgagaaagta    40080
ttcaaagttt tttccccaaa atctgaagta acatattctt gttcaaaaat cagcaataaa    40140
aatctctgtt gctaaagaac taagttttgt ttgaaccttt tagagccact taatgtcaat   40200
tgtcaaaatt aatttatctt tatttcctgg gagtatgaga gtaaataagt agatatgcta    40260
gaaaccaaac atcaaaacaa ggagttagtt tcttaatcat attgtagttt attcttcaaa   40320
atattgtctt agcaaacatg aacgacttaa cagacttttc agtgaatatc ttggcataaa    40380
catgtcattt aaatggagaa tcttgtctga ttcaaaggga attaagctat ttcaaattta    40440
tgaaaaatat gaagttaaat tgtctctatt tcctgaccat gaagccaaat tttcctgtat   40500
catgtttgat ttctatcatg attctattac gctttccaaa atatctccta aagctaacta   40560
tacagagtct cgctctgttg cccaggctgg agtacagtga tgtgatttct gctcactgaa    40620
gcgtcagcat cctgggttca agcaattctc ctgccctagg ctcctgagta gctgggatta    40680
caggcatgtg ccaccacacc tggctaattt ttttatgttt aatagagaca gggttttgct    40740
gtgttggcca ggctggcctc aaactcctga gcttaagtga tatgcctgcc tcggcctccc   40800
aaagtgctag gaatacaggc gtgcgtcacc atgcctggcc gtaaggtata cttttcattt    40860
atctttctta attcataatg acctgctcta tgttaaatta tgctaaaagt aaggcagaaa    40920
tttccaccac agaatattta ctaagccatt tgaaaagtaa ttttacctgc atgtattgtt    40980
ggctttatat aacagaaacg ttagctataa agtaaatata tgcaaagtca atgtttattc    41040
cattaatttc cagtcatgct gtaaatattt actggctcct ttcatactcc agatattatg    41100
tgcctgtgga ctttaatttt ctttgaaaaa aaaaatggtg ctcctgtaga cttagtcaaa    41160
gttttataag aaagaatttt gccactatct ggaagaacct aatattttga cggtgtaatt    41220
tgtgtctttc aaattatttt tttcacttac agttgtattt ttttcattttt ttatcttata   41280
gtcagaatgc ttaggaaatt atgtatttta gagactcaga attcacattg atatctcaaa    41340
aaaactttgc tacgctttgt tctaaaagtg tgcaattatc aatattgacc aggagatggt    41400
accatcctac aggagagcct gacttctggt caggagatga tttaagttca cttatttttc    41460
gtaacatgaa atttaactta aaatttcata cacttaaaat accttcattc catatgaatc    41520
agacaagatt ctctgcttaa ataatgagat gtttatagga agattttcac tgaaaagtct    41580
cttaggtcat tcatgtttgc taagacaact ttttgaaaga taaactacag tatgttaag     41640
aaattaactc attttccact taccataagt atatggacaa tttcatctta aatattagct   41700
tttaacaagt tttgcttgtt gtttcctacc agtaatcttt attgaaattc tttcaaagca    41760
gctctttat gagaatttct tatgtcaaat ttgtcgttaa tatgggtcag ctcaattaga    41820
aatctacata cattaaatgt agatgtgcat tttgtgggggg aggggagtg ggttataact   41880
ttatatttat agttttcctt tttattatag gagaattcaa gactccttca agagcgtggc    41940
```

-continued

```
gtggcttata ttaatgctga ctcatctata gaaggtgaat atcgttggtc tcataagaaa    42000
agatgtgatt aaactaggag cagcagtcta gttaataaat tatgcactaa caaggaaggc    42060
tatgcattaa tgtgtggtta gggaatctac tgcaacctct gacaggaagc agtgtatgaa    42120
ccctagttga gagttgggtg agccctaggt gaacaggtgt ttcttttctt ctttcctttc    42180 cttttgttttt cttttctctt ttcttttctt tcttttctta ctttttttttt gctttgaagt    42240 atagagtact aattcagaaa agcagcattc tttgattagc ttcatctggc agatttcttt    42300
ttatatacag caggaattta gtaagtatct gttgaatgat taactcaggg acctaaagag    42360
ttctataatt tagaatggtg tagaaaaaaa gtatcatttg tggggtgcgg tggctcacgc    42420
ctgtaatcgc agcactttgg gaggctgaag cgggtggatc acttcaggtc aggatttcga    42480
aaccagcctg gccaacatgg tgaaacccca tagctattac aaatgcaaaa attagccggg    42540
cgtggtggcg cactcagtat agataatata ctaaatcaat cttgaattat aatgtatgca    42600
ggtactttag aaagggtagg ataaaaccac tctgggagtt cagaggaaag aataatagaa    42660
acttcaggaa aggcttgaga aagggaatag gcatttgagg ctgactttga agaatggaaa    42720
tatatttaat aagcaaagga ccaaactaaa ggaaatctca gattgatttt catgaaaatg    42780
aaagagtcca ttttcactac aatccagctc cactaatata tctatatctt gaccatatgc    42840
aacatcccag ccattgctct cctgttctct acactcagat tgctcttcaa cacctcttta    42900
tgtgtttaat ccttatcctt agaccctcct ttgaaatgtt actttttcag ggaagacatg    42960
tcttcatggc actcatcact gtcattatta agtaattatt tgttttacaa gtaatagact    43020
gtattcttta acaaggaaca gacagtatct tgcttattca ctcctagatt cctaacgtct    43080
tattaaataa atatttgtgg tatggttgca aaaaaaaaaa aaaggactaa atgaatgaag    43140
ggggaatttt ttagaatatt ttctttactg tattagtaaa tttgccatgt caacacttgg    43200
aacatgagac cttgatggag tcacgttggc atttttcttt tctttttctg gtttttttgt    43260
gtgtgttttt ttgtttctgt tcttttttctg tttttttgttt gtttgtttgt tttttctgtt    43320
tctgttcttc ttctgttttt ttgtttgtct gcttgtttgt tttgagtcag ggtctcactc    43380
cgcagcccag gttggagtgc gtggagcgat catggctcac tagtcttgat ttcccaggct    43440
caagtgatcc tccaacctca gcctccttgg tagctgggac tacaggcaaa cgctagacat    43500
ccagctaatt tttgtatttt tagtggagat gacatttgac catattaccc aggttggtct    43560
caaactcctg ggctcaagct gtctgtccac attgttctcc caaaatgcta ggattacggg    43620
tctgagccac agcttccaac cttccttttc ttctttgtca atgcctctga gctacactgt    43680
tctgaaagtt agtttacaca gtacatttgg ttattctttt ctccttctct tagggtagtg    43740
gctaagagct tgacctttgg cgtcagatgc ctggattcat tcctggccct gcaacttcct    43800
atttgtgtga cccaagctac ttactttctg tgcctcagtt ttctcacttc taaatataac    43860
ttctaagagc tcctatctca aaggctcctg taagggcaaa aaaagttaca tttgcaaatc    43920
tcccagacct gtgccttgca cagagtaaat gtcaaaaaaa gttaactttg attagtatca    43980
ttacacctac ttaaaacaca taaggtgaaa tatatacatg tatatatatg tatattatat    44040
gcccacccag aataaatact ccaaatatat tttcttgaaa catagaataa cgttctcttt    44100
attgatagtt ttttttctgtt tttttttgtt gttgttgttg ttgttattgt tgttttgaaa    44160
tgagatcttg tagtattgtc caggatagtt tcaaactcct gagctcaact gatcctcccc    44220
cgtcagcctc ccaagtagct gggaaaacag gtgtgtggca ccatacttgg ccatagtttt    44280
```

```
ttaagatttg atattttaat gtattttaaa aactcattaa gctttgctac ttatgtcatc    44340
cctggcttga aattgctcca ttgtgtctct ataattttca aaatcgagaa caaaggacag    44400
gaggtactat atgattggga caccattcat ctcacttgtt ttatatttt acattgtatt     44460 aatgtttctt tctcaaataa tacaaataat catagattct gaaatttcta atgttaaaat    44520
gtaaaatgta caaataaagc gaaaatcccc aatgcaaact actctcaaac ttagtcctct    44580
ctccaaaggt attactgtcc tcagttttgg gtgtttccat catgttggca ttaatatata    44640
gaatttagct tcacaaagca ccaagagcgt agtgggtgct atctcaggtg ctttacacgt    44700
aaaaaaatta ttcagtactc acaataactc tctgagataa gtaagtaaat atttttatta   44760 tccctttgt ataaaagaag aaactgacac tcagagaggt taagtaattt cccaaggcc     44820 acacagctag tgaagggttg agcttagact caaatcagac tggtctgttc caactttacc    44880
cctctaacca ctacactcta ttgtctctca ccaccttata caggtatttg gtatcatatt    44940
acagctaaat gcttctacaa cttgccttt tcattcagca acacattatg aaaactttc     45000 catatcagca catatctcgg tttcacttaa aaacaaaca ctaccaccag acaacaaaaa     45060
tctacaatgt attcaatagg acaaattttg tatcagtttt ctagctgctg gacagcttgc    45120 ttcagttgt tgtggttaat attattttat ttgcatgctt ttttggtata atgtgaggag     45180
agggtagaga gctacaagta tatttatttg gtcttcagat gtgggcaatt aaattgtaat    45240
aaatgctgcc aaactactcc actccccaat ttccactctt ataagcactt ctgttttaaa    45300
aattacattg gctgtttgta catttatt cttccagata aatttagaa tctaaaatca      45360 aatctttaag ttccataaac aattctgttg tggtgtcact attttaaaag cctcaacttt    45420
tgctgttctc aaacatggat ccgaggcttt gggataaag ctagttgcca tcctctgagt     45480
gtttcatgtg cttttacatt tctgggcatt cgcacaggct atgcctttag ctgcaaatac    45540
cattttcccc cccaactgtg tcctggttct agaaaaccca gttcaagagt cccctctcca    45600
agtttgtgaa tttgtcttga cttccctccc ccaaaactcc tcctgagtca gcagcccctc    45660
cctgtgctgt gttggcttcc caagaacacc tctcctgggt gcttcacttg attgtcacaa    45720
ccaccagccc cctcctgagg aatggggact gaaactctaa gaagagcacc tggttcacaa    45780
attcattgtt acaacaaata ttgattggtt aaatgccaga ttctaggatt gttctaaaca    45840
cttggggtat ggcagcaaac aagagagtgc accttatccc aggggactta tcgtctagtg    45900
ggagggccaa taataaaaag acaagtactt aatatgtttt atgttaaata gatgagtaat    45960
atagagaaac aagagccaag gttaaaagag agagtggcta aaattagggg gtaagagagt    46020
gctattttag gtagggtgat caggggaaat ctctcagaaa aacatgacat tagaccagag    46080
gaggaggagt aagtcatgca gatataatgc agaatactgt tccaggctgg aaggacagtg    46140
tgtgcaaaga tgctgaggga gtattcttgg gcagaatgta aaatgcagat tttgagaggt    46200
gacctagggt ttcatatatg gcagtgtggg ccatggtgag aatgatggac tttacagagt    46260
tagttgggaa gccattggag agttacagtt gaaatcaggt tttaaaacaa tcattctggt    46320
aggaatttag cagtggtctt tgaagaaaat aataacagaa agaaattaaa ttttaaaatc    46380
tattcttttc ttattttca ggaaactaca ctctgagagt tgattgtaca ccgctgatgt     46440
acagcttggt acacaaccta acaaagagg tatataatta catataattt aagaaaaccc    46500
aaattctaca aatgatgttt tcttgaggta ttatgttaaa cataggtggt gttttataac    46560
ttcttgtctt catttcatat aacatatatg acatcacatc ttcacagacc atcacatcta    46620
gtaaactgtt tacacagatt gcctcatttc tcaccacacc agtgtgaggt agcccattag    46680
```

```
tagcatcatg tctaccatct ccattcttaa aacagtgaaa ctgagctcaa agaacattgg    46740
ccaccaaagt cacacacaac ttgtacggta gccgaaccaa gacttggtcc tatggctcaa    46800
ctccttaatt aaaaaacttg tttatactct tcagtatagt gataccaatt aattcagaac    46860
acaggaatca ttaaatgttc taactgattg agaaagaata ttcataagaa taccaggtgc    46920
tggcttccag ggacagaggc tagatgagat cacaattaca tttttttcaga tagggattat    46980 aaataaaatt taaatgccat taagctttgg tttcaaaaga atggaatgga ggagtgacca    47040
agatgactga ctagaagcaa ctatggtgtg tggctctcac aaagagaaat tgaaggggca    47100
agtaaataca gcaccttcaa ctgaaacgag cagatactca cattgggact aatcaaggaa    47160
acaacccaac ccaaggagaa tggagaaaag caaggcagga cgatggccca cctgggaatg    47220
acacagagtc aagggaacct cccccaccca ggaaaatgat gagcgaatgt gcaacccag    47280 gaaaccatgc ttttttccatg gatctttgca acgcttaggt cagcagatac ccttgtgaac    47340
ccactccacc agggccttca gtctgataca caggtgcatg gagtcttagc agaacagcca    47400
ctcaggcatg cacagagaca caggagcttt agatacacca gctttccagg cttcatggca    47460
aaagtaactg caactccagc acagcaggag gttagacccc catacatacc cataaaaaag    47520
aggctgaatt caagggcctg agcagtgatg gtctgcaggc cccacttcca cagcacttca    47580
caggataaga cccactggct tggatttcca gccagccact ggtagcagtg ttgtgcctat    47640
ctggaaagaa gctcttgggt ggtggtgggg ggcaggagg tggggtgga gggtgggct      47700 gccatctttg ctgtttgggt ggcttagcca ttccccacctt taggctttgg agagcccaag    47760
atgactgggg gtggaagcgg taccccagca cagcacagtg gcctcacaaa acgtggcca    47820 gacttcctta taaagcagat ccccaactac gttcctcatc aatgggtgga gcctcccaac    47880
tagggtttct ggctaccccc actggtgttc tctggctaac agaggttta ggacaccctg    47940 ggatggagct gccaggagga ggggcaaacc accatctttg ctgtttgggt gacttagcca    48000
tcccaggttt cagacttcgg agtgtccaag acaaccgagg gctgaagtgg accctcacca    48060
cagcacagtt gctctacaaa aacgtggcca ggctactttt taaactgggt ccctgatcct    48120
tttcctcctg tctgggtaag acctcatagt ggggtctcca gccacctcct acaggtctgt    48180
tcaggctggc aacatgtcta taactccctt ggacggaggt cctacagtaa gaagcaggct    48240
gcattcttta ctgtttcaca gccatcaccg atgattcctc caggtactgt aaaatctgag    48300
gcaactagcg attggagtcg acccccccagc acaacacagc agccctgcag aaaagtggct    48360
agactgttta aaaaaaaaa aaagaaaaga aaaaaagga caagctccac tcaaaggtca    48420
ccaacctcaa agattgaagg cagataagcc cacaaagatg agaaaggatc agtacaagaa    48480
cattgaaaac tcaaaatgcc acagtgccct cttttcctcca aatgactgca tcacttctcc    48540
agcaaggttt cggaaccggg ttgaggctga gatgcctgaa atgacagaag tagaattcat    48600
aatatggata gggacaaagt ttactgaggt aaaggagcgt gttgtaaccc aattctagga    48660
agctaaaaat catgttaaaa cattgcagga actgacagta aaatgagcca gtttagaaa    48720 gaatagagct gaaaaatact acaaatgctg tcacaagtat tgatagcagt atagaccaag    48780
tgaaggaaag aatcttagag ttgaagactg tctttctgaa ataatacagg cagacaagaa    48840
tagagaaaaa ggaatgaaca aaaccaccaa gaaatatgtg attatgtgaa gagactgaat    48900
ctatgactga ttggtgtact tgaaagagat aggaagaatg gaaccagctt ggaaaacata    48960
ttccaggata taatccatga gaactttccc aacctagcta gataggccaa cattcaaatt    49020
```

```
caggaaatgc agagaacctc agtaagatac tacttgagaa gatcatcccc aagcacata      49080 ctcatcagat tctccaagga caaaatgaga gaaaaaatgt taaaggcagc agagggaaag     49140
gccaggttac ctacaaaggg aagcccatca gcctaacagt ggacctctca gctgaaaccc     49200
tgcaagccag aagagattgg aggccaatgt tcaacattct tagaaaaaag aaattccaat     49260
ccagaatttc atatccgacc acattaagct ttatacgtga aggagaaata agattctttc     49320
aagacaagca aatgctgagg gaatttgtta ccaccagact gtcttaacaa gagttattga     49380
gagaagtact aaatatggac aggaaagact atcaccatcc acgacaaaaa cacactgaag     49440
tacacagacc agtgatacta taaagcaatc acataagtct gcagaataac cagctaacat     49500
catgatgaca ggatcaaatc cacacatttc aattctaatc ttatatgtaa atggtctaaa     49560
tacaccaatt aaaatacata gagtggcaag ctggataaag aaccaggacc tattggtatc     49620
ctgtcttcaa gagacccttc tcatatgcaa tgacacacat aagtcaaaat aaatagatga     49680
aggaaagtct accaagcaaa tagaaaacag aaaaatgcag gagttgcaat tctagtttct     49740
gacaaaacag actttaaacc aacaaagata aaaaaaaaga caagaaggg catcacgtaa      49800 cggtaaagga ttcaattcaa caagaagagc ttactgtcct aaatatatat gcacataaca     49860
caggagcacc cagattcata aggcaagttc ttagagacct tcaaagagac ttagactccc     49920
acacaataat agtggtagac tttaacagcc tattgaaaat attaattaat tttcaagaca     49980
taaaataaca aagatattca tggcctaaac tgagtactgg atcaaatgga cctgatagat     50040
atctacaaaa ttctccaccc agaaacaaca gaatagacat tcttctcatc agcccatggc     50100
acttactcta aaattgatca cataattgga agtaaaacac tcctcagcaa aagcaaaaga     50160
aatgaaatta aaaacgtctc ttgtactgcc gtgcaaattc aaaatcaaga gtaagaaatt     50220
cactcaaaac tatgcaattc catggaaatt gaataacctg ttcctgaatg acttgtgggt     50280
atataatgag ataaaagcag gaatcaagaa gttctttgaa actaatgaga caaagatat      50340 gacacaccag aatctctggg acacagctaa ggcagaatta aaagggaaat ttatagcact     50400
aaatgcccac attaaaagtt agaaatatct ggccaggtgt ggtggctcac acctgtaatc     50460
ccagcacttt gggaggccga ggagggcaga tcacaaggtc aggagatcga gaccatcctg     50520
gcaaacacag tgaaaccccg tctctactaa aaatacaaaa aattagccag acgtggtggc     50580
gggtgcctgt agtcccagct attcgggagg ctgaggcagg agaatcgctt gaacccggga     50640
ggtggaggtt gcagtgagct gagatcatgt cactgcactc cagcctggac aacagagaga     50700
gactccgtct caaaaaaaaa gaaaaaaaca ttagaaagat ctcaagttaa cagcctagtg     50760
tcaaaactaa atatactaga gaacaaaagc aaacaaaccc caaagctagc aaaagacaca     50820
aagtaaccaa gaccacagct gaactgaagg tgttggagac atgaaaaacc cttcaaaata     50880
ttaacgaatc caggagctga tttttgaaa aaaattaata aaaatagag tgctaactag       50940 actaataaag aagaaaagtg ataagattca aataaacacc gtcagaaatg ataagggga      51000 atattctcac tgaccccaca gaaatacaaa catcagagaa cattataaac acctctatgc     51060
acataaacta aagaatctag aagaaatgga aattagctgg gtgtggtggc aggtgcctgt     51120
aatcccagct gctcgggagg ctgaagcagg agaattgcgt gaacgaggtt gcagtgagca     51180
gagatcgcgc aattgcactc tagctcaggt gacagtgcaa gacttcatca aaaaacaaaa     51240
caaaacaaaa acagaaaaaa aaaagaaaa ggaaaaagaa aaaaaggat aaattcctgg       51300 aaacatacac cttctgaagg ctgaaccaga aagaaattga atccctgaac aggccaatca     51360
tgagttctga aactgaggca gtaataaaata gcttaccaac caaaaaaagc caaggaccaa     51420
```

-continued

```
atggattcac agcttaattc taccagaggt acaaagaagg gctggtacta tttctattga      51480
aactattgcc aaataattag gaggagagac tcctccctaa ctaattctat gaggccagca      51540
tcatcccaat accaaaattt ggcagagata caacagcaac aaaaattcag gccagtatct      51600
atgatgaaca atgatgcaaa atcctcaat  aaagtactgg caaacagaat ccagcagcac      51660
attagaaagc ttatccacca caatcaagta ggcttcatcc cagggatgca aggttgattc      51720
aacatatgca atcaataaa  tgcagttaat cacataggca gaactagaaa caaaaaccac      51780
atgattatct caataaatgc agaaaaaagc tttcaataac attgaatatc tcttcatgtt      51840
aaaaactatc aataaactag gtattgaagg agcaaacctc aaaataataa gagccatata      51900
tgacaaaccc acagccaaca tcgtactgaa tgggccaaag ctacaagcag tccttttcaa      51960
aaccgacaca aaataaggat tcttctctaa tcactcctat tcaacatagt attggaagtg      52020
ctggccaggg taatcaggca agataaaaaa ataaagctca ttcaaataaa aagagaggag      52080
gtcaaactat ccctgtttgc agatgacatt attctatatc taggaaattc cattgtcaaa      52140
gcccaaaagc tccttaagct gataagcaac tatagcagtc tcaggataca aaatcaatgt      52200
acaaaaattg ctagcattcc tatacactaa caacagacaa gccaagagcc aagtcacaaa      52260
ttaccactca ttcacaatta ccacaaaatg aacaaaatac ctatgaatac agctaactca      52320
ggaggtgaaa gatctctaca aggagaacta caaaccactg ctctaagaaa tcagagatga      52380
catattcaaa tggaaaaaac attccatgct catggatagg aagaatcaat atcattaaaa      52440
cggccatatt gccccaagta atttatagat tcagtgctat tcctattaaa ctattgttgg      52500
cattcttcac agaatttgaa aaatctgttt taaaattcat atggatccat aaaagagccc      52560
atataaccaa ggcaatccta agcaaaaaga acaaagctgg agacatcaaa ctatactatg      52620
aggctacagt aatcaaaaca gcatgatact ggtacaagaa cagacattgc ggtttattgt      52680
atattattga atgactttgg caaccctact ggcaagaaac aatattaaat tgaatccttta     52740 cccttaacca gcttacttct ttttattttc tttgttgtga gatgagaaat agttttgact      52800
gtagtatctt ttaattcaga aaaatagaca aaaagatcat atgctatgcc attcatctaa      52860
agacaatggc ttggtatgaa tttggtgtag cctgtttatg ctatgcactt catacattta      52920 ttttttataat atagttcacc tatatataat cacatgagta ttttcccact tgtcagaaac      52980
ttataattct tgatgactgc taatgtatgg atagcatccc ttgttttgc tgaattgtgg      53040 cttagttact cacttctggt taatggacat ctagttttta atatatctga tttgtaagta      53100 ttctctttt  ttcttttaat ttgtgtagct gaaaagccct gatgaaggct ttgaaggcaa      53160
atctctttat gaaagttgga ctaaaaaaag tccttcccca gagttcagtg gcatgcccag      53220
gtaaacaaat gaatgaagtt tccactgaat tcagtgtggg attgttttga aaataaaagc      53280
acattttctt tcaatcatta agtgaaaaat taagtttcaa aatggtctaa atctgataa       53340 agaaaagcat tactttggtt cacaaataaa atattactat gtgttttgta gttaaatctg      53400
caggatatca aaatgtgatt tctctttaga atatgtaata tatacatatg gaacatttca      53460
gcagattata aagattggtc atttcttata tgaaatgcgt gggatgagaa gtgttttgga      53520
ctttggattt ttttaagatt ttggaatatt tgcattatac ttactggttg aacatcccta      53580
atctgaaaat tcataatctg aaatgcttca gttagcattt cctttcagtg tcatgtaggt      53640
gcttaaaaac ttttggattt tgcagcattt tttaaaatgt tctaatcttt aattttgtg       53700 agtatgtagt aggtgtattt atttttgggg tgcatgaaat gttttgatac agattttgga      53760
```

-continued

```
ttttttggatt agggatactc aacccatgat agagataatg gtgaaaagta attttcctcg    53820
tttttctgcc acctcatcac cttgtaatta tcctttttct gaatatcata tagttaacaa    53880
atattttgct tattgcaata aaaatgcaag catcatttca acattggttg tatcttcaca    53940
agcaagggaa gaagaataaa tatctcagtg ctctgagttt atcgatgtca acagcactat    54000
ttatattatt aagggcaaaa tttatgtcca aattatctga aaaatatttg cttttcactc    54060
tattatgtac aacaaataaa gatgataaat ggaatgaaat aatcttaagg aaaatgtttt    54120
ccaacttcag aaacctttaa caaaatgtga cataaaatag tcattcctac acgaaatagt    54180
ctcatagaag gagatatttt gtgatcaaaa ttatattctt ttcatgtttt tgctgcatgt    54240
ctaaagctgt atgtttaaaa ttacatttat aatagtaaga atggggttta gtttaatgga    54300
catgtaatct gtgcttaatg aacaaattac tttgaaataa ttctgttgtt ttatctctaa    54360
aaggataagc aaattgggat ctggaaatga ttttgaggtg ttcttccaac gacttggaat    54420
tgcttcaggc agagcacggt atactaaaaa ttgggtaagt gaatctcaaa ttatctaaga    54480
ttatttatga atatgtttta actaaacaaa taattctgac tccaaaaagt gactcaagca    54540
ttagaggaat agagaaattt gaaagcagag ggagaagtct caatggttga cagtatcact    54600
actacgtagg ataactccta tatcttgtat tccaacccta aattcaagtg tcagttggta    54660
tcaatactca tgtctgcaaa tgtgaacttc tgtgtactcc tttaaacata ttttctgttt    54720
catttggtgg cattgcattc actcagtcat ttaagttgga aatgtaggaa ttgtctttga    54780
tttcaccctc ctccttattc aaaattagta tctccccatt atcattcaaa attaagagtg    54840
tatttggatt tccatctctt actgtatctc caattattaa acaaataaca agtcattaaa    54900
caaatgaaaa atgatatata tattagtctg ttttcctgct cctaataaag acatacccga    54960
gactgggtca tttaaaaggg aaatatgttt aattgactca cagtttcata tggctgggga    55020
ggcatcacaa tcatggctga aggtgagtga ggagcaaagt tacatcttac ctggcagcag    55080
gcaagagagc atatacaggg gaacttccct ttataaaacc atcagctcac atgagactta    55140
ttcactatca cgagagcagt gcaggaaaac tcgtccccca tgattcaatt acctcccata    55200
aagtctctcc catgacacgt ggggattatc ataattcaag gtgagatttg ggtggggaca    55260
cagagtcaaa tcatatcagt ataatacact gtgtacgtgt aaaagtcatg attccctttc    55320
ttttgttgtt gattatatat atatatatat atatatggtt ttcattttct tcaaagtaaa    55380
ttgggtacat agtttataaa atgtcaagta gttttataag aacagtggtt tataattaaa    55440
aacagttgtt tcttatttcc atttcatatt cataccaccc ctgatttctg ttcatcagat    55500
gaaaccttt tcaactttta tgatacatcc atatttataa gtaatatttt aatcctgata    55560
cttttttcaat tttaaatttt atgttataaa gaaaaatcat tctcacagtt ataaaaatgg    55620
taaggaagag ttcattcaaa actattccaa taagaatatt gcaataataa gagatcgagc    55680
tcaactccaa atacagaaaa gacatttggt gatttagagt tgacattaag tttctgtaag    55740
cctttcctca tgggctatcc ttcccagatg gaaaatcttc agtctcctgt ctgtgaggta    55800
ggaggttagg cagagttatg caggaggtga tagtgaggat aaatattaat attgtctaca    55860
ttttactacg aaaaaattac aacaaagaaa agtcaaatga ccacctaaag ttttggtag    55920
taagtcctga agcctagatt caaaccctgg cagggtaatt ccagaatccc agtctcttca    55980
acacatcagt acataaaatg tcctttttata ttaataataa aaaataagca tcttaagatg    56040
atcaaaagtg ataaaccagc aattcacagt ttgaaaagtc cttccttcta cctatacttt    56100
tggttttcct gacacctgtc tgggcctccc ttctctctcc ttagtgagat tttggatcca    56160
```

```
ctactgcacc cctcaccact cagactctcc agccttcagt acactgcttg tcagacaatc    56220
atttatccat ggaattttag tgattaagca atttagtgtc ttctcctata taatattgtg    56280
taatacttat gtacttgcct ttaacaattc gtcttctttt tatccaaatg caagattgtc    56340 ttgtctttttt tttcagattc ttaaaacatg aatctaagaa tgcaatgttc tgcattctta   56400
gaggcaagcc agtttggtcc ctttcaaata attttttaaat aatatttgtt atatcatata   56460
cacatatttt aattgataca agcctggaat gtgtttatgt atcataatat tagccattta    56520
ggatgtagct tattgagatg cttaagtact ttccttgatc catcactgac caatcttact    56580
aatactaata gtaaatatgg tgctaatcat tttttgtaag ctatccctat aagagatatg    56640
ttttgttgtt ttttctgtag gaaacaaaca aattcagcgg ctatccactg tatcacagtg    56700
tctatgaaac atatgagttg gtggaaaagt tttatgatcc aatgtttaaa tatcacctca    56760
ctgtggccca ggttcgagga gggatggtgt ttgagctagc caattccata gtgctccctt    56820
ttgattgtcg agattatgct gtagttttaa gaaagtatgc tgacaaaatc tacagtattt    56880
ctatgaaaca tccacaggaa atgaagacat acagtgtatc atttggtatg ttacccttcc    56940
tttttcaaat tcctcatctg tatggttcta ttaatctcct aaatataatg ggctatctta    57000
ggtcatttat tatttattgc tatttcaagt gatccaatat tctgtttatg tctataaatg    57060
tattttccat tttatggatg ctcacgtctt ataatataaa aatataaata ccttgtaaaa    57120
cacaaaagat gatggcttct atattgttcc tttcttgaa ctatagagca gtgccattag     57180
aaattatgtt ctttaagcat ttgatgatcc caatttctat ttcagattca ctttttttctg   57240 cagtaaagaa ttttacagaa attgcttcca agttcagtga gagactccag gactttgaca    57300
aaagcaagta tgttctacat atatgtgcat atgtgtgtat gtgtgtgtat atatatttat    57360
ttaaaagtaa actaacatga ctgttgctga actagctttg ggaatttctt gctgttttct    57420 ttttttttaaa tttgttttac tttaagttgc tggatacatg gacagaacgt gcaggtttgt   57480
tacataggta tacaagtgtc gtttcctgct gttttctgtc tttccactct agcacgtcct    57540
atgtagggct gccccatctc aaaagaccta ctttcgacat tctgagtggc aattgtgccg    57600
ctcagaaatg tcagtccctc cctcctgaca tttgatcagt tacaaaatac tctgcttaac    57660
attgaaggtc ctctactgtg tgaccccagc tgttccagt tttatttctt gcttttttcag    57720 tatctgtaca tcataactca gccagactat ttattttttca aagcatgatt tctttctacc    57780
tcctttgttt ttgtcattac ctccacatag agctccttat ttccacttcc atctggcaaa    57840 attctgtttta tccagaatag caaatattgt gaagccatta attttggaaa tgttaaacat   57900
ttaggattaa ttctgtgtaa gattacacaa gtacaacaca atttgaacaa attttaaga    57960 tggaaggaaa aatacttggt gagaatacta aggtaatttt tttaaagtat aattttgagg    58020
gcagagatct gtgtattaaa tatagtatca tgatataaat atcaaatccc caggagctga    58080
tgtaaggaca cataaaaaga ttacagtaga tgatgtagaa ataggcttgg tgatctataa    58140
ggaaatatta gtaataaatg atacagcaaa aattaatggg gaaagattac tcaaccataa    58200
tattatatga actatgttag tacctgctat aactgctata aaagtaaatt cagaatcgca    58260
cttcacattg tatgctaaca taacaacag gtgtaaagaa ttatttagta aaaatggaaa     58320
tttcttgaaa gatgccaggt ttagaagcaa tggggaaatg atgcaatcag atttgagacc    58380
atttgaaatg gttcagaata cgaaaattaa tattcacaag aaaaattaag aaagttgaaa    58440
acttattttc tagcaaaaat ggagagtaat atatacatta taaaaatatt ttttgaaaat    58500
```

```
taatttaaac agtccaaaag aaccagctga aaatatcggt aagaaacaag acaaataatt    58560
ttaaaaatgt tgtcaaagat acacctgcaa agaaacatgg caaaatattg cagttcacta    58620
atgcataatt cagaaataca aatgaaagta atgtgatgtt attttttataa cacattaata   58680 acaatttaaa ccttggtttg cccattgctg tagctggtac actgaagcat atgctctcca    58740
tgcttttctg atagcattat gaattatttt agccttttg aaaaagatag atacatattg     58800
ctaatgtgtt caagagctgt cacagagtcc tgtgctttga catagtattt ccacttcttg    58860
gattatttct taggaaaaag tctcaatttt ggaaaagaaa ggctgcctgg agaaagattt    58920
gaagtataaa attataatag caagtaattc aaaataacct aatgcctaag agaagagaaa    58980
ttactaaaaa atttgatatt caccaatttg aacattttat aatcctaaca atggattatt    59040
agaaatacaa cataatagaa gatacttaga ataaatatg aagtaagcaa aaaggttgta     59100
aaattgtaaa tataatttga ttaattttta tttaacaaat acaggaaaaa ctttaaggga    59160
attaatgaat tattataata attgtgctat cctcagggaa tattggaaga attgttttcc    59220
tattcttttc aattctttat aattttata tgtgagtaaa aaagtcaaca ataagaaata    59280
cattttaagg agatcccaaa caccatgtat cctataaaac tggttttctt tttgtattta    59340
aaagaaaaaa tgttttctcc ctctgacaaa atgcctcatg gtttgaattg tggtttgttt    59400
aggacactta ttgtttggca cactcagctt ccccttcctt tagtatttct atatttgttt    59460
tattttctgt aagtgatagt aaagatacac tctgttccct atatgatact tacaaattct    59520
gaaacacctg agcagtgctt tgcacataat agtaaattct gactaagtaa attaaactga    59580
atgttgaatt tctcaaccaa aactttgaaa tctaaggaag agacatgact ttatcctgct    59640
tttcttgtat cacttcttgc cccatcaaag aatataagac gttaacacag gatcagaga    59700 aagagaagtg tgtgtgtgtg tctgtgtgtg tgtgtgcacg cacgcgcacg cgcgcattta    59760
cgtgtgtgtg gccacatgag ttttgtact tgtagcaatt cttgtgaat ttgattccga      59820 aacccattgc atcttattga aattatcctt cattcgattg tctcaactgt ttatcggagt    59880
tgctaacagg tattctgtgt ttcatttacc tttatactat cacagaatct gaattcatga    59940
tgccaaatac ataaatgtta aaaatagctc aaatccaaat tatgggagtt aagttgttc     60000 ctatttccct tttgtcggca aggtgcagtt gaaagaacaa tatcaatctc ctatttcact    60060
ctaaaacttt ctagtgtgaa tttaggcaag ttatttaact catgatcctt tgttatctca    60120
tctacaaaat ggggctgtta ccctacccaa cttgcagaat tgctctgaaa attaaaaatc    60180 acatttgta taaagattca gaacagtaat tggcacatag gaaatgatca ctaaatgctc     60240
ttttagtaaa actaaattat gaaaagcaag aagtaaatta atgaacaaga tgattcatgc    60300
tttcttattg taatgatttt tctcagttaa ttaaattgtg aaataattgg tatattaaat    60360
tcagtaactc attgttgaag tattcagagc ttgctgataa actttcaatt atattgaatc    60420
attcttatta taataacaac cccaacactc cttttagaat gtaagttctg taaaagcagg    60480
gagtgtttga taaatagcag gtatccaaat attgttgaaa gacttaagta atcaccatct    60540
gttgtgttca taataggttt agctttaaaa ataaaggaa tattattagt tatcacttgg     60600
taaatattta taatttgcca ggcatcttac taaacattag caagtcatct tatttttaata   60660 ttgatattac ttcagtgagt agattgctag gatacctaag gtgaagaaaa tcttgcctat    60720
atttgtatat ctgggttgat cagttaatta tgccaatgta aataaaaatc actattattt    60780
tttccatttg cacatacaac tgtttctgtg cttttataag cctgagcagt atagtatttt    60840
ataagatttt aaagatgtca tagctatgta tgttattgtt cttaatttgc atattacaga    60900
```

```
atgttaaaat ttacaattga catttgaaca acagtgattt gaactgcaca ggtccactta    60960
tttacgaatt tttttcaatt aatacagtga gccctctcta tccatagatt tcacattagc    61020
aagcaaacac agatggaaaa ttcagtatta ttcactgtaa tccccaggta ctcaggaagc    61080
tgaggcagag gaattgcttg agctcaggtg tttaaggcta tactgagcta tgattaagcc    61140
actgcactcc agcctgcgca acagagcaag actccatctc ttaagaaaac aaaataaaat    61200
acagtattga aggactaaaa cccacatata tggagggctg actattcttg ttatttttaa    61260
atatggaaaa cttttttattt tgccaaatta aatcttttat tttcaagctt acatttgaaa    61320
atgttagcat tgcatacata aaatgatttc attaaaaata tctaaaagta ggatggacat    61380
aaatctagaa caaagtatt ttaactgagt aaattcattt atgtggaaaa aatctcaaca    61440
agcatctttc ttttagcttt gatatattag aactttatc acagaatgat gctcactcta    61500
caagcttgaa tctgagaaac tcagatgtag ctaatgaaaa actaatgaaa aatataaagt    61560
aagagaatta tagaaactta aaaaaaaact gttacattcc atttggacta ctagccatgt    61620
gttccacaaa cattttctat tttatataat tgcctatctc attgtcttaa caacatgaag    61680
actaagatgt gaaggggga ttaagcatgt ggtaagagtt atactggggg aagctaaccc    61740
aagggagatc agatgtggct tcagattcca catacacagc tacatttcct cactgaggca    61800
gagcaagtta atccagaaag tcatatcagg ctccaagaac gctgtactta aaccattctg    61860
aaaatcactt gaaacgatat aatttttaagt aactttaga cttaaatctg gatcattata    61920
ccgagagatc aatttaattt gtttggtagt ttgttcattt tcaccctgtt aattccacag    61980
aggactcgtc atttacatta ggtatacctc ccaatgctat ccttcccccc tcaccccacc    62040
ccacgacagg ccctggtgtg tgatgttccc caccctgtgt ccaagtgttc tcattgttca    62100
attcccacct atgagtgaga taacgggtgc agcacaccaa catggcacat gtatacatgt    62160
gtaacaaacc tgcacgttgt gcacatgtac cctcgaactt aaaagtataa taataaaaaa    62220
aaattccaca aaggaggagg gccgactttt cacatacatg tgtcctcctt gcaggacttg    62280
agtatgcaca aattttggtg tagagggtgg tcctgaaacc aatccccgga gataactaaa    62340
ttcagttttg ttctgaaatt tttattttct gggtagaaac atattttcat gaagttataa    62400
ttatattcat tttctttctc agcccaatag tattaagaat gatgaatgat caactcatgt    62460
ttctggaaag agcatttatt gatccattag ggttaccaga caggcctttt tataggtaag    62520
aaaagaaaat atgactcctt tctgtaatat cacttttct tctaattatt tttattttt    62580 tcactgtgga aaaaatattg tagttgattt cttgcaagca aatagaaaat ttcaaaatat    62640
atgtagtaag tgatagttgt attgtttctt catataatgt aatatgattt ttgcatatct    62700 ttatttgag tatctttgtt ctgattataa agaatataa atttatttta gaaaatatag    62760
aagatccaga aagccatgac aaaaaataaa aatctcccca attttatcag aaaaatataa    62820
aatcattgtt atattctggt gtgtataatt ttagctcctt ttctatttta aatatatttt    62880
tacttatgta tacacagaac ccaaacatct ctctatatat aatgtatata ataaatatat    62940
atttatttat tcttttccct aatgttgata tttagatatt ttatttcctc ctaaatcctg    63000
acagttggat tttttttctgc caaacattga ctgtccccag gttgatcttc taaatattgc    63060
agaatgagat agatcattgg acagccagaa atggccctaa ctttctttct agggattatc    63120
aaagggtcgg gcttgggagt aagagcatct tccaagcagg ttgactggat cagatccacca    63180 gtagcagcat atttttatcc atccccccacc cccccttttt ttcctaagag acagggtccc    63240
```

```
actctgtctc ccaggctaga gttcagttgt gcaattttag ctcactgcag cctcagactt    63300
ttgggctcaa ccaatcttcc tgcagcagcc tccaaagaag ctaggactac agtcacatgc    63360
caccatgccc agctaatatt tgtacgttca tttgtagcga cagggtgtcc ctatgttgcg    63420
caggctcgtc tagaactcct ggcctcaagc aatcctccca ccttggcctc cctaatatat    63480
gggattacag gcatgagcta ctgcttctgg ccttatttac atctttacta tggagtttgt    63540
ccttctcttt ctgtgggcta ttacatgaac tgtcatagcc cattctataa aacatttttct   63600
gccttggtca catggaacat tacaaaattg ttttttgatga ttcttcaaac tctatattaa   63660
gtattctaac atggtagtgt gacttttttaa aaaagacaa aaaaaaacca caatagaggg    63720
ttggctgatc acaagcaaga ctgtaatgat tacaattgtg ctataatata gggggtagca    63780
tgatatatta aaaaatcagc agttacttgt cgtgtgcctt gagacaaatc atttagttac    63840
ttgatctctc agacctcagt ttccttctct gtgaaatact aatatcaact gtgtagagtt    63900
tatttctaaa catcagaaaa attgcaagta aacattaaat accaagaatg attgctgtgg    63960
ttactatcat cattgttagt tttgtagcac tgaaccactt taatttatttt gtttgaaata    64020
aaaatataat taattactat agatttcata taatagtctt cagagatgat tgaacttgga    64080
agttcagttg acaggtggct tgttcaaatt gttataggaa tatgcaatcc aggaattgca    64140
gagtgctctt gtgtttctct tgtatatcat ttgggcacct aataaacagc aaacgatttt    64200
atcaacaggc atgtcatcta tgctccaagc agccacaaca agtatgcagg ggagtcattc    64260
ccaggaattt atgatgctct gtttgatatt gaaagcaaag tggacccttc caaggcctgg    64320
ggagaagtga agagacagat ttatgttgca gccttcacag tgcaggcagc tgcagagact    64380
ttgagtgaag tagcctaaga ggatttttta gagaatccgt attgaatttg tgtggtatgt    64440
cactcagaaa gaatcgtaat gggtatattg ataaattta aaattggtat atttgaaata    64500
aagttgaata ttatatatag ttatgtgagt gtttatatat gtgtgtgttt atattgttta    64560
tcttctccct atggattaaa actgaatttc ataattataa gaggttattc tgaagtggaa    64620
aaatttaact cagtattaaa tctaaggaga atggcctaat atagtaaaac tctcatctgg    64680
cattatcagg gaatcaagtc taatctattc atgtcacttc acacagaaga aaacatcagt    64740
atgtcagaga gcacactggg gaatatgcac aagattatcc caagccagag gcctcacggc    64800
ctacctggcc agcctgggct gagaggatca ctatctcagc acactatttg ggaaatggat    64860
caaatcacac ttttagtaaa tgttatcact ctatagcata agaaataatt atttttttatt   64920
tatataaaag gctatagtat aaaatatatg tatagtaatt aaatgaacac ttgtgaacct    64980
aatagccata tgaagaaaat aacatttcta atatctttgg atgccccatg tactaatgac    65040
agttatgctt ttgcattttc ttgaatttta tgtttattta tctttcctct gtcattattt    65100
ataatttat cacacatggc tgtatccttt acatgttttg gcattatgta tttttgaact    65160
ttttgtaaag acaatcatac catgtgtaat tttcaggac ttgattttttt tcattgactt    65220
ttaagggttc aaatatatta tcactgtggc tgtagtttgc catattttgc tgatatagag    65280
cattcattca catgagggta ggattcaggg tccatttcat ttaattatca tgacttatcc    65340
tgaaataatt taaaatctct aacaggtgat tatgtaaacc acactagatt tttctgttgc    65400
accctgtatt attatttacc tttttacagat aagaaaactg aggtttaaag aaattgatta    65460
agttttgcgg agcgctaagg agttaaaaga aaaatgaaaa atgggcttag ctggcaggaa    65520
cagaaacagg ggtagagggg aatgaatgtt ccaagaatag ggtcaactgc aaatggctca    65580
cttagcaccc aagcatcctc ttacaagcac ccagctcaca gcccatctgt aaccaagcat    65640
```

```
cctgtctgca agcattcagc ctaaggagca cccttataaa actccctcga gtccctgcct    65700
cttttgcagac agccttccct ctgctgtctg gccagttgct cccttgcaat gtgtctcccc    65760
ttttctctaa ataaatatgc ctttctaaac tcattactgt cttggtatta aggtaaattc    65820
ttttactacc tgcacgtcag cctcacagtt gttgaccatg acaactttct caagaaaaca    65880
atgggcagat gtttgttttc tgaatcccac cgataagcat taggccatac tatacttcct    65940
tctttaacta ttggaaaaag attgaaggtg actcttcatg tcagaatttg tagaaacaaa    66000
catgaactaa atcaaagtat tatactcatc tatgaggtgt gttctagaaa aaaattaaaa    66060
tatttttaat tcctcttatt tccagccttt tacccatatt tgcctttgaa aaatacttag    66120
tcaagaaaaa tcactggctg ctttctttct ttctttcttt ctttcttttct ttctttcttt    66180
ctttctttct ttatttattt atttattgtc aaagtctggc tttgtcacct caaaccgctg    66240
ggctcaagca atcctcccac ctcagcctgc caagtagcag aagctacaaa caccagccac    66300
catgccttac tcattttaaa aaaaattttg tagagacagg tcttgccat gttgcccagg    66360
ctgatcgtga actggccaca agcaatcctc ttgtctcagg ctcccaaagc cctgggaata    66420
aatacatgag ccactatgcc cagcctcctt ggctacttct taatctgtag acatagcatt    66480
cttggacttt aaactgcatg ctgaataaca gagctctaga agataaaaat tctaacttat    66540
ttctccaagt aatttgattt tttaaaattt cagtcttttt aaattggggg tggttacata    66600
ggcatttata tttgttgaat tctttttgtc atatgttaaa aatatgtgca ctttattgta    66660
tttaaagtat aaatttttaaa tttgatataa acaaaaagat agggcatag ataaataaga    66720
atgttcccta atggttcatc tgaattccat tgtttcaaag taattaattc tcattctcct    66780
tatgctaact ttacctaaag taggggaata tttgcagagg gaactttgta gacagatttc    66840
tttgcttcgg aattttgaaa aatagaaaat gtggtaatac tgtctccaat gtaatgatga    66900
aatggagtag taaatgaaca tatttttagga aaaaatgctt gtaatattta aataaaatat    66960
atattttttcc tctgctaatt tttattacta aaataaaatg ctttttttttt ttttttttgtg    67020
agatggagtc ttgctctgtt gcccagcctg gagtgcagtg gcacgatttc ggctcactgc    67080
aacctccacc tccccggttc aagatattct gctgcctagc ctcctgagta gcagggacta    67140
caggtgtgtg ccaccatgcc cagctaattt ttgtattttt agtagaggca gagtttcatg    67200
ttagccagga tggtctcgat ctcttgacct cctttatctgc ctgtctcggc ctcccaaagt    67260
gctggaataa caggcgtgag ccaccgcgcc tggccaaaat gcttattttt atacagaagt    67320
ataaaagta ggaagcttaa gtaccatttt ataaccctct gtcctttccc ttaacatatc    67380
accatccaga gatgaatacc gtcaacattt tggtagtaat tatttgagac attttttcttc    67440
aaatacacac aatacttcga atgaaaaatg aaatcatgct atgcctttat ttttaagaaa    67500
acttttaatt aacatataca tacataaaat gtacaagtct taagtgtaca gcttgatgag    67560
tttttacaaa atgaacacac tggtcattca gcatcaagat caagagacag ggtatcaaca    67620
aaactccaca agccctcatc acatcccctt tacatcacta tctttcatgc tgacggatat    67680
ccactattct cctgttctaa attctaaata atgtctagtt ttgctgtttt gaaatttctg    67740
taattggaat cacgtagtac ttgtattttt gtgtttggct tgtttcccta ggaactatgc    67800
ttgtgaaata cattagtagt gtgctagtaa atcagctcta aagaagggg aaagccttgg    67860
tttgcagcat ttactgattt ctgtgatgca aatattccca accatggcag atatcaagga    67920
aacaacaaga agttactgaa tgtgcagtct gaaagggaag gccacaattg ccttttgtaa    67980
```

```
gctggcagaa gcaggctgca gcacaccact ggacactccc tgtctttcca tgtagcaata   68040
gttcattcat tttcagtgtt gtagatttat cagttgtata aatgtttcac aatttattta   68100
tctattctct ccttagtaga ttttagatt ttctccagtt cttggctatt agaaattgta    68160
cttcagtgaa cttcttgtg catatctttt ggaggtcata tgtatgtatt tttgtgggta    68220
tttatctaga agtcataggt atgtatatgt tcagctttag tagaaacttt tagagttttc   68280
taaggttttt atgtactatt cataccagaa gagtatgtgg aattccagtt tctctctgtt   68340
cttgccaacc aactggtatt ttactgatga caactaaaat ggagcagctt tcatgtggt    68400 tgcttctaat ttgtactctt ctttttttgc actgaccaag tgttttgtcc cattttcgct   68460
tgggtattct gccttttct ttttatttg taggagtttt tgtatatatt atgactataa     68520
ttttataatt tattttattc aataatgcag aattttacat gagcatataa aagatctatc   68580
ttatcatttt gtcactttat agtatttata aaatatattt ataatatttt aagaataga    68640 cataaaatga ggtatttcat tttattcat atcaaaattc ttatcaaata agtgatttac    68700
aaacatttca tttgacattc tagttgtctt ttcactttct tggtaatatc acatgagtac   68760
ttaaaacaaa ttttttacg tgtacctgat tcacatgaga atttaataga tgctcccta    68820 cttacaatga tttggcttag gattttcaa ctttatgatg ctgcataagt gatatacatt    68880
cagcaaaaac catacttcaa gtactcatac aatcattttg cttttcgctt ttgaacagt    68940 attcaataca ttacatgaga tactcaacac tttataacaa aataggcttt gtattagatg   69000 attttttttca actgttggct aatgtaagtg ttctgggatg tttaacttag gcgaggctaa   69060
gttataatgt tcaataggtt aggtatatga atcatacata cctgatttta aatttatctc   69120
agtcagtaac tcgcatatgc aaatatgggc aaattgttcc atttttgcctc atttgtaatc  69180 tttaccattc ccagaaaagg ctcttctcaa agttaccaat ggtctaggtc tttcaaagg    69240 cagtgatcag tttttttgatt ctgttttgtt tgtgtgtgtg tgtcagtgga acaactgaac   69300
catgtgacgt ggtatagcca taagaattct ttagacccat aagaacatct gttcttacca   69360
aacaggaaaa acatgacaaa ggtgtaggtt tccatcaaga tcagaggtat tttgacctat   69420
gtaagaagat attttaaata atataaaagc caaagaaaat taaatccagt gatataaccc   69480 tgagtggtt tgcagaattc tgtgggaaaa aaatattata ggtgaaatcc aaactgaaac    69540
atgttatgta cctgaaccat aagattgcaa gaccatttag tgagttgata tggtgactac   69600
agataagact gaaatatgttc tatcacagta acagatatca gagtccctgg tcaatatctt  69660
aggcgaatat gcatattcca accatctagg ggagtatcct caaagacttt gtggtaacac   69720 tgttgttttcc tttgtgggaa agcctacttt tacccttaaa atatttaaag taaacataga  69780
aatatttagg taattaaacc cattagttaa aataagttta agcatattta gtatttcaaa   69840
attgtgatgc gtactgttca gaagaatatt gactattcaa tgaacttttt ttttaatgta   69900
agctgtataa attgagtagt tgagttcacc ttttgagttt taaattcaaa gtacttacgg   69960
tatttatatg cactgtgact ggaatatgga aaagaagtta aaatcgggcc aggcacactg   70020
gctcactcct acgatcctag cactttggga ggctgaggtg gcagattgc ttgagctcag    70080 gagttccaga ccagcctggg cagcatggtg aaaccctatc tctacaaaaa atagaaacat   70140
tatctgggtg tggtggcttg cgcctatagt cccagctact ggggaggctg aggtgagagg   70200
atagctcaca cctggaaggt tggagctgca gtaagcctga gtgcaagcca ccgcactcca   70260
gcctgggtga cagagtgaga ccctgtctca aaaaaaaaa aaaaagaaa aagaagtta     70320 agattactca taattataaa ttaaatatat tagacttaca aaaattaatt ttaagtactt   70380
```

```
agaaatgttt gttggacaga ccattgaagt acctaaaata ttaatagaat acatttataa    70440
atgttattta aaatgcttaa cagtatttaa ttaactatgt aaaataagac gaagactatg    70500
agatatcctg taagttattg ttaaaattta ttagatttct aaatagagta agatatgccg    70560
agaccagctt ggtctgggag accctaaccc agcggcgcta gaggaattaa agatacacac    70620
acagaaacat agaggtgtga agtgggaaat caggggtctc acagccttca gagctgagag    70680
ccctgaacag agatttaccc acatatctat taacagcaag ccagtcatta gcattgtttc    70740
tatagatatt aactaaaagt atcccttatg ggaaatgaag ggacgggcca aattaaagga    70800
ataggttggg ctagttaact gcagcaggag catattctta aggcacagat cgctcatgct    70860
tttgtttgtg gcttaagaat gactttaagt ggttttccac cctgggcagg ccaggtgttc    70920
cttgccctca ttcctgtaaa cccacaacct tccagcttgg gcgttagggc cattatgaac    70980
atgttacagt gctgcagaga ttttgtttat ggccagtttt ggggccagtt tatggccaga    71040
tttttggggg cctgctccca acaaagatat atatatatat atatatatgg aatatcaaga    71100
agctaaagaa caggggttttt ttaaatgtag cttcaatcag ttaaatattg attataaaaa    71160
ttaaagtaaa actctgaaga gttttctgtg tataaacctg tcctcaagga tataaaaaaa    71220
ccgtcagtgc agacactcag agagtttaac aaagttaatt gctaattcct tcattaacac    71280
tttctcttct agactgtatg acaccattgt cctctgaaac tgactggcgt cccttctcag    71340
tctcctttgc cagccctgcc ttttttacca gacctttaaa tgttggagtg ttccagggct    71400
ctccctttgg ccctgctctt ttcattctat agtgtctctt gaggtgattt caaactccaa    71460
gtaccatcta tatctggcca caactggcta gagttcacca aacacatttc cctattgttc    71520
tgggaataca gctaggccgc atgtctcagt ctcccttaaa ggtaggggtg tcctcattat    71580
tgtgtaagaa ctaataacat atgagaggaa gtgatgtatg tcccttccaa gcttatcccc    71640
ctccaaaagc ctcctataca attttcccct ctctttgttt accctaatgg tttctgaaac    71700
acacagaggc tctagcagag gatgcagagg ccctggagaa tgatacagcc agacagaaag    71760
agcctagatt actgaaccat tgctaggagc gatcaataac acccaaataa actttatagc    71820
aataaaagaa taaattattt ttttaactga atggattgat ttggtacaga agctggtgca    71880
ctaaacactt ctgatcttga ctgagacctg cattttttc gtatttgttg tccacttaga    71940
cttctccctt gagattcagc attaaatatg taattactta attgaggtct ccaactggaa    72000
gtctattagc tcaagcttca catagtgaaa gataagttgc tctacaaccc actgcccaac    72060
aaatttactt tgtgcctccc caataccaac ccaacctatt gccagacttc cctccctgtc    72120
gtacctgaat aaatgatgac accactcttc acagcagttc aggctaaaat cctgtcactc    72180
ttgactattt tactcataac cagcagctac ctctacttag tcctaaaagg gaaaaaaagt    72240
catcttttcc ttgtaaacct ttacctttac tctattttc tctgctaaac aaagtttaaa    72300
cttttttatca agatgtacaa atctttgcaa aatctcatac aaatctagtc ttgcgatgaa    72360
cttctacctt gaaaacctca tgcccctggt cactgtgaaa tggatgaaga gtagatatct    72420
gactcagctt tggagaatat ttttgccaag gtgttgaatt caagtttaaa gtgactggaa    72480
gcattacatg agtggctagc tagcttctac ctcacatatg aattgactaa caaagaaagc    72540
aggattaact agaaagcaga ataaagcaag tgcccagaga ggagcagaaa caatattaga    72600
aatggagcac tccttcaatt tataatctcc aagatcttga ttactgcatt tcctgagacc    72660
cattgtcatt tctacatttg gcttctgtga gacattcttg tgtctttata ataagcccct    72720
```

-continued

| | | | | |
|---|---|---|---|---|
| accaccatta | ctccctctct | tttttgctta | agctaactgg | aattggttta ttttatctac 72780 |
| cgtatagaat | cctgaataat | taagctttcc | agcctcatct | ctaattcact agtactcccc 72840 |
| gattcccttc | tgccatcaca | tatgaaaact | ggatacattg | aacttcaaat ggtttctaga 72900 |
| atattgttgg | ctattttgtg | atattaggat | ttaaaaaaat | ctgtctcatt tgcttgtgat 72960 |
| attcgctgcc | acttagcttt | ctggaaatgt | tttagtcatg | cattagggct cgtctcaaat 73020 |
| atcacccttg | cattggactt | atttggacct | tctgcaggaa | gatattttta ttccatcttt 73080 |
| tgtgctgtca | tagtactcta | tctacccatc | tgtaatgaca | tgaaggacat gaaatcatta 73140 |
| ttgaaagatt | ttcttcctca | ttagactgac | gcaaaggcag | gaatgatgcc caattaattc 73200 |
| tgaatgcctc | aagtatacta | cacgatttga | cctacagttg | tatgtctatt tgtcaaatga 73260 |
| aggaagaaat | acatgaaaga | agaaactgtg | ctagccctgc | caattattat tttagcagat 73320 |
| atcttatttt | aattgtttaa | gtttcaaatg | atctttgtgg | tatactggct tatttgttta 73380 |
| gtttatttct | cagcacattc | tttgcatatt | ttattaccca | tcagcaataa aagacaagaa 73440 |
| gggaaagaag | gaattgtaat | aatcagctct | tcacaccctt | atttctcttc cctaatattt 73500 |
| ccccaagttt | ttattttgtt | ctcacaatta | agtctatact | acttagaaaa taagattaaa 73560 |
| tcttctatgc | tcctttggtt | agaaattttt | ctgggatgga | tttaaagttg aacatctatt 73620 |
| gcaacttaaa | atttttgtta | aagttgctct | ttctttctaa | tagcaattat gttgggctag 73680 |
| aggataaata | gttggagata | acggaatttt | ctcttagtgt | tattgctgcc tccattcttc 73740 |
| tatatcttgt | aatggactct | ttggagatta | taataataat | gaatactagc ttaatattta 73800 |
| tcaaccacag | agccggggc | tgagccaagt | ggttttatat | acattgcctt atttactcct 73860 |
| tttctcagca | ctgtgactat | agtactttca | taatacgtat | aactttagag gtattttgag 73920 |
| ttactaagaa | ataacatgaa | aacaagctct | ttgagcctgt | aagattacta gctaggacag 73980 |
| ctttgtaaga | gaaagacctc | tttacccttc | aggagtagca | ggaaaagtat gctattcaac 74040 |
| aggattggct | tatccacctg | actctgacat | aatcatatat | gaaatgatac tgatatcagc 74100 |
| tttctttctc | caattgttga | taatttggtt | cattatttct | tgtccttcct catgagtaat 74160 |
| ttgatctgtc | ctgttccagt | tcttcccttc | cagagcagga | aagtcaaagg aaaggaggaa 74220 |
| gttgtgtaga | agaaaagttt | caaggggcat | tctccggaaa | gactgaaaca ttatgctaac 74280 |
| cagtcaaaac | atatttgag | aagttaaatt | tggattagaa | gtctctttct ataatttttt 74340 |
| tttcaatttt | taaaaatttt | tatctttaaa | aaatgtgttt | ttcaaatttt atcaaaaagc 74400 |
| tcgagctttg | tcctagctga | gctcacagga | aaaggaatgt | tttcagatct cagatctgaa 74460 |
| taagtggggg | aacagcttat | ctctgagggg | gcaagctggt | aagagggtcc catttgaaaa 74520 |
| actcagaaac | aagaaaggat | tttaagtggg | aaccaggagt | ttctcttcaa aataatcctt 74580 |
| tacactctgt | tcattaaaat | atatatatat | tttatatat | tatatattta aatatatatt 74640 |
| tatttaaaaa | tatattatat | tatatataaa | atatatatta | tattttatat acatatatta 74700 |
| tattgtatat | ataaaatata | tattatatt | tatatacata | tatattatat tgtatatata 74760 |
| aaatatatat | ttaaaatatt | atatatatat | atgaatttaa | aaagtagtcc tttcacaagg 74820 |
| tctaaggatt | tctccactgc | tgataatcac | aagagaacaa | actgagtctc tagataggga 74880 |
| gaaagtgaga | gttgcaacat | agttccagac | tccagaagaa | aagggttcac gtgccacgga 74940 |
| ttgccaagat | atcctgtgat | aacttagctt | ctgcttagag | tgcttaggcc tatatctcct 75000 |
| atctactatt | ttctctatt | cttgggaaag | ctgtctgatt | ccatctgtgt ttctatctgg 75060 |
| atatttagca | cttatcacca | ttttattata | ttattatata | ttattcaact ggattttgtg 75120 |

```
gtttaagaga atgttgggct aggaatcaga ccagtggttt aatgcactga aaagacataa    75180
taatgttata ataactaaca cttattgctt atttgctctg tgttgggact atgcttaatg    75240
ctttacatgg aatgttgaga attactgaag tgttcagtga gcaacaaact atgaaggtag    75300
atctatgtga taaaaattta gtttggtaac agaataaaat atgtaaaaag aagttatctg    75360
tggtgtatgt gggatcattg gtgtgctttg tccttagaca taagtgtagg aggggggcatt   75420 tcagatgaat gttgctattt ctacaagtca agccaagtaa ttcaatagaa taaaatttg     75480 ccattattaa ttattattac tattaatttt gtcaagcctg gcagctata tgtcatacct     75540 tcagtaaaaa ggaatatcca tagcctagac attgaaacta atatatttat tgttccagat    75600
gctaacacag ctgagtgatg cccttcattc aggagctcct ggggaacaca gtgctatata    75660
atacagtgaa atgggaatca gtgagaagag gaaaaataac ttcatcagga atgtgaatcc    75720
aagattctta aaagggcaga gtactttct cattcattgt ttttttttt acctccattc       75780 aattaaagag acttggggtc atcgatgttt cttttctctt ccatttcatt tttgacttaa    75840
tacacaaatg gagtatgtta ttgacagagg gtcccccttg tggtccagcg taaactccgt    75900
cattcaatca aaactgcaca ccaaaaacct atatgattca taagcaagtg cataggtgt     75960 ttgcgctacg tcatatttca acaggtagca tacctccaat ttatttgttt atttttgagt    76020
ttcttagttt gtatttgcat tttctgggta ctagattcct gacaagaatc aggtaaggct    76080
gtcatagccc aatatatgga gttctataac tcagcacttt aaagaaaata gtcctcagga    76140
ctttaaaaaa gttttttaaaa acttttttaaa aaagttttta aaaggcaaat taaataatta    76200
tttgtattta aaaaaaatct ttgtgctttt aaaatgctat taatttaaac atgattatgg    76260
acaatagatt gctagtgatg aatgatgggg ttttggacgc gccagacatt gtacagcttc    76320
tcttggggca agcatggtga tcgatgtggg tttcgcaagc tggagtcatt caacttggtg    76380
ttctagtctt gtatatatac ttaatttcat atttaaattg tacaattatg ttattttgac    76440
tatagtcaac ctgttgtgct attaaatact agatattatt tattctttct aactattttt    76500
tgtacccaat aaccatcccc acctcaccct caaagcctac actaccctt gcagcctatg      76560 gtaactatcc ttctgctctc tacctccatg cgttctattg ttttgatttt tacatcccac    76620
aaataaatga gaacatgaaa tgtttgtctt tctgtgcctg gattatttca cctaaaataa    76680
aatgtttgtc tttcacctaa aataataaaa tgtttgtctt tctgtgcctg gattatttct    76740
cctcaaataa tgatctccag gtccattcat gttgttgcaa atttttttca tgtgtcttta    76800
ccacctgttc tggtaccata cccatctgtg ttcaattttt tttgtactga aaagtatata    76860 tatatctc caattccctg tgataccgag gaaagacagc atacacacac acacacacac       76920
acacatatgt atatgtatat atatacatat gcatatacag ctactgagtg acaagtggta    76980
tggtataata tcacctgtca ctcagtagct atcatatata tatatataaa acaaggaatt    77040
gtttccagga acccccaaaga tactgaaatc tgaggacgct cagctcaagt cccttatgta    77100
aaatggcata gttatattgt ttctctgact tttggctaag atgaagttta gtatctgttc    77160
ttatcagttt aaagtggcat agtatttgca tatagcctat gcatcctcta tacattaagt    77220
aatctctaga ttacttatac tacttaatac aacacacatg ctatgtaaat agttgttata    77280 ctatatttt tatttgtatt attttttatt attgtattgt tatatttaa tgtttgttat       77340 ttccaaacgt ttttaattca tggttggttg aatctgtgaa tgcaaaatcc acggatatgg    77400
agggtcgaat gtacacacac acacacacac acattcataa ttttcaaagt ccacagtaag    77460
```

-continued

```
tatcaagcag tgtgtgttta cctgcatgtg taggtgaatt aactctgttc ctgaggcggt    77520
tttatttccc tccaatggat tctactttat ttcttaatgt caagaaatgg cttatctcta    77580
tctgagtacc tgtacttcct ttctctgtct ctctctgctg tttctgtctc tgtctctgtc    77640
tctatcttag tgtttgtgtg ggtgagagat caccattctg cctgcaccac tcaaaatgca    77700
gctctcctaa ctaaaagatt gtattattca cggaggtctc aaacgaaaat gtttctccca    77760
ttggacagaa atgagaatgc cctggcaacc atattaggga aacatgataa tttaccacat    77820
cctctctgta ttcttgttca tttattttc attctgtcgt actctgtacc tttttatagg    77880
ccacttcaat ttgttttta ctagagctgg aaacatgtta cttctcctat gaaccagcca    77940
agttttatg tgcttattat ggattcaaca taccctctt ctcaattcac aacaaatggc    78000
tcctctctat ctgagataga gcaagttgaa gtcctatccc tccagtactg tactttacaa    78060
tgtgaaggct tgggacagat tctcctccac agcccccaga gggaacctat cccactgaca    78120
ccttaatttt atacttctag catctataac tgtgagacaa caattttttg ttgttttcag    78180
ccactaagtt tgaggtgatt tgttctggca gtcctaggaa actaatacaa tgcctctatt    78240
aaaacaattc atcttgttta ctccagtgtt tttttttttt ggcgtatctg tttcagactg    78300
gactatgtac tcatcaagag aaatgacctt atctgtcata tacttcactc tgtggtattt    78360
atgtaaggga tataaaatgt aagacatgat atgctatgta agatatgata cctgccttaa    78420
aatccagtgt ttattcatca aattgttact gagtgcctga tgtaattatg taacagccac    78480
tcctcaggat actggtctta caacggtgag cacagagatg atggtctcct ctctcgtgga    78540
gcaaacagtc tggaaaatgg tggggtgggg ggacattaaa aacacaaaca aaagaaaat    78600
aattgcacaa aaataattgt caagcaggag aaaacatct gtatgtaaag aagaggaagc    78660
agcgatcatt cttggccatg ggatgatctg gaaaggcttc taaaaggggc agtagatttt    78720
aataaacagc acacacagag agactatttc cttgtgaaga agagaatggg gaaggacccc    78780
tgggtcatta gtagttcatt tgcctggagc atagagaaat agagtaagta gagtaatcat    78840
ggcaatagtt ttttgggtgt ttttaaaatg cttactaagt atcagcctta cattatctca    78900
tttaccttca cattttttg acgtaggctg ttgtcatccc aatttacaga taaggttgtt    78960
gagttttcct taatcgtagc tttatactta ttattatacc ataccacctg tcactcagat    79020
ttattcctag ggataactat aatttgaaat gagatctctg actccacagg ctctgtcttt    79080
ttttcattcc acaacagaga attattccct aaaatgcaga gtcagaaaga taggttgcag    79140
gcagatttta gaatacttct attactaatc aaagactata aaaatatact ttacagtaaa    79200
caaaggagaa aatcaaatgt ctgcaaagta gtaacatgat atacatgcta aaacattgaa    79260
ataggaaaaa atattggggg aagtaggatt ccttagcact tactgaagga aagatccaga    79320
taagaaatgt aaatgtacca ggcttggtgg ctcacacctg taatccctgc actttgggag    79380
gccgcagctg gtagatcact tgaggccagg aatttgacac cagcagggcc aacatggtga    79440
aatcccatct gtattaaaaa tataaaaatt agccaggcct agttacatgc acctgtaatc    79500
ccagctactc aggaggctga ggcaggagaa tcgtttgaac ccgggaggtg gaggttgcag    79560
tgagccgaga ttgtgccact gcacttcagc ctggtcgaca aagtaagact ctgtctcaaa    79620
aacacacaca cacaaaaagc aaaacaagtt atgtaaatcc atcatcagaa tgacttagtg    79680
tgaacaagaa gcatctgagt tgtctgctaa aaattcctgc ttcttcgcaa tgagaatatt    79740
caaaaatctc gcttcaaggt ggtggataaa ttacctcaat ttggtcatta cacaatgcac    79800
ccatttaaac acacatcgaa acatcaggtt gtaccctata agtatgcaca attattatgt    79860
```

```
gtcaattata tttttgttta aattctactt ccagtcacca ctccagagga ctgctgacgt   79920
gaggaggttt tagacaatat tctgttctgg cctagccaag ggattaggga ggcaatgtaa   79980
gccaaacttc ctttttcaca gcaagctctt ggactgcagg gatcaaattt cattcaactt   80040
tttattccct tttcccctag gtcccagacc cttgctcata ataagcatgt ggatgactcg   80100
aattgaatta taagagtgaa agactcttgt gaaagaagaa tcattaagac tgtgtgaatt   80160
taaaagaga acgaattcaa gagaacatgc tttgtaagtc tgggaaagag aacgtgcacg    80220
gtacaagggc ggtaacatgt gaccaagaag agaagagtaa aatgaactca ctagccaatt   80280
acattcgagt gatctgctac ttagaatgca tgattgaact cctaggtggt cttatagcca   80340
ctgcgtactt ttcctctgcc agactttgaa agcactttga agacagggtg tcatctaaag   80400
gttggtgatt tgtattgagt tcccccaccc tagaactggc aggcaccatt ctctctgata   80460
aatatcacag gaagaaatca gagaattgta ttttcctttg aaatagttgg aagatatata   80520
gaaaagccta atgtggtttt ctcagttgga aattttccag gacataagga tgtgaatgcc   80580
catcttctca aaagacatgc tgtagatgcc aacagatctg agcagcagga tggaatgtat   80640
cgaaataaat ggcaggatta tccagtgctg gagcccttat ttaagaagcc catattaatt   80700
gagctgaata tagttggcat tccaacaaat atatgctgaa aggaaaatag caaaacaaac   80760
ttaggggata tgttctctca cgtggttgat aatttgtttc ctaacattct gtcactgaac   80820
ctggctggat atgaaaagt ccattctact tcattctac ttcagctact cagatcttag     80880
ttgtacccta gaacttttca tgatggataa ttgtaccctt ctatactttt catttaaacc   80940
atgtcactca ccaataatta cctatcattt tcagctaatt gcctctagtg ccttggctcc   81000
aaacattctt tgacccaact gtatttacac ttttcctcat tcctttatac ccctaaaatt   81060
tgcagtcccc ttcttactta gctaatattt tacaatctct cccacaaaca ccctcaaatg   81120
gctttgcatc tctcttcttc attgtgttac ttttgtaaaa tccagaccct atttaaatac   81180
aatgttccat gtattctgtg cctgaaccta tgcagctgat gtagctgaag caaagcaggg   81240
gtattggctg gcctcacttt aaattcttca tccttaattg gaaatgtatc ttcatactcc   81300
ctggtaatcc tactttatat attttttacac ctattacttt tcctgaactt ccaatactgc  81360
ctcgctcctc ttcatttttgg tttatgaacc tggcttccta tttcactggg gaaatagaag   81420
taatcagtaa taactcgcac gtcttttcac caccacatcg accagcccat cctatctgta   81480
catgtttatt gtctcttcct tcctttctta cttgagctgt acatgctcct atctgatcac   81540
acctatgcac agggtctcat tctctttcac ttcagcaatt agactcttcc ttaaaaaata   81600
attttctgtc tcaacttgat tattcccaca atagtgcaaa catgttgtaa tatctttttt   81660
ctttaaaata acccatttc tttaaaataa tttccaacta tcaactgatt cctctgtttc    81720
tctctctata aaattcctta aaagagattt cttatgttgc ttctctccct tttctctctt   81780
cccattctca tttgaatcta cttcaaaagg tttactatac taanaaaaca agctcttctc   81840
aagattacct atggtttcca tagtgctaaa ttcagtgata aatttagtct ttgtcttaat   81900
cagcctctcg gtatctttga ttcagagggt aattctctcc ttcttgaaat actttcttca   81960
cttgacttct gggagctact cctcagtttt cctattcact ttagatgttc ccctaagctc   82020
tgtttactca tttatctcat ccctccactg gagttcacta gggttcagtc cttagatcct   82080
ttctctatca gcattcactc acaaggtgat atcacatagc ctttgaatag tatctgaata   82140
ttgatgatgg tcaaatgtta tttcccttga actcgagatt ctattcaact cctactaaac   82200
```

```
atccttacct gaacaattaa tagacacatc aaatttaata tatcctaagt tggactcttg    82260
atgtcctgct cttccaaacc tggtcctctt gcacattttc tatctcatta aatgtctatt    82320
tcttcccatt gcctaagcaa ttcagagtca ctctcgaagt gacttttcta atttccccat    82380
gcatatttga tcgatcagtc gtgttaatta tgccttttaa atgtgtcaag aatctaatta    82440
ctcctcttcc actgctaact tttcttgaaa tgaccatcag ctgtctcttg gataaatacg    82500
atgctttact tttggtattt ctgattcagc atttgcttcc ttattatccg ttctgaacat    82560
agcatctggg ttagaggtct tgtcacctct gtgtcccaaa gtctacagtg attcccacca    82620
ccctccttat caaggctaac aaggcccctac atgatctggt ccccacttct tttcagacct    82680
aatttcttct acttttttca ggcttcactc attagccaca ctgtcctcct tggtgtgctt    82740
ccactcttag cacattccca gcaaaggcct tttgttctga ttgtccctct tcttggagct    82800
ctcttcctta aatatctgca aaatatctgc ttatctttt ccatcacatc cttcaggcct    82860
ttcctcaaat gccaatttct cagggaggtt ttccctggca accgtatcta agattacgct    82920
ttcctacccc agcactatca aacccccatcc ctgcacagtt ctcttcctat ttacagccat    82980
ctaacctact acatatgtga catatctatg tattgactgt tttcccctct agaatgtatg    83040
tacaatgagg gcatggattt tgttcactgt ttcatttcca gcaccgtaaa gagaacctga    83100
tatatagaag accctatata agtaacaatt gaatacttaa aggcaggcaa ctctagggtt    83160
tcttccccag acctctgtac cagaaattga aataggaaat agaagatatt gaggatacta    83220
ggtattctct acctgtgtta ttgaccagaa gcagcaacat ataattttc tttgcaagga    83280
ctaagctaat caataacgaa gcaatgtcac tgaaaatcac actcatggaa tgaattttaa    83340
taaaaatata tttttggatg cttttttgtta tatttgagag aatgaattga gaattttttgt    83400
tttttttta gtcaggtgga ctcctaataa cttttaaagg ctaagttaaa aaggtctcat    83460
tttctctaaa gcatttctga cttaccagtc agtcagtcac tctttcctca gcacattta    83520
tgtgtgtctt aactctagct cttatcacat tatttcatag tttgctgtat tgggttaatt    83580
ccacaactag gctttgtgtc cgaggagct acaactgctt ctgtcacata gtaggttctc    83640
ataaatcttt gttgaatagc ttatgtagac tcagatgcca caagattggc aataattcac    83700
tgttattaca aaagagaat taatataaaa catcaccttg tttgtagata tattaaagaa    83760
gaaggggaacc atgaaacaca atcttaagga attacaatgt gtcctctaag ttttggattt    83820
aattgtccta cctaaatctt aacaaacaaa agcacattga tactttattt ttcttcttct    83880
tatgttttgt attaccctga cttagtcacc agatgtcact atgagactgt tgtccaggtc    83940
actctttctt taaacaagaa ggaaacaaag aactcacatg aggcaaaacc tatggagcaa    84000
aaacacatgg agcaaaacct atgtccttgc ggaaacacct tataaatgtt aaggctagta    84060
gctttagggt tttatttag agtggatttt ggcatggctt agtgtgtaag aaagagcgct    84120
ggactgggaa ttgagactcc tgtattttag ccccaattct gtcatttaa aatatttgac    84180
cacctggtag atttctttac ctttctgggc tgtgaaagat atcctcatct gaaataagg    84240
gtggccaaag aacctcacaa tcttcaagct ctaacatcca gtgattctat tcccttcttt    84300
tgctaatttc ttggaaagta gccagaagac tttactacca gggatgattt ggaaagtcag    84360
cataagtgag aataatgaat acctattgca tactctattt tattctaaac acagtctctg    84420
ctaggctttg acctaccatg aagtggggaa acctttatgg tcactctcac ttctacacag    84480
tctctgtata ttggtggtac acattgtgtg aaataccttc tccatctaga gattgcttca    84540
ttttttttatt ataaaaacat tacacaacat ttgtttaagg tgtcatgtaa atatactttt    84600
```

-continued

```
agtgactgtc attttggggg tttcactctc agaggaaaat gaattatttta tattaggtat    84660 ttctgaatac ctaatctgaa tatgcttgct tttttaaaaa aaccagttct ctgcaatgtt    84720
cacccatcca cctacctaaa atatgcacca cttaatcttt tattcatgct gctccacagc    84780
gtgccgtaat cataacccac ttgtggtaga ctcagacact gttgttgtat gaatgcctca    84840
tttatctctt tctgtgcata tttatgtttc agttagctat tttcattgca tgtagttcct    84900
tccatagtgt gggttcttgt attctcagcc attttctttg tcattatttt actcagagtc    84960
gaaccacaga gtaaatattt ttgagaacag tctgaattat atggagcctt taacacttag    85020
aggcactatc ctaataccca aattattata tagaacaagt tgacacgtgt ttttatagaa    85080
ttatctaatc ctgaaacata tcttgagtat ttactaaatg ctccacactg ttgatgttct    85140
gggattgaaa caacagataa cacagtgtgg cacagagaga gcaggaacaa gcatttacac    85200
agcaaagtgg tgaccgttac agtggagttg tgtgcaacac actgtgggag gctagaggaa    85260
ggcagccagg cttcacagag gatggtatag acttaccctt gagctgacct tcaaaaatag    85320
tcaggaaggt ttgcatggga ggttgggagt ctattccagg cagaggggc agcagaggca    85380 aagaaaaaga ggtttgagac tacatattaa actggagaag tgcatatggt ctatacttac    85440
tgcttagcaa cagagtagaa tgatttgctg ggaggtgaga ctgaattaat attaatctat    85500
tgatttctct ttgaaattta caaaattttc tcctctcccc ttccttcttt atgtattttg    85560
gttctactgg agtcagttca ggtgtttctt aggaaattgt tctttatgat ctctgtgagt    85620
tgacattaaa atatacatta tgtatgttct gtgacacatt gttactctta tatgttagtt    85680
gtttaacacc tatatgggct cttgcctcag ctaaacagtg agttctcaaa ggtcacattc    85740
atgattagca gccacactga attattatta catggaagaa tggaaggcag gaatgaagaa    85800
aggaatggtg ggagggagga agaaggtagg aaggaaaaag aaacaagggg cggaataagc    85860
gcttgtagtg gaagatggaa ttaatgtttt tcaagagtat cttagtttct aagatgctca    85920
aatacaatga gaaatatatt tgagcatcct gaattgtgtg aaagttttaa aataatatt    85980 gtcaatgttc aggagaaaaa ttcttctgaa catgtgaaac aagaggaaga ccgaaggtag    86040
atatgcacag aaccctatcc acagttactg agtatgttta gtagggtaga aattgagaaa    86100
aactgcctta tagagagctc agctccaaaa tgactggcat gagatttaaa ctcagcatgt    86160
ataggttaca caaaataata tcacattcca atcatagata tcatagaccc taaaagggca    86220
atagtgcaag atctttcatt gcactgtctt gatatttcta agtcaaactg cttttttgttt    86280 caaggaaaca aaacctcttg aggaagaaac ttctgagatg gcagctgcca gagatataca    86340
agctgcccaa gtgaggggtt aggaaaagct gaagccaggc agacatgact gtgggtccag    86400
gctctacctc ttggtagcta tgtgaccatc agcaaggtgc tgtgtttctt ctacccaagc    86460
ttcagtttcc ttgcttatta aatacaatga gttttttttt tttcttcctg acagagggg    86520 cagcaaagac aaaaaattga ttacaggaca gggagtatct gaaaaactcg gcattgtgcc    86580
tgacacgtaa agtgctcgga aaataacagc cataattatt gttgacaagt ctggagcagg    86640
aaaacaaaca agcatacaaa acacaagatt agactgtagg ttaaaaaata caaggtctag    86700
ttctggctct gtcatttatt ttctatgtaa cctcagtcac atgtgttttt ttccctcatc    86760
tatacaattg gagaattcta cctattgtac ctacttggca gcatcatatg agattatata    86820
gatatagata tatatagcac tatatggtct aagggatcat ttttattaca ggcttgattt    86880
gaaaaacgca gagttccact ccctcaagat gaagcacccg tgccttgttc tgcctgacag    86940
```

```
cctaggactg atgctacttg cagaattttta gtgctcagcc ccttcagaga ttgccccagc    87000
tacagagcgg ccataaccaa ccacacaccc tccagagggt tgcctggata aaatgaccac    87060
tccatataga aggcctggcc aaattggccc gagtctggac aacaatgaag ggccctgata    87120
gcttcagagc tccccatagg gttggtggag gctgctattg agattacttt gcccatcaac    87180
ttctccctgc tgcttcctgc ttccttcccc ttccttcaac agatgtggac tccatggaca    87240
ctccttaata aacatcttgc aagctaaact gcttctcaga atctgcttcc cagagaacta    87300
atcccgtata atcccactga tacatttggt tacatatgta catattgaat aaagtttatt    87360
ttacctagca atttgggtaa aatattagct cgttacaaat ttccaaagtg cacagtgctt    87420
gcaacttttta tctcatattg tatgactttg aaagttgttg agagcatatt ttataaataa    87480
tctcgctttg ggtgttttag tagtgtatgt gtagcgcata aattaggcag cattctcata    87540
caacacatat atcaggtact acagggacag aggaagatca gcgtgtatca acaaaaacca    87600
cacattttat gattaacaca gaggatgata tggaaagttg atgtataccc tcccctaatt    87660
ttttccccga ctctacaacc atgctgtgat gttcctggct ttgtgtgagt taacttactt    87720
gggagtacaa gaaaagaaaa gaggcttttc agcgtaggat tatttgttta tttgtttgtt    87780
tgtttgttta agagataaga tctcactctg ttgcccgggc ttaagtgcag tgacgcaatc    87840
atagttcact gcagccttga actcctgggc acaagcaatc caattctccc atcttggcct    87900
cctgagtagc tggaactaaa ggcatgtgcc accatgccca tcatgttgtt tttccttgtt    87960
aaaaccactg aagccatctt cctggtaccc atgatgagat cgcttctcta cttgtcttct    88020
tgttgcttat tctatcatct ctgcacctcc tgctttccaa gaattcactg gctactagat    88080
agccttctgc tattttctag tatccttatg tgctctcaaa atatgtgata cataagcaaa    88140
acactgttaa ccatcacgaa agtttagatt aacagcntnt ttctnttnnt gtagttgcaa    88200
tctttcctct ctccttctac catttttttat ttgttttaat gaaaagaggc ttctaagcac    88260
tgattttcac tacctcttca agagccacaa aaatcaaaag tactaagagt aatattttta    88320
actttaggag cccaggcaat cttttcaaata gatgacaagc ttacggtcaa taaagaggaa    88380
ttttaaccac atatctcatg gatacaatga tgaaacttgt cccttttac agtcaggaag    88440
tagaatcacc agacctcaag tcaaagtcca catttaaatc ccaaacactc agcttcctat    88500
gacgcatgca gacatccttg cccttttgaac atactacatc ccgtaatagc tgttttgcag    88560
tgaatgcaca tttcctggag aatcgaggtt gcctcctggc cttccaatgt cctgtgcttc    88620
acttctataa taggtacata ttcatgggca aagctgttgc ctttgtgttt tcactgttca    88680
agctcaggca ggaacataag ttatcaggat agcatcctaa aagcacttct atttcttcct    88740
gttggcagta catgccagaa aactaaattt tatgttgttt catcttattt ttggcaagtt    88800
cattctgcat aagatatatc ttaacagtag ccaagcacaa gcaatcaaac tcagacttat    88860
tattttctta atcccgtgtc accctcgat atggccattt tggccagatt taccctgtga    88920
ttaaatgtct acttgtgttc tgtttattgg ttattgtctc agtacatctg caattttaag    88980
attcattaca ttatcttttg ctcatctctc ctattcacct gtccgcagtc tgtgtttcac    89040
ctttgccctc acctcctgtc atcagcctgt ctcccaaaaa aggccccacc attgttctgt    89100
tgcaaaattc tatttggtca gctgcctcat tacctctatt caggtctttt tcctctcccc    89160
atatgctcca gttctctgtt cctggatatg ctgggtataa ctggcactca ctactgagta    89220
caggtacccc ttatatgtga gagtcctgga ggcacccaac caatctcact atggtcctca    89280
gtcaatgact gaaattgagc tgcatttctt catggagaag tgggaaaaat acctctttcc    89340
```

```
caatattagc atggctgtat tccacacaag cataagacat ttatgtttgt gtctccatca    89400
tttacaaagt ttatagtgaa gtagctcttt taggttataa cttacactgc ttactttccc    89460
caccacctat tagcaaaaga atgagcccat gggacatttg aataggagac caatctgagt    89520
gaagcttatc tacatgcaga taggtaacat ccaaaatgct tcttggtaaa gccaaatgct    89580
gatgaacagt gggccaaact cattagttta gctctattcc ccgctaccca gctttaatga    89640
ggtataactg acaagtaaaa cttacatata tttaagatgt acaacatgat aatttgatat    89700
atatacatgg taaaatggtg accacaatca agttaattaa catatccgtc acctcacata    89760
gttaccattt tttctttgtg gtacaaacac ttaagatcta ctctcttagc aaatataaag    89820
tatacaatac agtattaata actacagtct ctatgttgtc cattcatcc ccagaactta    89880 ttcatctaat aactgaaagt ttatactata tgatcttagc tctttctttt atggtaagtc    89940
tcagactagc cctactcctg ggggagacta atgaaattc ctgagcagaa agttggagta    90000
gagcaggtag atctgaatag aaatttagca tgaaagaagt catagggcc taagaagaag    90060 gagcattggg aaggggaca tggtatgagg acagaagcag aattatcatc aagagactgc    90120
aaagcacata tcaatcataa ctgccaggaa gccatatgga tgccagaata aggctcgtag    90180
tcctattgtg gctatttaca taggcatttc tgcacataac ctctgtcaag gtacatgtt    90240 ggctgttctc agcaccatcg gacagaacaa accattacca cttgcctctc catgtgtgag    90300
gacctcccag cagaaatact gcttacctgt gccatgagat ttgtttagta cccctgtgct    90360
gtctgggtac cttcctctaa gcttcccagg aaattcctaa ggtctggaaa cacaggatag    90420
tgtttcttga ccagtagtgg ttttcaaaga gaattttcat tccacttcca gcctctgcat    90480
ttgggtagaa caagaccaca ataaaatgaa ttccattaca caaatattac ttacaaattc    90540
tgatccttcc tgaagtgact tggaatattg tatttctctt ttgatttgga aagagttgat    90600
atttcttctc accaacctgc actaagttct gtttgaactg agaatctttt acattggctt    90660
tctttttttt ttcccaaaat ctgaagtagt gtttcttttg accttaccgt tactgaaagg    90720
agaacaatat ggctataaaa gtaagtgcag cgtctctaag aaatccaagt gtttagcaaa    90780
tcaaatacaa cataaggtac attaaggttt tattaaaatc tcatttattg gcaagagttg    90840
cttctttctg aagagttcta gtctgcctct caagaattaa tctgatgttt tccatttgtt    90900
ttatagtatg ttttttaccc ttttcctcac acaggtctca tacctttatg aaacttttcc    90960
cttatgactc tacttcagtg tcgtcttccc agagaaccca accagtgaca tcctgaaagc    91020
atatgctgtg agctttgtga gagctgggac ttaacggcgg ttttgttcag ggctctgttt    91080
ccagtgtcgt gctccgcaga cgacataaag caggcactgg ataggaatgt tgaatgttaa    91140
atgaatgaac agcatccatg cttatggtca acaaacctag tggcctctga gtgtcatgat    91200
gaagagcact tgttctggaa tctgaccata tgagttcagg ttggctcagt tgcttcccag    91260
tttgtaacat tggatgagtt cattaacttt tctactcttt tatttttca tgtgtaaaat    91320 cagaaccata gttgtatcca caagatagtt tttcttaaat ttgtattgtt ttatcttgtt    91380
tttgaagatt aagtgaattg tgaagcactt aggataacac tgagcagata gatgttctca    91440
attaaagtca atgatactac acagtatgaa tgtttatggt ggcaaagtgc tcactatctg    91500
attaggtgat tcttactagt tttagaagtt ttcatctcta gaatgacttt tctgccctct    91560
ccatcaatat actttattat agaagtctgt tcattctctt taaaaacctt agtagtctct    91620
gaaataaact tgctttacaa aatctatacg gagggaaatt ttccatcttg tttagtgtta    91680
```

-continued

```
tatccccact tcaagaagaa taattaacat gtaatagttg tttaatacat atttatttaa    91740
agaatgcatt gagtaaattg tttaagtttt atttttatgt tatggcaaat ttgacctcat    91800
aattgtatct atcagttcta tctcagctcc gtggagcaaa agataatggc tttaatgcct    91860
tttattttct ttttagctat tcacattttt atttgttatt tttaaaaatt attcttaatt    91920
ttttggtgta catagtagat gtatatatcc ttatggggta catgtgatat tttgatactg    91980
gctttaatgc cttttctata tgacaattta ttggacattt gaagaaacga tctttccttt    92040
atttctctat tctttacgtt ttccttatga ttgtgtgtgt ggtgggtggg ggtaggtaat    92100
ggaagataat atgaatatag aagaagacat agagaattcc taagatgggg cgggcgtggt    92160
ggcccacgcc tgtaatccca gcaatttggg aggctgaggc aggcagatca catgaggcta    92220
ggaattcaag actagcctgg ccaacatggc ggaaacctgt cttgactaaa aatacaaaaa    92280
ttagctgggc atggtggcac acacctgtaa tcccagttac ctgggaggct gaggcacaag    92340
gatcacctga gctggggaag cagaagttgc agtgagctga gaccacacca ctgcactcca    92400
gcctgggtga cagagtgaga ctctttaaaa gagagagaga gagagagaga gagagagaga    92460
gaattcccaa gagtgaattt ccagctccaa gagctttaaa gtgtcatgtg aagtcactga    92520
aggaagaaga ctttggagag tggtgttcca gtaataatat ccggccgtta gaatagtctc    92580
ctaaaccaca gaaaaatata taccagaaga gtatctaatt caagaaagag gaagatatgt    92640
aacccagaaa atgcaatcag gtctgccata cggaagcaaa tagatggcat ctgtatggca    92700
gacctggaga ggacagaggg gctcagggga gaagatgtac tagtcattta cctatgggtc    92760
cttggctcca gatccatatt cctgtactca actttgtgat gcttaggtta ggactgtaca    92820
aattgtattt cagagaccta tttttcagca ctagagaaat attaggaggt aaaagaagag    92880
gagctgggtc ttcctattta ttgctatttc tgtcaatatc aatctacagt ggtaattcat    92940
ttccacattt ggcagctgaa taaacactat tgggaaaaaa tatacacctg cttttttaaaa   93000
gtcattatta tttaagttct ccctatccac ctgaatagca cactgttcaa agctcatatg    93060
ccattgcaaa ataattcta aaatttgttt ggaaccacaa aagcacctga atagccaaag     93120
caattttgag gaagaagaaa aaacatgaaa tcacacttct tgatttagaa ttatactaca    93180
aagctatagt gatcaaaaca gtatggtatg ggcataaaaa cagacacata gaccaatgaa    93240
acatactaga aagcctgaat ataaacccaa gcacaaacag ttaactaatt tttcccaaag    93300
tcacaagaaa aacaaaatga gacaaggata gtcacttcaa taaatggtgt taggaaaatt    93360
agatatccac tcgtaaaagg ataaaattga atccttatct aacactaaac ataaaagcta    93420
ctcaaagttg attaaaggct taaacataag acctgaaact ataaaattcc tagaagaaaa    93480
tataggaaaa aatactccgt gacattggcc ttgccagtga tttat                    93525
```

REGULATORY CONSTRUCTS COMPRISING INTRON 3 OF PROSTATE SPECIFIC MEMBRANE ANTIGEN GENE

FIELD OF THE INVENTION

The present invention relates to constructs comprising a novel regulatory element derived from a prostate specific gene. The present invention also relates to diagnostic and therapeutic methods involving the use of these constructs.

BACKGROUND OF THE INVENTION

The isolation and characterisation of DNA regions which control tissue specific and/or hormonally-regulated gene expression has been an important to the understanding of the developmental processes by which expression of particular genes is limited to specific cell types. Promoter regions are found immediately upstream and often overlapping the start site(s) of transcription and are critical for initiation and basal levels of transcription. Enhancers are regulatory regions which may lie some distance from the transcription start site, either upstream or downstream of a gene or within introns and which often confer high level tissue specific or hormonally-regulated expression; in some cases their action is specific to particular promoters. The function of both promoters and enhancers is mediated by specific proteins, transcription factors, that bind to specific DNA sequences. Alone or in combination with other transcription factors they recruit the core transcription machinery including RNA polymerase to the transcription initiation site and act to stimulate their activity. Isolated promoters and enhancer sequences can be used, in gene therapy for example, to direct expression of other genes in a cell or tissue specific manner and also provide targets for the development of agents that can specifically modulate gene expression.

The promoters and regulatory regions of a number of genes that are expressed in the prostate have been studied either using transfection techniques or by following gene expression in transgenic mice. We have previously compared the cell-type specificity of expression directed by promoters of the prostate-expressed genes, probasin (Pb) and relaxin genes and the promoter and enhancer of the prostate specific antigen (PSA) gene (1). Most of the genes identified as prostate-specific are androgen-inducible and this aspect of their function has been studied in some detail. Thus the importance of androgen response elements for induced expression and/or binding of androgen receptor have been characterised in the PSA (2, 3), human glandular kallikrein (KLK2) (4), rat prostatic steroid binding proteins (PSBP) (5, 6), probasin Pb (7, 8) and prostatic acid phosphatase genes (9) and in regulatory elements in the introns of the rat PSBP C3(1) gene (10) and the rat 20-KDa androgen regulated protein (11).

Among the core promoter regions analysed only that of the probasin gene confers substantial prostate specificity of expression (1, 15). Elements involved in conferring prostate-specificity of expression per se, as distinct from androgen responsiveness, have not been well characterised, though tissue-specific factors binding to regions of the PSBP C3 gene promoter and 1st intron have been identified (9, 12). The gene for rat PSBP C(3) with 4 kb upstream and 2 kb downstream flanking sequences is expressed tissue-specifically and with appropriate hormonal control in transgenic mice (13). The use of a 5 kb upstream region from the rat PSBP C3(1) gene to express the SV40 T-antigen could elicit prostate tumours, but expression was not highly restricted and other abnormalities were common (14). Studies with transgenic mice have established that regions of the probasin and PSBP C(3) genes can confer prostate specificity.

The PSA and probasin regulatory regions are the two most studied among prostate-expressed genes. It has been established that a 430 bp region upstream of the rat probasin gene is able to confer prostate specificity of expression on reporter genes in transfection experiments (1) and in transgenic animals (15, 16); when used to target expression of the SV40 T-antigen, prostate tumours develop specifically (17, 18). This expression is not totally specific but specificity is significantly improved by the inclusion of MAR (matrix attachment regions) from the chick lysozyme gene (15). The 430 bp promoter region is strongly responsive to androgen induction and androgen response elements which bind the androgen receptor (AR) have been characterised (4, 6, 7, 16).

The PSA upstream region (to −630 bp) also acts as a strongly androgen responsive promoter and androgen response elements have also been characterised (2, 3). However, this region is not sufficient to direct cell type specific expression in culture (1) or tissue specific expression in transgenic mice (19). Use of the 630 bp human PSA promoter region to express an activated Ha-ras oncogene in transgenic mice led to the development of salivary gland and not prostate tumours (19). Pang et al. have reported that the equivalent promoter region isolated from a prostate cancer patient contained 7 mutations compared to the published sequence and was highly active in the prostate cancer cell line LNCaP (20, 21). More recently, an enhancer region has been identified in the region 4 to 5 kb upstream of the transcription start site of the PSA gene (20, 21). This PSA enhancer has been shown to act as an androgen-inducible enhancer and in combination with the PSA promoter to display significant cell-type specificity (1, 20, 21).

Prostate-Specific Membrane Antigen

Prostate specific membrane antigen (PSMA) is one of the few prostate-specific proteins identified whose expression is not induced by androgens. PSMA was first identified as the antigen bound to by the monoclonal antibody 7E11-C5(25). The antibody was raised against a membrane fraction of the prostate cancer cell line LNCaP and was shown to bind specifically to normal prostate tissue as well as primary and metastatic prostate cancer tissue. This antibody was later found to bind to an internal epitope of this membrane-bound protein (26, 27). Subsequently, other monoclonal antibodies targeted to the extracellular domain of the protein have been isolated (28, 29).

The cDNA encoding PSMA has been cloned and its sequence determined (30). PSMA is a Type II integral membrane protein and is associated with the plasma membrane of expressing cells such as LNCaP (30). A splice variant of PSMA (Psm') that lacks the membrane anchor domain and has been shown to be cytoplasmically located has also been identified (31) The ratio of PSMA to Psm' has been reported to be increased in prostate cancer as compared with normal prostate or benign hyperplasia (31). PSMA has been shown to possess two related enzymatic activities, it acts as a carboxypeptidase (folate hydrolase) on poly γ-glutamated folates (32) and as a peptidase on the acidic neuropeptide N-acetylaspartyl glutamate (33). This latter activity is consistent with the expression of PSMA or a related protein in the brain.

The specificity of PSMA expression has been studied at both the protein and RNA level. In addition to its major site of expression in the prostate immunohistochemical studies have identified PSMA expression in the duodenum brush border/small intestine, in a subset of proximal tubules in the kidney and in rare cells in the colon (34, 35). All other normal issues studies have been negative for expression, except for striated muscle which stains with the 7E11-C5 antibody, but not with antibodies to the external domain of PSMA (28).

Both the 7E11-C5 and external domain antibodies have been found to react with tumour vasculature of a wide range of human tumour types (28, 36), indicating specific induction of PSMA expression. PSMA expression has not been identified in any normal vasculature.

RNA expression has been found to largely parallel the protein expression data. RNAse protection analysis identified PSMA mRNA in the prostate, salivary gland and brain and sometimes in the small intestine (37). The identification of PSMA RNA in the brain is consistent with the cloning of a closely related cDNA from rat brain (33). Immunohistochemical analyses have failed, however, to identify antigenically reactive PSMA in human brain tissue.

PSMA expression has been shown to be down regulated in the presence of androgens and expression is generally elevated in late stage prostate cancer and in patients undergoing androgen deprivation or ablation therapies (37, 38). Expression of PSMA has also been found to be regulated by a number of growth factors; bFGF, TGF-α and EGF upregulate expression while TNF-α decreases it (39).

The restricted high level expression of PSMA in prostate cells and the induction of its expression in the vasculature of a wide range of tumours make it ideal for the targeting of prostate and other tumour types. Genomic clones encompassing the PSMA gene have been isolated and its sequence and exon/intron structure determined (40). Regulatory regions controlling its expression may find use in gene therapeutic cancer treatments, enabling the restricted or high level expression in the target cell types. Such regulatory regions also provide a target for the development of agents that may interfere with gene expression in the target cell types.

SUMMARY OF THE INVENTION

The present inventors have identified a novel regulatory element in the PSM gene. The regultory element is an enhancer located in intron 3 of the PSM gene. This is the first report, to the applicant's knowledge, of an enhancer derived from an androgen-independent, prostate specific gene.

When used herein, the PSM gene refers to the PSM genomic sequence described in O'Keefe et al., (1988)(40) (Genbank accession number AF007544) (SEQ ID NO: 2), the entire contents of which are incorporated herein by reference.

Accordingly, in a first aspect the present invention provides a recombinant polynucleotide comprising at least one regulatory element derived from intron 3 of the PSM gene and a sequence encoding a heterologous polypeptide.

By "heterologous polypeptide" we mean a polypeptide other than the prostate specific membrane antigen (PSMA) polypeptide.

In a preferred embodiment, the recombinant DNA molecule further comprises a promoter. Preferably, the promoter is located upstream from and is operably linked to the sequence encoding the polypeptide.

In a second aspect, the present invention provides a recombinant expression cassette comprising at least one regulatory element derived from intron 3 of the PSM gene, a promoter, and an insertion site into which a coding sequence is optionally inserted, the insertion site being adjacent to and downstream of the promoter.

The regulatory element(s) may be located in either orientation anywhere within the recombinant DNA molecule or expression cassette of the present invention. For example, the regulatory element may be located downstream of the coding sequence (eg. downstream of the 3' termination or polyadenylation signals) or within an intron located in the coding sequence. In a preferred embodiment, the regulatory element is located adjacent to the promoter. More preferably, the regulatory element is upstream of the promoter.

Within the context of the present invention, it is preferred that the regulatory element is an enhancer element. Preferably, the enhancer element includes intron 3 of the PSM gene or a part thereof.

In a preferred embodiment, the enhancer element comprises (a) a sequence comprising nucleotides 14,045 to 15,804, nucleotides 14,760 to 15,804, nucleotides 14,760 to 16,575 or nucleotides 14,045 to 16,575 of the PSM gene; or (b) a nucleic acid sequence which hybridises under high stringency to a sequence defined in paragraph (a).

In one preferred embodiment, the enhancer element comprises nucleotides 14760 to 14930 as shown in FIG. 11 (SEQ ID NO. 1) or a sequence which hybridizes thereto under high stringency.

In another preferred embodiment, the enhancer element comprises nucleotides 14760 to 15091 as shown in FIG. 11 (SEQ ID NO. 1) or a sequence which hybridizes thereto under high stringency.

In a further preferred embodiment the recombinant DNA molecule or expression cassette of the present invention comprises two or more regulatory elements derived from intron 3 of the PSM gene. In one preferred embodiment, the recombinant DNA molecule or expression cassette comprises a dimer or higher multimer of regulatory elements derived from intron 3 of the PSMA gene.

It will be appreciated by those skilled in the art that any suitable promoter may be used in the context of the present invention. Preferred promoters include, but are not limited to, herpes virus thymidine kinase (TK), and Rous sarcoma virus (RSV) promoters, promoters active in the prostate, such as probasin, PSM, and PSA, or promoters active in vascular endothelium.

In a preferred embodiment, the recombinant DNA molecule and expression cassette of the present invention further comprise a polyadenylation signal located downstream from and operably linked to the sequence encoding the polypeptide, or downstream from the insertion site. Preferably, the polyadenylation signal is the SV40 polyadenylation signal or the bovine growth hormone polyadenylation signal as described in U.S. Pat. No. 5,122,458, the entire contents of which are incorporated herein by reference.

In a third aspect, the present invention provides a vector comprising a recombinant DNA molecule of the first aspect or an expression cassette of the second aspect.

In one preferred embodiment the vector comprises a gene encoding a selectable marker. The vector may further include an origin of replication.

It is presently preferred that the vector is human adenovirus Type 5 or ovine adenovirus.

In a fourth aspect the present invention provides an isolated nucleic acid molecule, the nucleic acid molecule having enhancer activity and comprising (a) a sequence comprising nucleotides 14760 to 14930 as shown in FIG. 11 (SEQ ID NO. 1), or (b) a nucleic acid sequence which hybridizes under high stringency to the sequence defined in paragraph (a).

In a preferred embodiment of the fourth aspect, the isolated nucleotide molecule comprises
   (a) a sequence comprising nucleotides 14760 to 15091 as shown in FIG. 11 (SEQ ID NO. 1), or
   (b) a nucleic acid sequence which hybridizes under high stringency to the sequence defined in paragraph (a).

In a further preferred embodiment of the fourth aspect, the isolated nucleotide molecule is less than 7.5 kb.

In a fifth aspect the present invention provides a method for directing expression of a coding sequence of interest in a cell, the method comprising introducing into the cell a recombinant expression cassette comprising at least one regulatory element derived from intron 3 of the PSMA gene, a promoter, and a coding sequence, wherein the regulatory element and promoter direct expression of the coding sequence.

In a preferred embodiment of the fifth aspect, the cell is a prostate cell, bladder cell, breast cell or vascular endothelial cell.

In a sixth aspect the present invention provides a method for the treatment of cancer which method comprises administering to a subject a recombinant expression cassette comprising at least one regulatory element derived from intron 3 of the PSM gene, a promoter, and a coding sequence, wherein the regulatory element and promoter direct expression of the coding sequence.

In a preferred embodiment of the sixth aspect, the coding sequence encodes a toxin, a protein involved in viral replication, or an enzyme which converts a prodrug to a toxic drug. For example, the coding sequence may encode the enzyme purine nucleoside phosphorylase which converts the prodrugs fludarabine and 6-methylpurine 2-doexyriboside (6 MPDR) to their toxic derivatives.

As the constructs of the present invention are useful for expression of proteins in vascular endothelial cells, a range of cancer types may be treated within the context of the sixth aspect of the present invention. Examples of suitable cancer types include renal cell carcinoma, transitional cell carcinoma, colonic adenocarcinoma, neuroendocrine carcinoma, malignant melanoma, pancreatic duct carcinoma, breast carcinoma, soft tissue carcinoma, non-small cell lung carcinoma, testicular embryonal carcinoma and glioblastoma multiforme. In a preferred embodiment of the sixth aspect, however, the cancer is selected from prostate, bladder or breast cancer.

As will be appreciated by those skilled in the field, the present invention provides novel regulatory elements from a gene expressed specifically in prostate, which are active both in the presence and absence of androgens. These regulatory elements may therefore be used for high level gene expression in prostate cells. Combinations of one or more of the regulatory elements with the probasin and PSA promoters are examples of constructs that provide for high level expression with strong prostate specificity.

The regulatory elements of the present invention may also be useful for directing expression in a limited range of other cell types, including tumour neovasculature and kidney cells.

The regulatory elements of the present invention may be used to target specific expression of genes to prostate cells or tumour neovasculature or kidney cells in gene therapy.

The regulatory elements of the present invention may also be used to target specific expression of genes in the development of transgenic animal models of prostate disease.

The regulatory elements of the present invention may also be used to identify other genetic elements which are involved in the regulation of gene expression in prostate cells.

The regulatory elements of the present invention may also be used in assays to identify reagents that interfere with prostate gene expression, or to identify proteins and other factors involved in regulation of prostate gene expression.

When used herein, "high stringency" refers to conditions that
   (i) employ low ionic strength and high temperature for washing after hybridisation, for example, 0.1×SSC and 0.1% (w/v) SDS at 50° C.;
   (ii) employ during hybridisation conditions such that the hybridisation temperature is ≦25° C. lower than the duplex melting temperature of the hybridising polynucleotides, for example 1.5×SSPE, 10% (w/v) polyethylene glycol 6000, 7% (w/v) SDS, 0.25 mg/ml fragmented herring sperm DNA at 65° C.; or (iii) for example, 0.5M sodium phosphate, pH 7.2, 5 mM EDTA, 7% (w/v) SDS and 0.5% (w/v) BLOTTO at 70° C.: or (iv) employ during hybridisation a denaturing agent such as formamide, for example, 50% (v/v) formamide with 5×SSC, 50 nM sodium phosphate (pH 6.5) and 5× Denhardt's solution at 42° C.; or (v) employ, for example, 50% (v/v) formamide, 5×SSC, 50 mM sodium phosphate (pH 6.8), 0.1% (w/v) sodium pyrophosphate, 5× Denhardt's solution, sonicated salmon sperm DNA (50 μg/ml) and 10% dextran sulphate at 42° C.

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the nature of the present invention may be more clearly understood preferred forms thereof will now be described with reference to the following non-limiting Examples and Figures.

| B2 BglII | E EcoRI | H HinDIII | K KpnI | M MfeI | N NsiI |
|---|---|---|---|---|---|
| Nh NheI | P PstI | S SalI | Sp SpeI | X XbaI | |

Figure 4:
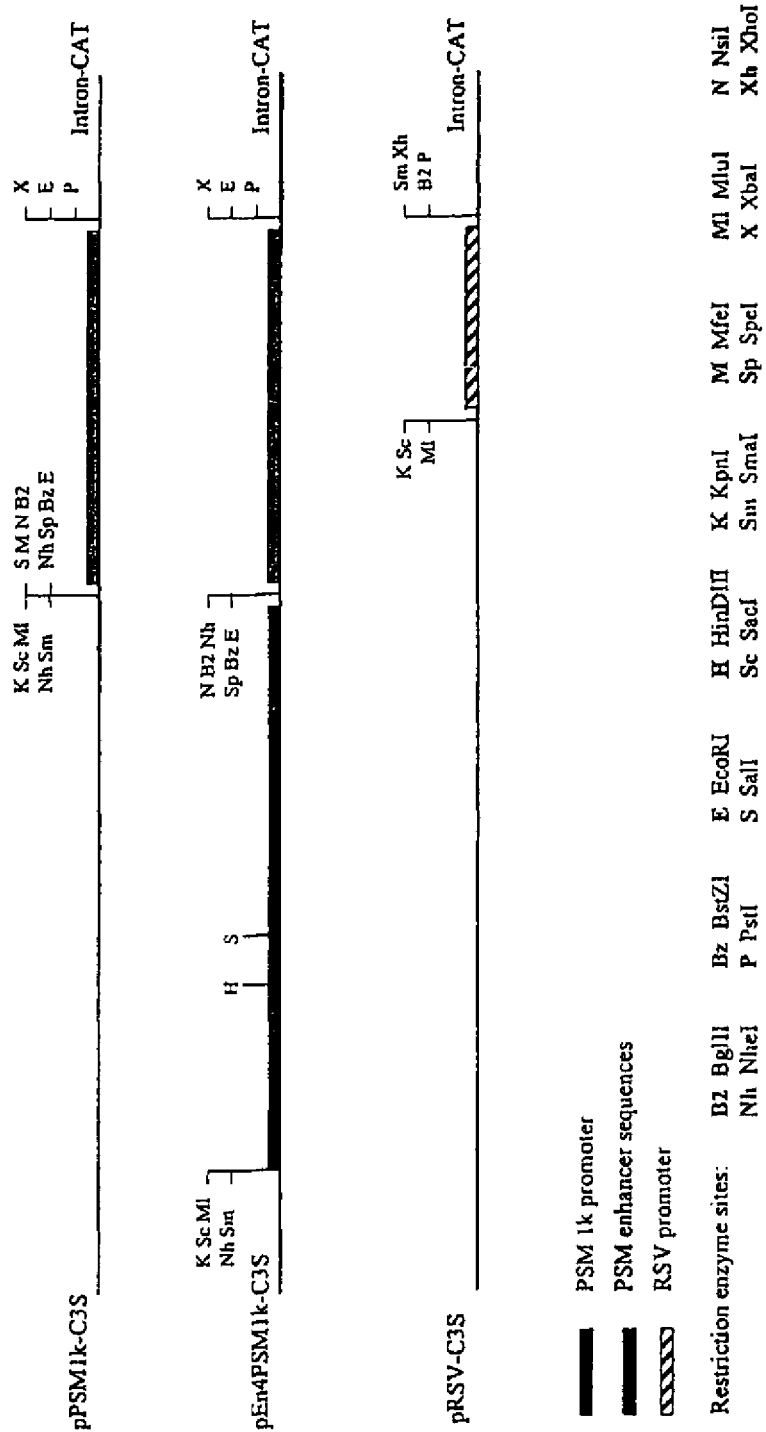

FIG. 4. Promoter and enhancer inserts in pCAT3SAT. Maps show the positions of the PSM 1 kb promoter, PSM En4 and the RSV promoter and their flanking restriction enzyme sites. To the right of the promoters is the leader sequence and chimeric intron and CAT reporter gene as present in the Promega pCAT3 Basic vector. Restriction enzyme sites are abbreviated as follows:

| B2 BglII | Bz BstZI | E EcoRI | H HinDIII | K KpnI | M MfeI |
|---|---|---|---|---|---|
| Ml MluI | N NsiI | Nh NheI | P PstI | S SalI | Sc SacI |
| Sm SmaI | Sp SpeI | X XbaI | Xh XhoI | | |

Figure 5:
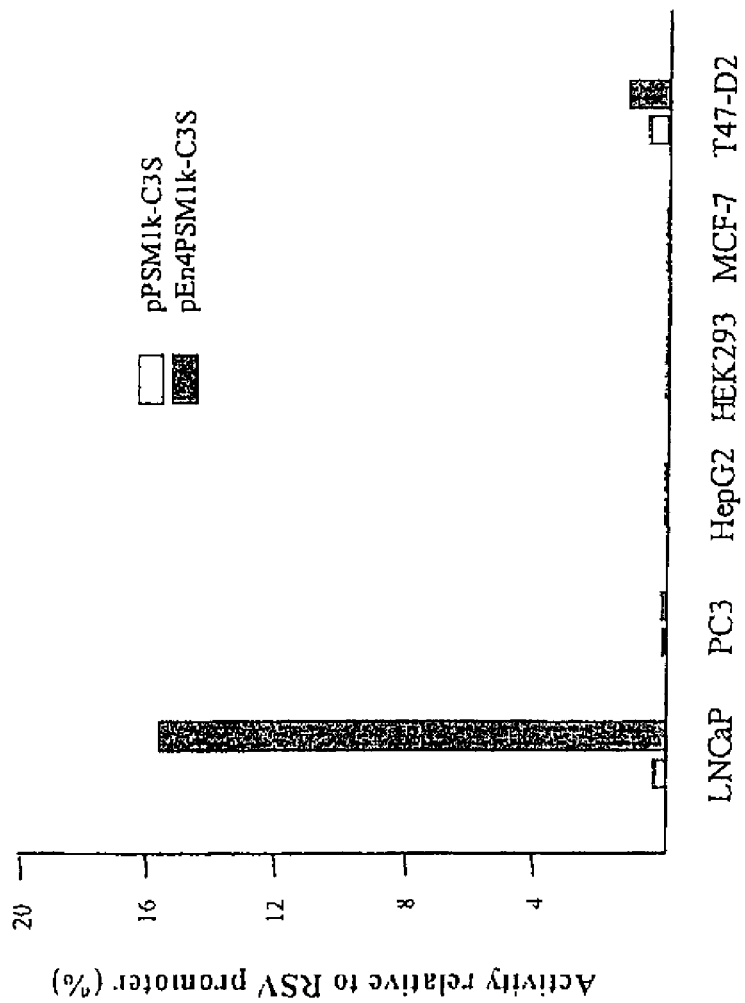

FIG. 5. Relative CAT expression directed by the PSM Enhancer4/PSM1k promoter. Following transfection of pPSM1k-C3S or pEn4PSM1k-C3S into the cell lines indicated normalised expression levels were determined for each construct and are expressed relative to that determined from transfection of the pRSV-C3S plasmid.

Figure 6:
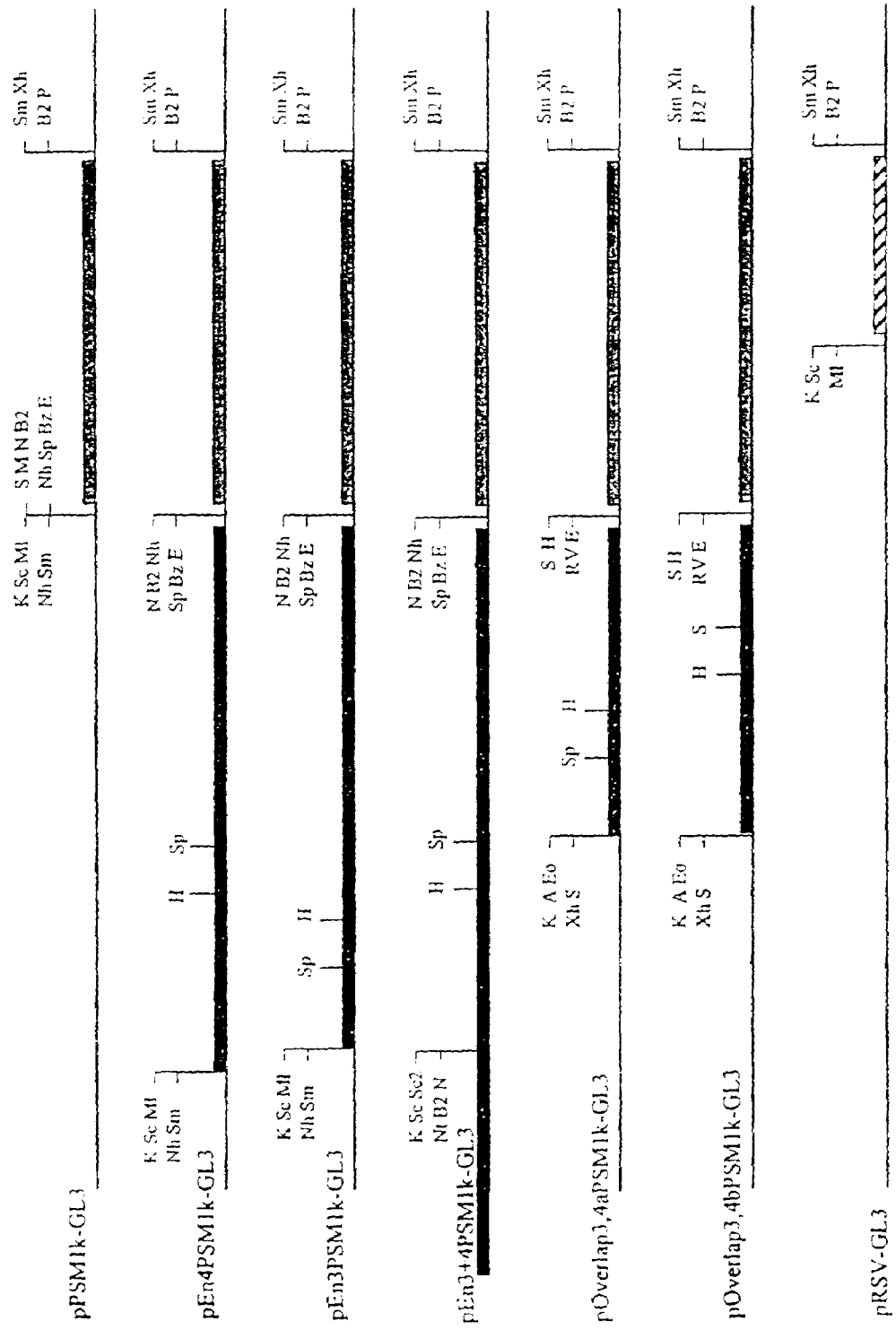
Figure 2:
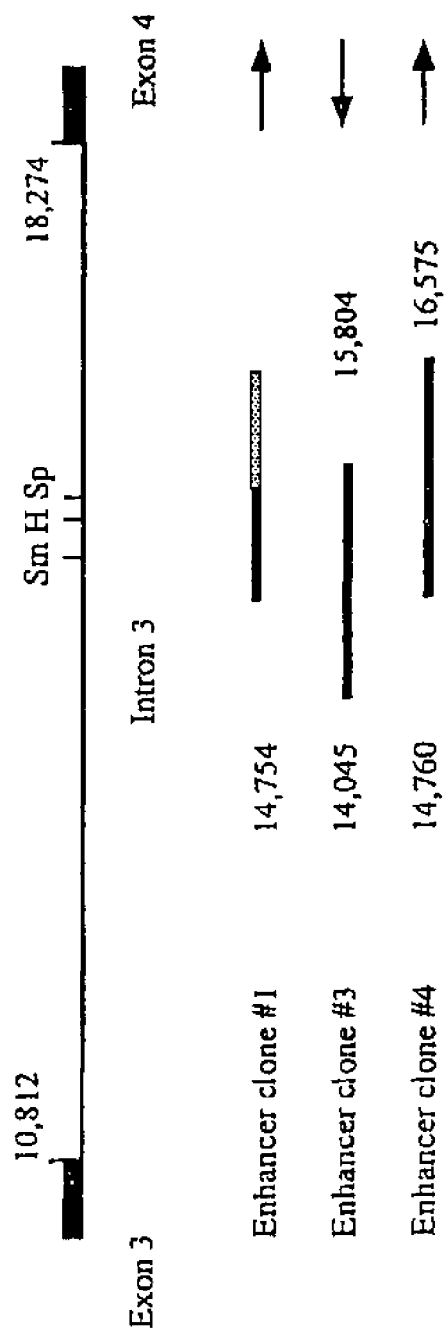

FIG. 6. Promoter and enhancer inserts in pGL3. Maps show the position and flanking restriction enzyme sites of the PSM 1 kb promoter (shaded boxes), PSM enhancer fragments (solid boxes) and the RSV promoter (diagonal shading) in the different constructs prepared in the pGL3 vector. To the right of the region shown is the leader and chimeric intron and luciferase reporter gene of the pGL3 vector. PEN4PSM1k-GL3 and pEn3PSm1k-GL3 contain sequences of enhancer clones #4 and #3 respectively as shown in FIG. 2. pEn3+4PSM1k-GL3 contains PSM enhancer sequences encompassing bases 14,045 to 16,575 (see FIG. 2). POverlap3,4aPSM1k-GL3 and pOverlap3,4bPSM1k-GL3 contain enhancer sequences from bases 14.760 to 15,804, the a and b constructs containing the enhancer sequences in opposite orientations as indicated by the position of the HinDIII and SpeI sites. Restriction enzyme sites are abbreviated as follows:

| A ApoI | B2 BglII | Bz BstZI | E EcoRI | Eo EccO109I | H HinDIII |
|---|---|---|---|---|---|
| K KpnI | M MfeI | Ml MluI | N NsiI | Nh NheI | Nt NotI |
| P PstI | RV EcoRV | S SalI | Sc SacI | Sc2 SacII | Sm SmaI |
| Sp SpeI | X XbaI | Xh XhoI | | | |

Figure 7:
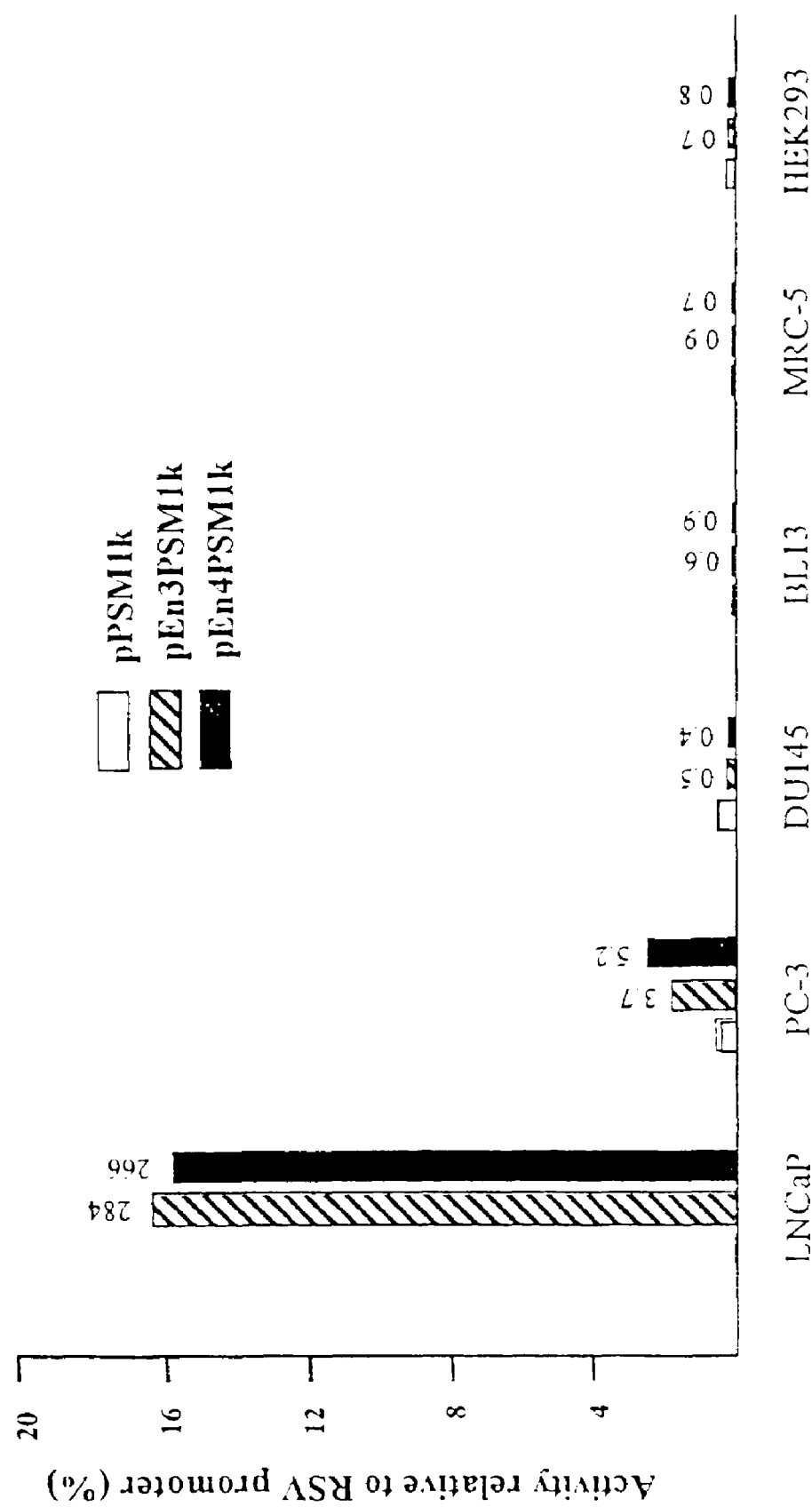

FIG. 7. Relative luciferase expression of PSM enhancer/promoter constructs in the pGL3 vector. Mixtures of luciferase reporter plasmids (1.5 µg) and the normalising plasmid pRSV-CAT (1 µg) were transfected into different cell lines as shown. Normalised luciferase expression was determined and activity of the different plasmids expressed relative to the normalised expression from pRSV-GL3. Numbers above the columns indicate the relative enhancement of activity compared with expression from the PSM promoter alone construct, pPSM1k-GL3.

Figure 8:
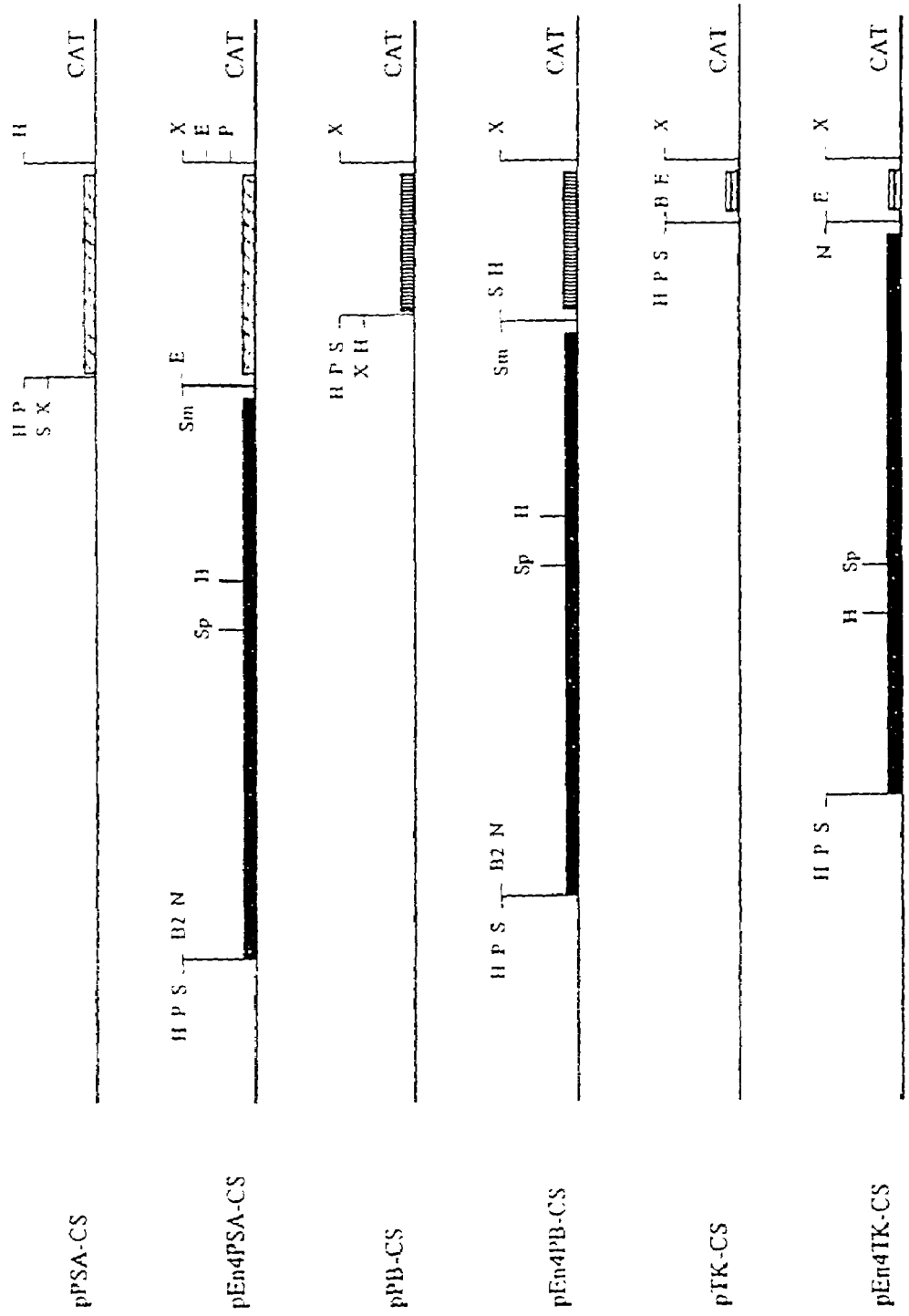

FIG. 8. PSM enhancer constructs with other promoters. Maps show the positions and flanking restriction enzyme sites of the PSM enhancer sequences (En4, solid boxes), and promoters from the PSA (diagonal pattern), probasin (vertical pattern) and thymidine kinase (horizontal pattern) genes. To the right of the promoters is the CAT reporter gene of the pCATSAT vector. Restriction enzyme sites are abbreviated as follows:

| B BamHI | B2 BglII | E EcoRI | H HinDIII | N NsiI | P PstI |
|---|---|---|---|---|---|
| S SalI | Sm SmaI | Sp SpeI | X XbaI | | |

Figure 9A:
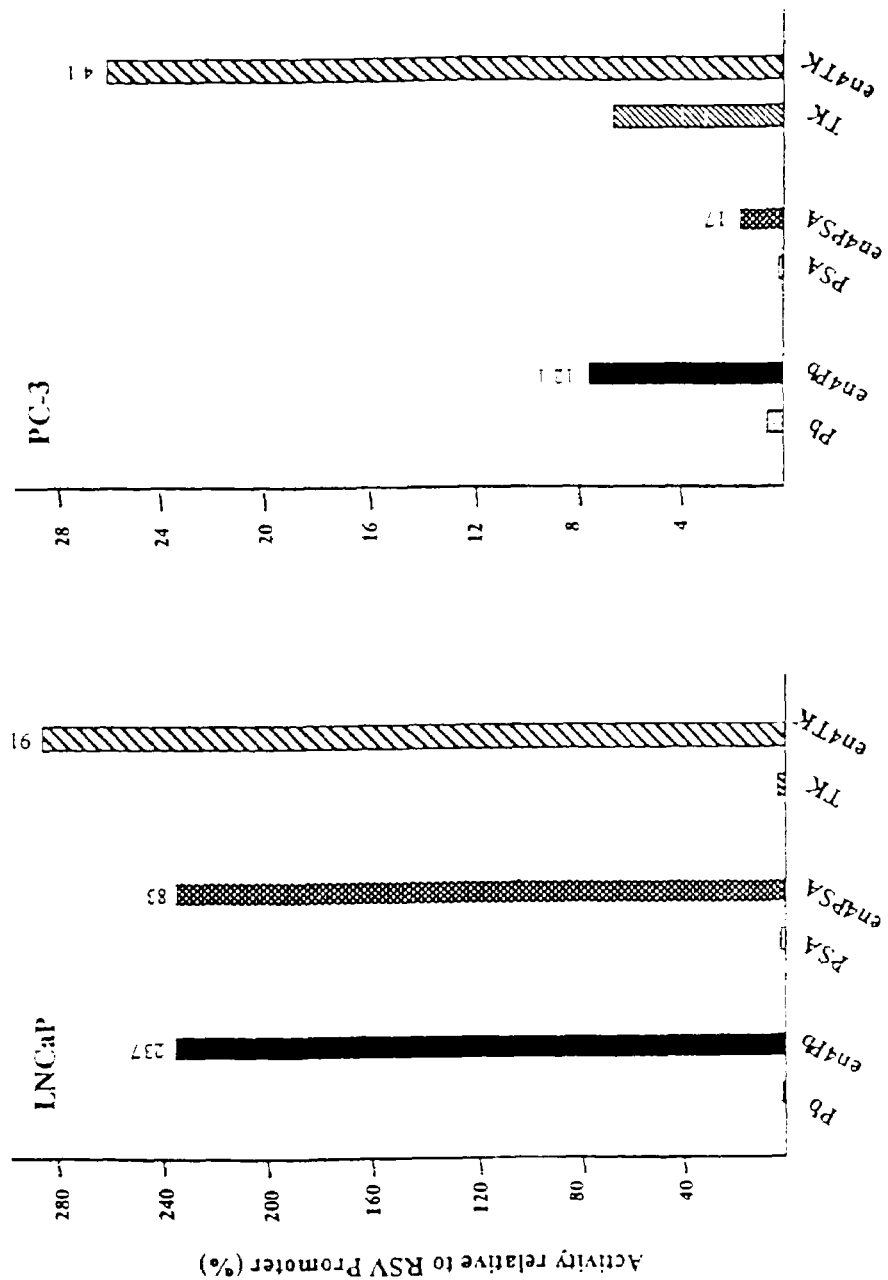
Figure 9B:
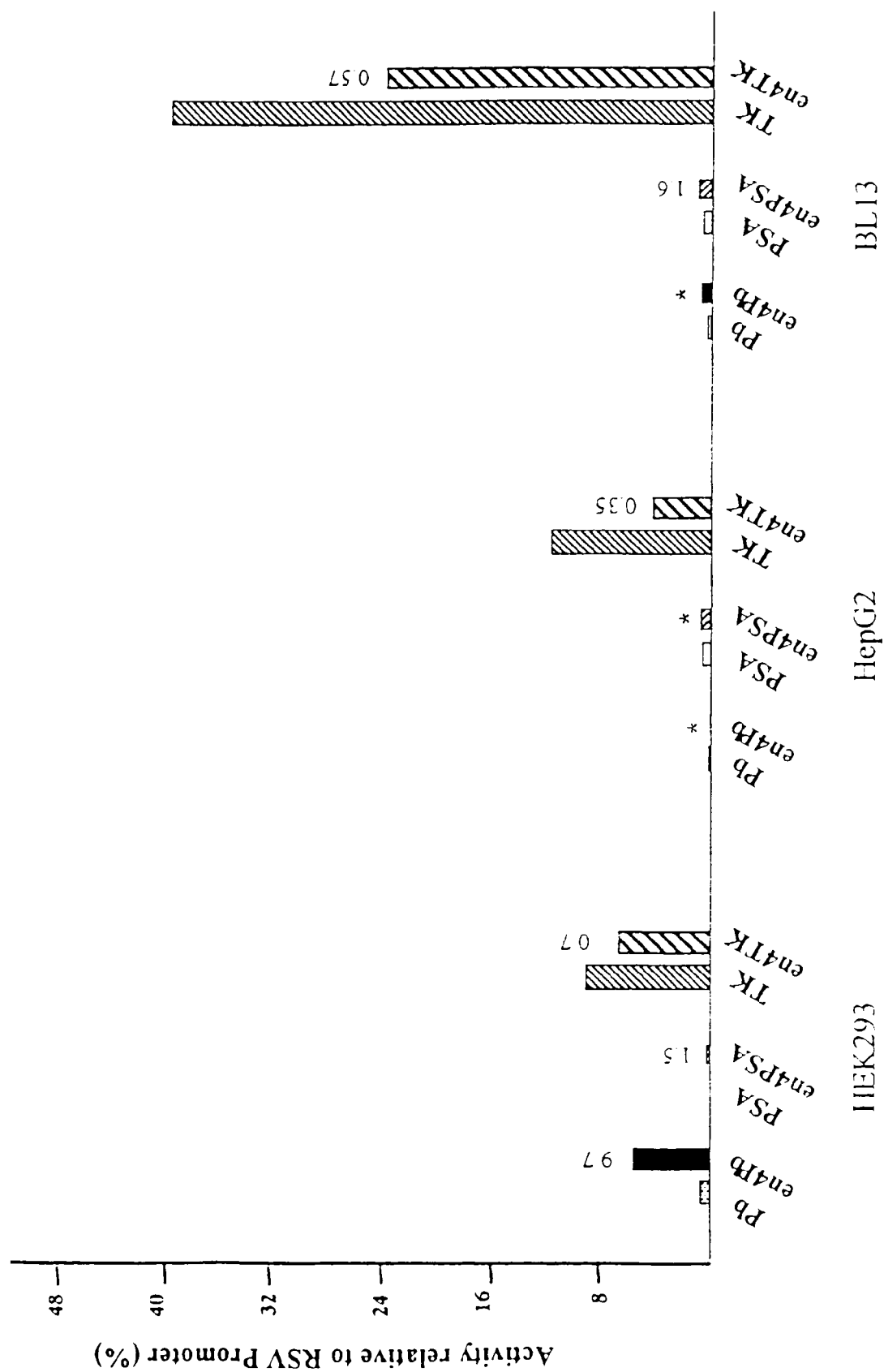

FIG. 9. Relative enhancement of heterologous promoters by PSM En4.

a. Prostate cell lines b. Non-prostate cell lines

Figure 10:
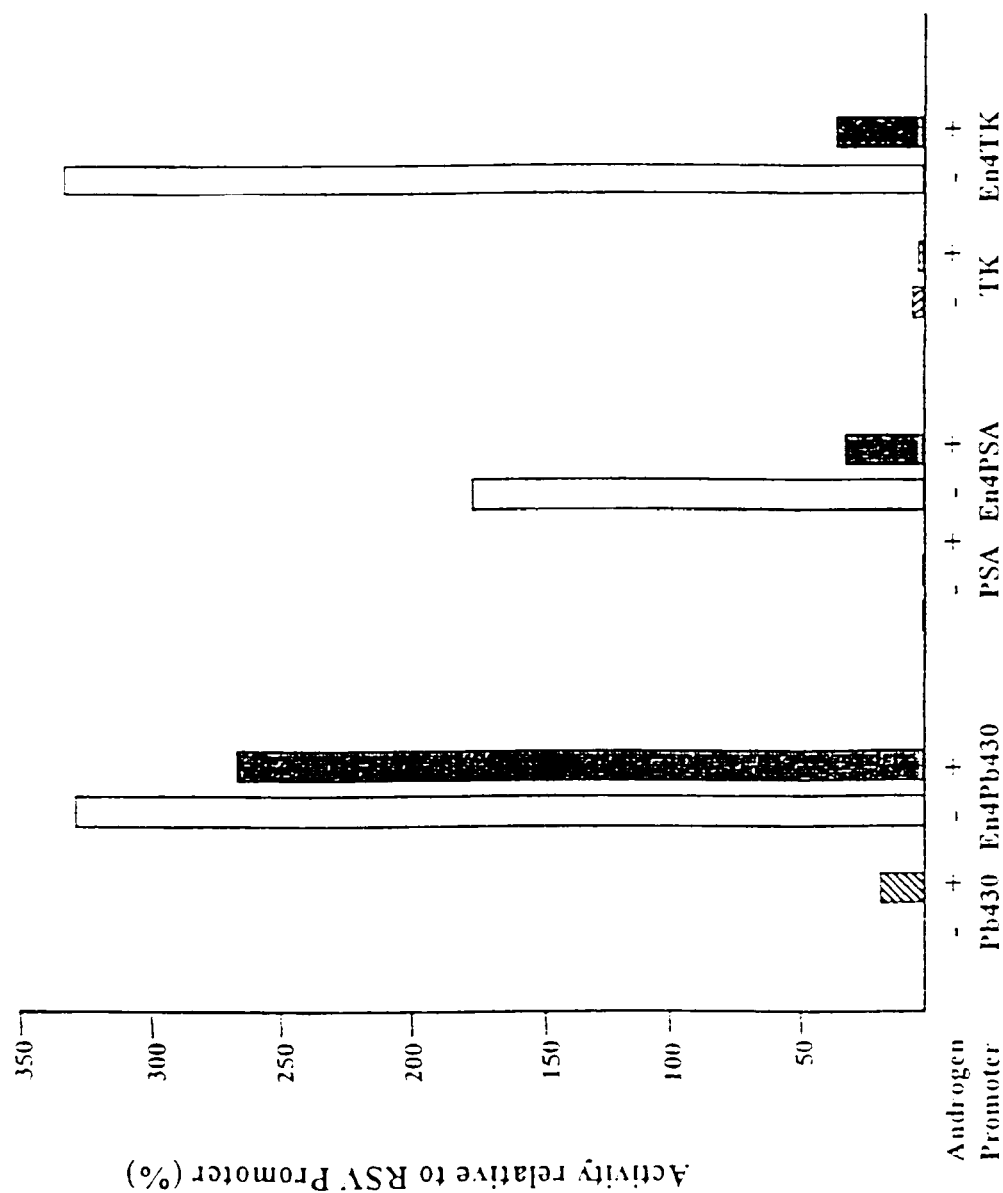

The different promoter and enhancer constructs were transfected into cell lines as shown and CAT reporter gene expression normalised against SAT expression determined. Activities are expressed as a percentage of the normalised expression of pRSV-CAT. Numbers above the columns indicate the relative enhancement of activity compared with expression from the respective promoter alone constructs. An * indicates that expression levels were too low to determine a ratio, FIG. 10. Effect of androgen on enhancement of heterologous promoters by PSM En4. Plasmids containing the different enhancer/promoter combinations as indicated below the graph were transfected into LNCaP cells that were maintained in medium that had been charcoal stripped to remove androgens or in equivalent medium to which the non-metabolizable androgen analogue R1881 had been added to 0.28 nM. The presence or absence of androgen is also indicated (– or +) below the graph. Activities were determined and expressed as described in FIG. 9.

FIG. 11. Sequence of 331 base pair core region of the PSME (SEQ ID NO:1).

Figure 12:
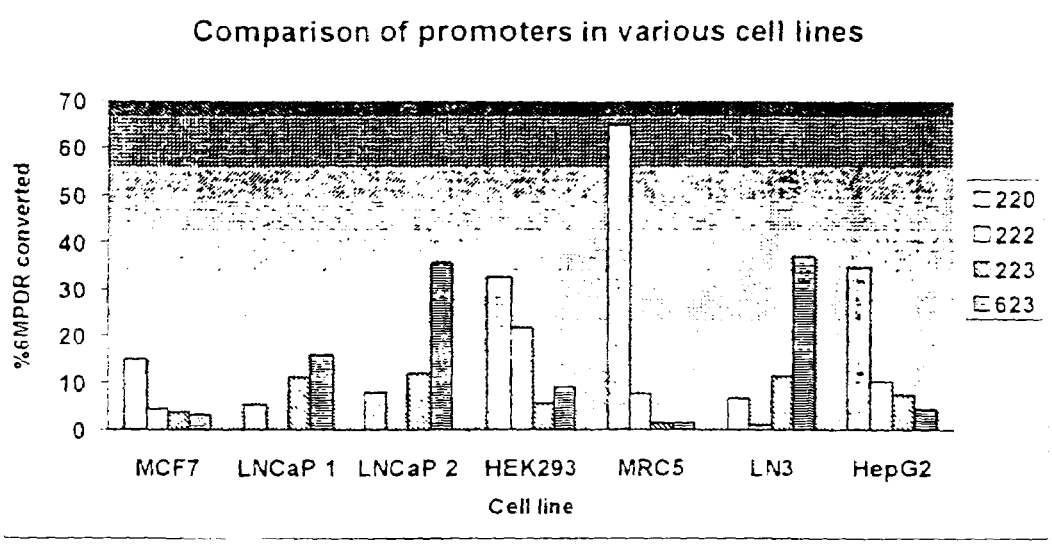

FIG. 12. Specificity of purine nucleoside phosphorylase (PNP) gene expression in viral constructs OAV223 and OAV623 (PSME and probasin promoter), OAV220 (PSME and RSV promoter) and OAV222 (PSME and CMV promoter).

Figure 13:
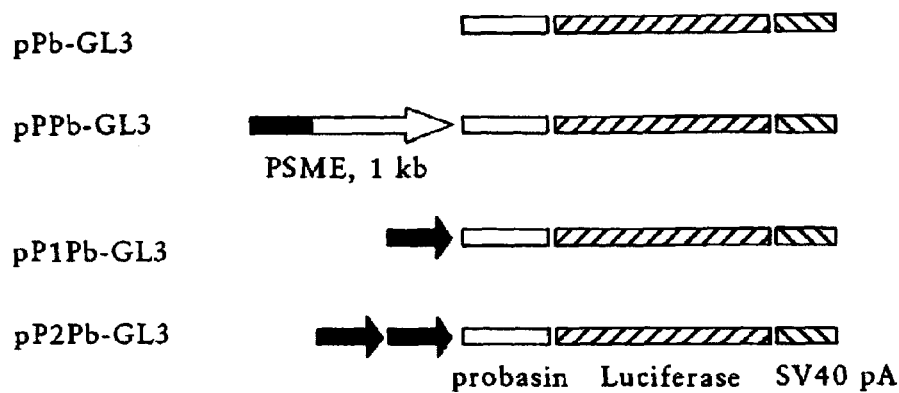

FIG. 13. A series of constructs (pPb-GL3, pPPb-GL3, pP1Pb-GL3 and pP2Pb-GL3) having a probasin promoter subcloned in front of the lubiferase reporter gene in the pGL3 vector.

Figure 14:
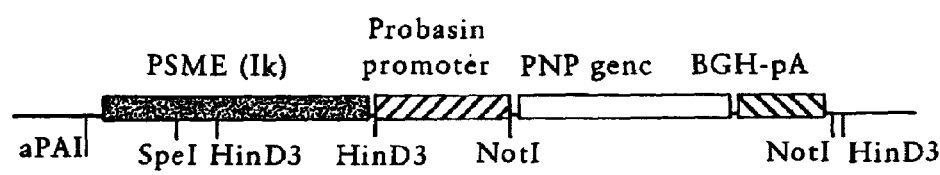
Figure 1:
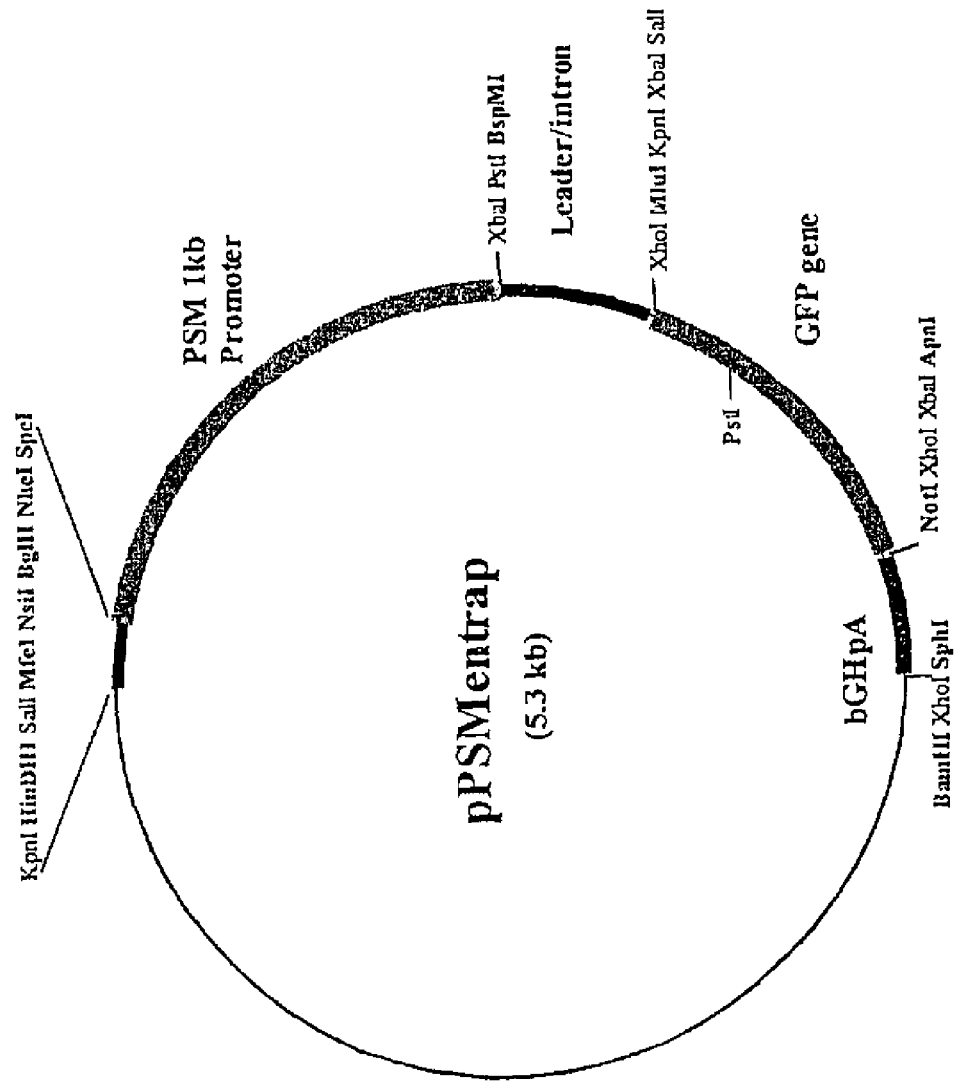

FIG. 14. A map of the pPPP (for Psm/probasi/PNP) construct.

EXPERIMENTAL DETAILS

Example 1

Isolation of PSMA Gene Enhancer Sequences

Analyses of the region upstream and encompassing the transcription start site of the PSMA gene (40) has shown that a 1 kb region directs expression of reporter genes in the prostate cell line LNCaP. This expression shows specificity for prostate cells when compared to that directed by the SV40 enhancer/promoter. Expression in LNCaP cells was about 75% of that directed by the SV40 enhancer/promoter. Comparison with another widely expressed promoter, that of the Rous sarcoma virus (RSV) has indicated that the SV40 enhancer/promoter is only very weakly active, <1% of RSV activity, in LNCaP cells (unpublished data). We have cloned regions encompassing up to 11 kb of sequences 5' to the PSMA transcription start site and tested their ability to provide increased reporter gene expression; no increased activity was seen relative to the 1 kb promoter region.

Figure 1:
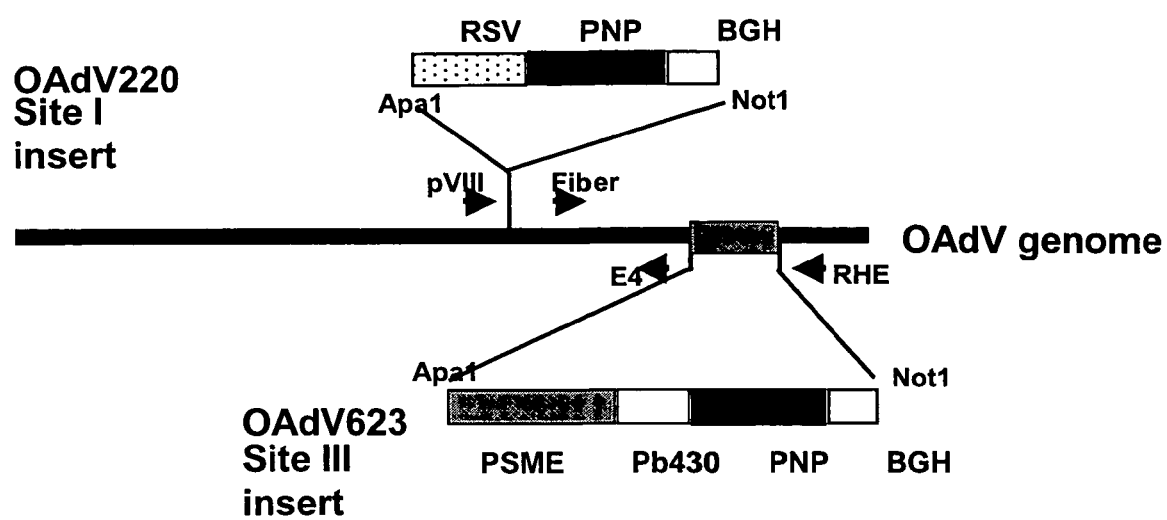
FIG. 1. pPSMentrap Vector. Key features of the vector are shown: the multicloning site (MCS) unique restriction sites upstream of the PSM 1k promoter region (PSM1k), leader sequence and intron (intron) derived from the pCI vector (Promega), the green fluorescent protein gene (GFP) and 3' sequences derived from the bovine growth hormone gene (bGHpA). A selection of useful restriction enzyme sites are shown; unique restriction enzyme sites are shown in bold.
Figure 2A:
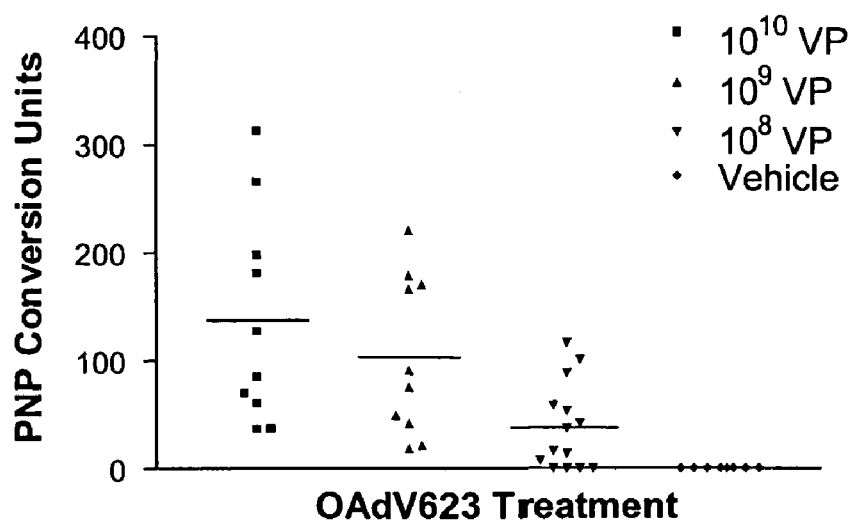
FIG. 2. Location of cloned PSM enhancer fragments: the map shows the location of the cloned enhancer fragments within intron 3 of the PSM gene. Base numbers (Genbank Accession No. AF007544) are indicated for the boundaries of intron 3 and for the ends of the cloned segments. The locations of the restriction sites SmaI (Sm), HinDIII (H) and SpeI (Sp) within the intron are shown. The arrows indicate the orientation of the cloned sequences within the pPSMentrap vector (see FIG. 3). The right hand end of the enhancer clone #1 is shown as a stippled box since this end of the clone has undergone rearrangement; The SmaI, HinDIII and SpeI sites are present in all three cloned regions.
Figure 2B:
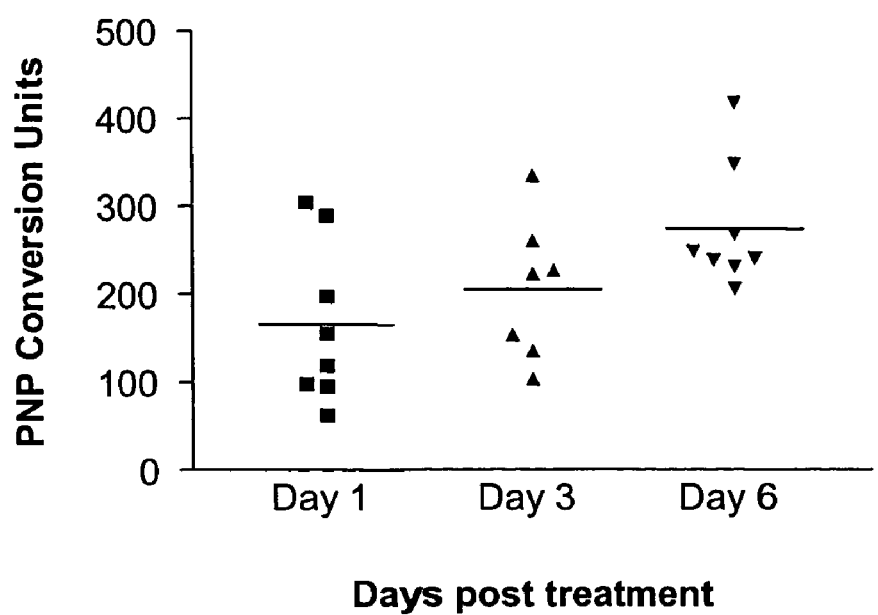
Figure 3A:
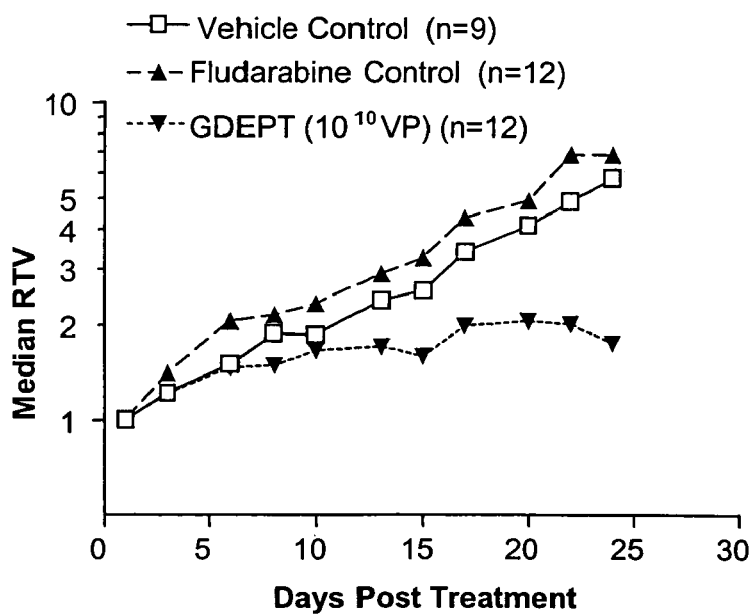
FIG. 3. Promoter and enhancer inserts in pPSMentrap: The positions of the PSM 1 kb promoter region and flanking restrictions sites in pPSMentrap are shown on the top line. To the right of the promoter sequences are the leader sequence and chimeric intron and GFP reporter gene. Below are shown maps of clones containing the En3 and En4 inserts. The sequences are in opposite orientation (note order of HinDIII and SpeI sites). Restriction sites are abbreviated as follows.
Figure 3B:
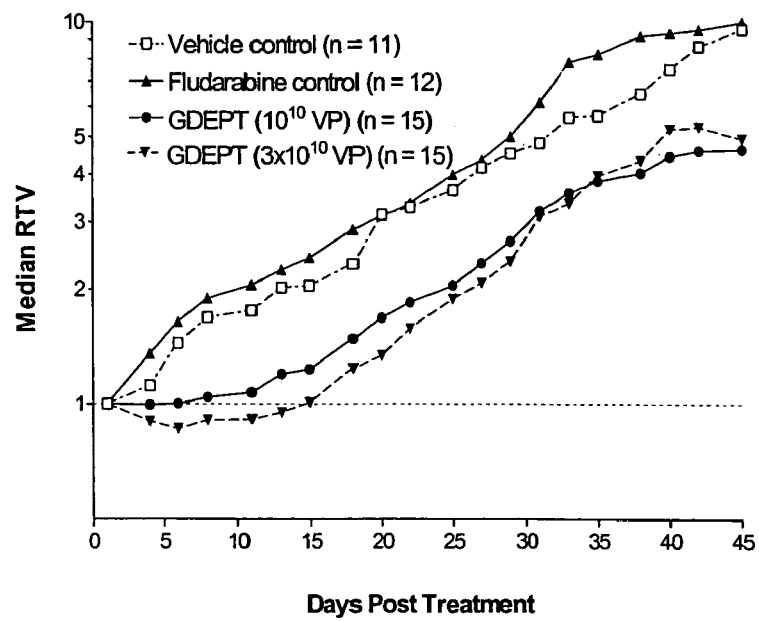
Figure 4A:
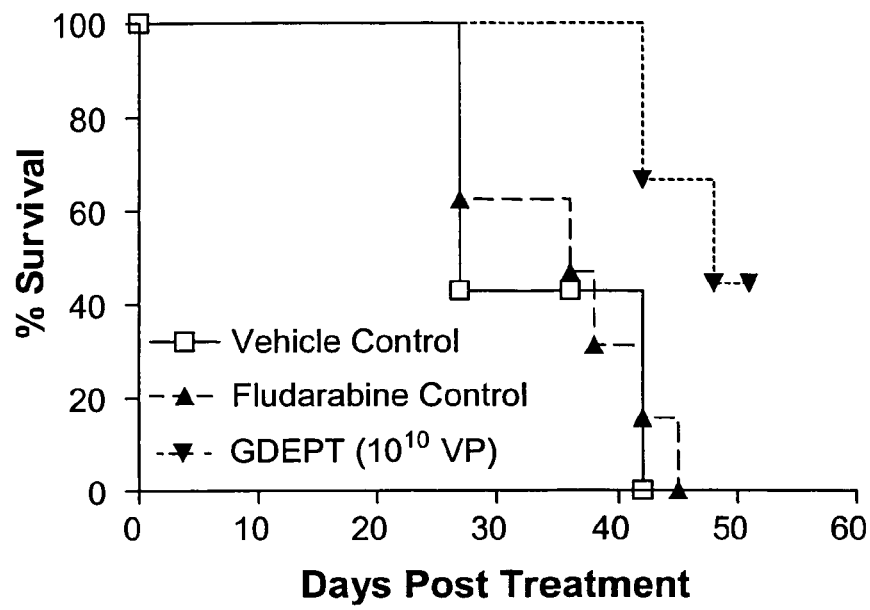
Figure 4B:
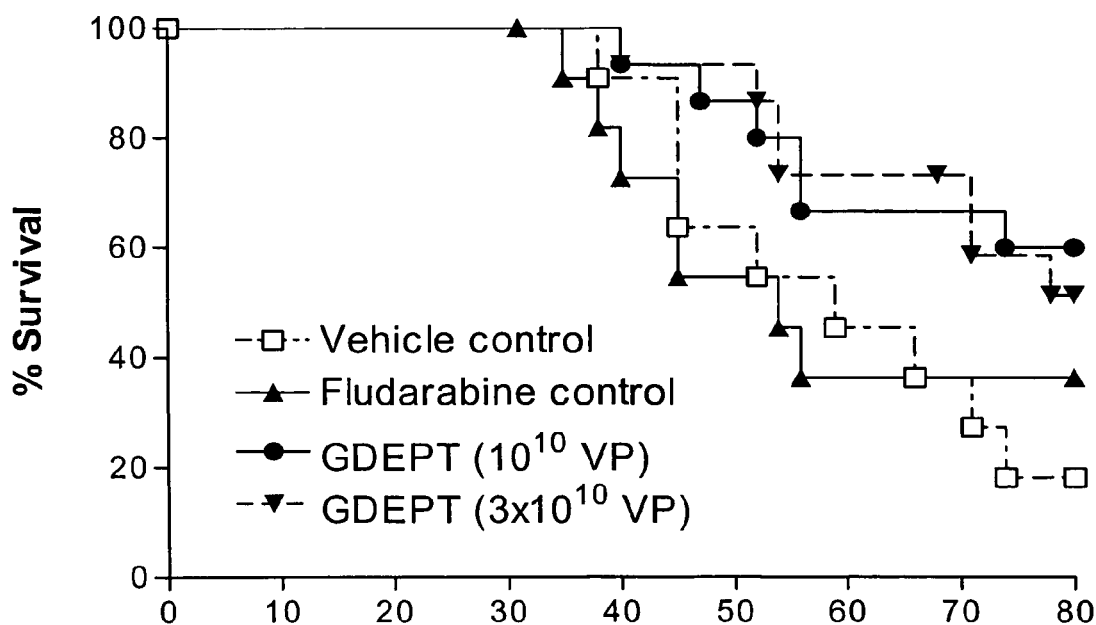

A strategy was developed to allow screening of DNA fragments for their ability to enhance transcription directed by the 1 kb proximal promoter region of the PSMA gene. The 1 kb promoter was cloned in front of the Green Fluorescent Protein (GFP) gene in the plasmid vector pPSMentrap shown in FIG. 1. Upstream of the promoter was inserted a polylinker region containing sites for cloning candidate fragments.

pPSMentrap contains the following elements: a polylinker containing restriction sites for the enzymes Kpn1, HindIII, SalI, MfeI, NsiI, BglI, NheI and SpeI, the PSMA promoter region stretching from base 1386 base 2560 (XbaI site) of the PSMA sequence (Genbank Accession No. AF007544), a chimeric intron as contained in the pC1 vector (Promega), the GFP gene, the 3' end polyadenylation signal from the bovine growth hormone gene and the plasmid backbone (including ampicillin resistance gene and origin of replication) from the pC1 vector.

A library of DNA sequences was prepared by digesting the bacteriophage P1 cosmid P1-683 which contains the 5' half and upstream flanking sequence of the PSMA gene (40). Cosmid DNA was digested for various of times with the enzyme Tsp509I which cuts at AATT sites generating a range of partial digestion products. These were separated by agarose gel electrophoresis and fragments in the size range 1 to 2 kb recovered and cloned into the MfeI site of the pPSMentrap vector. A library of about 600 individual clones was picked. Clones were grouped into 12 pools of 49 and DNA prepared from each pool using Qiagen columns and protocols. DNA (2.5 mg) from each pool was transfected into LNCaP cells in 3.5 cm dishes as previously described (1). After 48 to 72 hours, cell cultures were examined under a UV fluorescence microscope to identify any fluorescing cells. Positive pools were split into 7 by 7 matrices and DNA preparations made from the 7 clones in each row and each column. The transfections were repeated to identify positive sub-pools. Clones at the intersections of positive rows and columns were further screened individually to verify the expression of GFP. The three clones giving the strongest signals, #1, #3 and #4 were taken for further analysis.

Example 2

Location and Sequence Analysis of Enhancing Fragments

Figure 3:
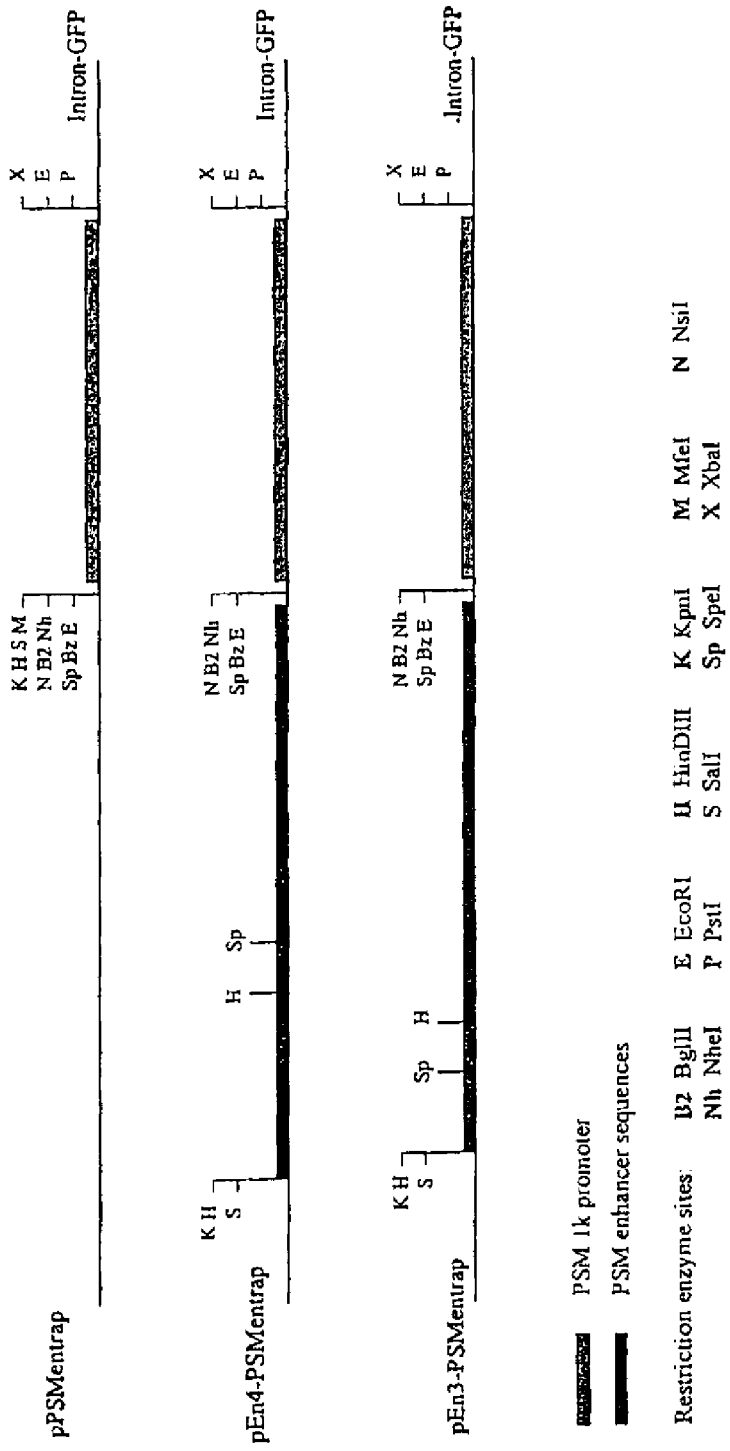

The inserts from the clones were re-cloned into pBluescriptSK+ (pBKSEn3 and pBKSEn4) and the sequences of their ends determined. All clones were found to originate from the third intron of the PSMA gene as shown in FIG. 2. The positions of both ends of clones #3 and #4 were identified as shown. The inserts in clones #3 and #4 were aligned in opposite orientations relative to the PSM promoter in the pPSMentrap vector as shown in FIG. 3. The clones share a common overlapping sequence of 1044 bp and extend in total over 2,530 bp. The third clone, #1, derived from the same region, one end being 6 bp upstream of the end of clone #4 and it also contained the SpeI and HinDIII sites contained in the region common to clones #3 and #4. It had, however, undergone some rearrangement on cloning and has not been further studied.

Example 3

Function of PSMA Enhancer Region

The activity of the PSMA enhancer region was first identified by visual inspection of fluorescence intensity of cells transfected with clones carrying PSMA gene inserts upstream of the PSM promoter. In these preliminary experiments it was also noted that the enhancer (clone #4) did not appear to function in the bladder cell line BL13 (not shown). In order to provide for quantitative determination of promoter and enhancer function, enhancers #3 and #4 (hereafter designated En3 and En4) in combination with the PSM 1 kb promoter were re-cloned into two different gene expression reporter systems.

Example 4

Expression Assayed in the pCAT3SAT System

The pCAT3SAT vector contains a modified bacterial chloramphenicol acetyl transferase reporter gene for determining promoter activity and a reference reporter gene, serine acetyl transferase, under the control of the RSV promoter in order to standardise CAT expression for transfection efficiency. It was prepared by cloning the serine acetyl transferase reporter gene from the pCATSAT plasmid (1) as a SalI/BamHI fragment into BamHI, SalI cut pCAT3 vector (Promega). Constructs. pPSM1k-C3S and pEn4PSM1k-C3S, containing the PSM promoter with or without the PSM enhancer fragment 4 (En4) were prepared by cloning the PSM enhancer/promoter fragments as SalI/PstI fragments from the pPSMentrap vector into pCAT3SAT cut at the XhoI and PstI sites in the polylinker upstream of the CAT gene (FIG. 4). A control construct containing the RSV promoter, pRSV-C3S, was also prepared by blunt end ligation of a NaeI to SacI fragment from pCATSAT (1) into the NheI site of pCAT3SAT (FIG. 4). Cell lines were transfected with the different constructs and CAT and SAT activities determined after 48 h as described (1). The normalised expression data are shown in FIG. 5.

In LNCaP cells an enhancement of expression of approximately 50 fold (from 0.33% to 15.7% of the activity of the RSV promoter) was seen when the En4 fragment was present upstream of the 1 kb PSM promoter. This expression showed a high level of specificity for LNCaP cells that express PSMA. Another prostate cell line, PC3, showed very low levels of expression from the PSM promoter either in the presence or absence of the enhancer. No expression above background was seen for three non-prostate cell lines (MCF-7, a breast cancer line, human embryonic kidney cells (HEK293) and the liver line HepG2). Low and variable expression was seen in a second breast cancer cell line T47-D2, with the enhancer/promoter construct showing about 10% of the activity seen in LNCaP cells.

Example 5

Expression Assayed in the Luciferase pGL3 System

Because of the low activity of the PSM 1 kb promoter in the CAT assay system, promoter and enhancer sequences were cloned into the pGL3 vector (Promega) which contains the luciferase reporter gene. The structure of the clones is shown in FIG. 6. pPSM1k-GL3 and pEn4PSM1k-GL3 were prepared by cloning KpnI to XbaI fragments from pPSM1k-C3S and pEn4PSM1k-C3S respectively into pGL3 cut with KpnI and NheI. pEn3PSM1k-GL3 was prepared by cloning the KpnI to NheI enhancer fragment of pEn3PSMentrap into pEn4PSM1k-GL3 cut with KpnI and NheI. To assay activity, mixtures of each pGL3 construct and the reference plasmid pRSVCAT (1) were transfected into a variety of cell lines by standard procedures as described previously (1). DNA concentrations were determined by image analysis of ethidium bromide stained gels and master mixes prepared in the ratio of 1.5 µg of pGL3 construct to 1 µg of pRSVCAT. The same master mixes were used for transfections into all cell lines. Cells were transfected with 2.5 µg of DNA mixes using standard procedures (1) and expression assayed after 48 hr. Extracts were prepared and luciferase activity determined using the Luciferase Assay System (Promega). CAT activities were determined as previously described. Luciferase expression levels were standardised with respect to the pRSVCAT reference plasmid and then standardised activities expressed as a proportion of that of pRSV-GL3/pRSV-CAT (FIG. 7).

In LNCaP cells expression from the PSM 1k promoter was strongly enhanced by both En3 and En4 enhancer sequences (about 260 fold) with expression levels directed by pEn3PSM1k and pEn4PSM1k being 15 and 15.7% that of the RSV promoter. In the non-PSMA-expressing prostate cell line PC3 a low level of enhancement (3.7 and 5.2 fold for En3 and En4 respectively) was seen, while there was no enhancer function in the other non-expressing prostate line, DU145. For a range of non-prostate cell lines tested, HepG2 liver cells, MRC5 primary lung fibroblasts. BL13 bladder carcinoma and human embryonic kidney HEK293 cells, essentially no activity was seen for the PSMA enhancer/promoter or promoter alone constructs. Activity is thus highly specific for the expressing prostate cell line LNCaP with partial enhancer function in one non-expressing prostate cell line PC-3.

Example 6

Characterisation of the Enhancer Element

To determine the extent of sequences required to provide enhancer activity a construct was prepared that contained all the sequences encompassed by clones En3 and En4 as well as constructs containing the overlapping region present in both cones (see FIG. 6). pEn3+4PSM1k-GL3 was prepared by cloning a KpnI to NdeI restriction fragment from pBK-SEn3 into pEn4PSM1k-GL3 cut with KpnI and NdeI. Clone pOverlapen3/4a was prepared by cloning the SalI to HinDIII fragment from pEn3PSMentrap into pBluescriptSK+, subsequently cloning the HindIII fragment from pEn4PSMentrap into the HinDIII site of the intermediate vector and verifying that it was in the correct orientation. The overlapping enhancer fragment was then cloned as a KpnI to EcoRI fragment in front of the PSM 1 kb promoter in pPSM1k-GL3 cut with KpnI and EcoRI. A construct with the overlapping region in the opposite orientation relative to the PSM promoter was likewise prepared by first cloning the SalI to HinDIII fragment from pEn4PSMentrap into pBluescriptSK+ followed by the HinDIII fragment from pEn3PSMentrap and then cloning the overlap region in front of the PSM promoter as a KpnI to EcoRI fragment.

The effectiveness of these constructs was compared with that of the PSM1k promoter alone and the En4/PSM1k promoter by transfection (as above) into LNCaP cells. Clones containing either orientation of the overlap region gave rise to expression levels similar to those containing En4 sequences. The construct containing the whole region encompassed by enhancers 3 and 4, however, gave significantly stronger expression. The level of expression was about half that of the RSV promoter.

Example 7

PSMA Enhancer Action on Other Promoters

The properties of the enhancer were further assessed by linking it to other promoters, both those active primarily in prostate cells, PSA and probasin, and a non-tissue-specific promoter, that of the herpesvirus thymidine kinase gene (TK). The structures of these promoter regions are shown in FIG. 8. For the PSA and probasin constructs the enhancer region, En4, was cloned as an NheI fragment from the pEn4PSM1k-C3S plasmid into the XbaI-cut plasmids pPSA630 CATSAT and pPb430 CATSAT respectively (by partial digestion with XbaI for the probasin construct). pPSA630CATSAT and pPb430 CATSAT have been described previously (1). The plasmid pTKCATSAT.1 was prepared by cloning the TK promoter region, bases −101 to +59, as a SalI to XhoI fragment into the SalI-cut vector pCATSAT.1 (1)[pCATSAT.1 is a derivative of pCATSAT (1) in which SalI, PstI and XhoI sites present upstream of the RSV promoter were removed or destroyed by XhoI and partial SalI digestion and religation]. pEn4TKCATSAT was prepared by cloning the SalI to BglII enhancer-containing fragment from pEn4PSMentrap into pTKCATSAT.1 cut with SalI and partially cut with BamHI.

All six plasmids were transfected into a number of cell lines and CAT and SAT reporter gene expression determined as described (1). Expression levels were standardised against that of the RSV promoter determined by transfection of a standard mixture of pRSVCAT and pRSVSAT plasmids as described (1). Results are shown in FIGS. 9a & b.

In LNCaP cells strong enhancement of the PSA, probasin and TK promoters was seen, with that for probasin being strongest. Levels of expression for all enhancer constructs were 2 to 3 times that of the RSV promoter. Since all promoters achieved similar levels of expression in the presence of the enhancer the "fold-enhancement" shown probably reflects differences in the level of non-enhanced expression from the different promoters, In PC3 prostate cells, which do not express PSMA, much reduced enhancement was seen, being 5 to 16 fold for the different promoters. This is similar to the results seen when the enhancer was joined with its own PSM promoter. Thus it appears that PC3 cells contain some factors that can interact with the PSM enhancer to activate transcription, but lack others, or do not have sufficient levels, to enable full enhancer function as is seen in LNCaP cells.

For the non-prostate cell lines, no enhancement was seen in HepG2 liver or BL13 bladder cells. Enhancement was seen in the embryonic kidney HEK293 cells. Low level enhancement (1.4, 1.5 fold) was seen for the PSA and TK promoters, while there was a stronger 9 fold enhancement of the probasin promoter. No enhancement by En4 of its homologous PSM promoter was seen in HEK293 cells (FIG. 7). Since the proximal kidney tubules are a site of low level PSMA expression, the expression seen in HEK293 cells may be biologically meaningful.

Example 8

PSM Enhancer Function Does not Require Androgens

The androgen requirement for activity of the PSM enhancer (En4) was studied when it was linked to two highly androgen-inducible promoters, those of the probasin and PSA genes and one constitutive promoter, TK. LNCaP cells were transfected with plasmid constructs using media that had been charcoal stripped to remove androgens. Cells were maintained in androgen-free medium or incubated in the presence of the non-metabolizable androgen analogue, R1881 added to 0.28 nM (1).For all promoters strong enhancement of expression was seen whether or not androgen was present in the medium. However, for all three constructs containing the PSM enhancer the level of expression actually decreased upon androgen addition. This suggests that the enhancer may contain sequences mediating the observed androgen-suppression of the endogenous PSMA gene.

Example 9

Sequences Required for Enhancer Function

In order to determine what sequence regions were critical for enhancer function a series of constructs were prepared in which different fragments from the PSME region were placed in front of the PSM promoter in the pPSM1k-GL3 plasmid. The sequences included in each construct are shown in the table below. The orientation of the enhancer sequences relative to the promoter is indicated as either F (forward, as for pEn4PSM1k-GL3) or R (reverse, as for pEn3PSM1k-GL3). Activity of these constructs was assayed following transfection into LNCaP cells along with the pRSVCAT control plasmid. Extracts were prepared and assayed 48 hr after transfection, luciferase activity normalised using the activity of the co-transfected pRSVCAT plasmid and expressed relative to that of pRSV-GL3 (Table below).

| Construct | Enhancer sequences | Activity in LNCaP cells (% RSV) |
| --- | --- | --- |
| pPSM1k-GL3 | | 0.2 |
| pEn4PSM1k-GL3 | 14760–16575 F | 16.0 |
| pEn3PSM1k-GL3 | 14045–15804 R | 15.7 |
| pEn3+4PSM1k-GL3 | 14045–16575 F | 39 |
| pEn3/4aPSM1k-GL3 | 14760–15804 F | 25 |
| pEn3/4bPSM1k-GL3 | 15804–14760 R | 21 |
| pEn4Sal/HindIIPSM1k-GL3 | 14760–15374 F | 20 |
| pEn3Sal/HindIIIPSM1k-GL3 | 15804–15369 R | 0.1 |
| pEnO2/770SpeIPSM1k-GL3 | 14760–15530 F | 24 |
| pEnO2/2/592NsiIPSM1k-GL3 | 14760–15352 F | 22 |
| pEnO2/445MscIPSM1k-GL3 | 14760–15205 F | 18 |
| pEnO2/331SmaIPSM1k-GL3 | 14760–15091 F | 26 |
| pEnO2/168NdeIPSM1k-GL3 | 14760–14930 F | 6 |
| pEnO1/722SmaIPSM1k-GL3 | 15092–15804 R | 0.3 |
| pEnO1/886NdeIIPSM1k-GL3 | 14925–15804 R | 0.4 |

These data indicate that most of the enhancer activity is contained within the 331 bp region encompassing bases 14760 to 15091. This region shows similar activity (26% that of RSV) to the En3 and En4 clones and to the approximately 1 kb region shared between them. Deletion from the 1 kb overlap region of either the left half or the entire 331 bp region (constructs pEnO1/722SmaIPSM1k-GL3 and pEnO1/886NdeIIPSM1k-GL3) eliminates enhancer activity, showing that this region is essential for activity. Elimination of the right half of the 331 bp region, leaving just 170 bp covering bases 14760 to 14930, leads to a marked reduction in activity.

Thus bases 14760 to 14930 are essential for PSME function, but sequences extending from 14760 to 15091, provide for much stronger enhancer activity. The sequence of the region is shown in FIG. 11 (SEQ ID NO. 1).

Example 10

PSME Core Enhancer Region Retains Cell-Type Specificity

Experiments were carried out on the 331 bp core region of the PSME that provides for enhancer function (bases 14760 to 15091) to determine whether this region retained its cell-type specificity. The activity of plasmids pPSM1k-GL3, pEnO2/331SmaIPSM1k-GL3 and pRSV-GL3 was assayed after transfection into a number of cell lines (Table below). Plasmids were co-transfected with an internal control pRSVCAT plasmid, extracts prepared and assayed 48 h after transfection. Luciferase activities were normalised using the activity of the pRSVCAT plasmid and are expressed relative to that of pRSV-GL3.

| | Activity Relative to the RSV promoter (%) | | | | |
| --- | --- | --- | --- | --- | --- |
| Construct | PC-3 | DU145 | MCF7 | MRC5 | HepG2 |
| pPSM1k-GL3 | 0.45 | 0.21 | 0.12 | 0.032 | 0.033 |
| pEnO2/331SmaIPSM1k-GL3 | 1.70 | 0.13 | 0.14 | 0.048 | 0.022 |

As for the longer enhancer fragments, partial enhancer activity was seen in the PC-3 prostate cancer cell line that does not express PSMA. For the other non-PSMA expressing prostate cell line, DU145, no enhancement of basal promoter activity was seen. Likewise the 331 bp PSME core region is not functional in three non-prostate cell lines. The core region thus retains the specificity of the PSME.

Example 11

Tandem Enhancer Sequences Provide for Greater Activity

A series of constructs were prepared in which the probasin promoter, with or without PSM enhancer fragments was subcloned in front of the luciferase reporter gene in the pGL3 vector. The structure of the constructs is shown in FIG. 13. The 430 bp probasin promoter fragment has been described previously (1) and was re-cloned from the pPB-CS plasmid (see FIG. 8). pPPb-GL3 contains the 1 kb overlapping enhancer region (bases 14760 to 15804). pP1Pb-GL3 and pP2PPb-GL3 contain one or two copies respectively of the 331 bp enhancer region (bases 14760 to 15091). All enhancer sequences are in the forward orientation.

The constructs were transfected, along with an RSVCAT control plasmid, into LNCaP, HEK293 or MCF-7 cells and expression measured in cell extracts prepared after 48 h incubation. Transfections were done in androgen-depleted media and luciferase activity corrected using the co-transfected RSVCAT internal control.

| | Relative Luciferase Activity | | |
|---|---|---|---|
| | LNCaP | HEK293 | MCF-7 |
| pPb-GL3 | 1.45 | 2.36 | 0.36 |
| pPPb-GL-3 | 246 | 2.17 | 1.09 |
| pP1Pb-GL-3 | 346 | 3.2 | 0.73 |
| pP2Pb-GL-3 | 798 | 1.8 | 5.75 |
| pRSV-GL-3 | 318 | 277 | 107 |

Greatest expression in LNCaP cells is seen with the double enhancer construct, being 2 to 3 times greater than those constructs with a single copy of the enhancer. Specificity of expression is largely maintained in these transfection studies, though the pP2Pb-GL3 construct shows an elevated level of expression in MCF-7 cells.

Example 12

Enhancer Function in a Viral Backbone

The properties of the PSME combined with the probasin promoter (its high activity and specificity and limited responsiveness to androgen levels) are particularly suitable for directing prostate-specific gene expression in gene therapy applications.

The *E. coli* purine nucleoside phosphorylase (PNP) gene in combination with the pro-drugs fludarabine or 6-methylpurine 2-deoxyriboside (6 MPDR) can be used to deliver enzyme pro-drug therapy (41). An expression cassette was prepared in the pGEM11 plasmid in which the PNP gene was placed under the control of the 1 kb PSME region (bases 14760 to 15804 in reverse orientation) adjacent to the 430 bp probasin promoter. A map of this construct (pPPP (for Psm/Probasin/PNP)) is shown in FIG. 14. The cassette in pGEM11 was partially sequenced to confirm its structure The expression cassette was subcloned by cutting with ApaI and NotI (partial digest for NotI) and inserting into ApaI/NotI cut ovine adenovirus (OAV) vectors (42). The expression cassette was inserted into two separate sites in the OAV plasmid. One isolate was prepared by cloning into OAV200 cut with ApaI and NotI (Site 1) to give clone pOAV223. In the other isolate, pOAV623, the cassette was cloned in an alternate site (Site 3) of the plasmid pOAV600 (42). Plasmid DNA was transfected into CSL503 cells as described (43) and viruses OAV223 and 623 recovered.

OAV223, OAV623 and two other viruses OAV220 and OAV222, that are equivalent to OAV223 except that the PNP gene is under the control of the RSV and CMV promoters respectively, were used to infect a variety of cell types as shown in FIG. 12. Cells were infected with the different viruses at a multiplicity of infection of $10^3$ opu/cell and PNP expression measured after 4 days (44). For each cell type an amount of lysate was used such that PNP expression from the most strongly expressing virus fell within the linear range of the assay. Thus, the absolute amount of PNP activity cannot be compared between cell lines but ratios of expression can be compared.

The data presented in FIG. 12 show that in the context of the viral backbone and OAV infection strong specificity of gene expression is maintained. Highest activity is seen from OAV623, then OAV223, being greater than that of the RSV promoter in LNCaP and LN3 prostate cancer cells. In all the non-prostate cell lines the RSV promoter (OAV220) provides strongest expression. The differential specificity of the PSME/Pb promoter versus the RSV promoter for prostate compared to non-prostate cells ranges from expression about 15 fold for HEK293 and MCF-7 through to 200 fold for MRC-5). Thus, in some cell types specificity is reduced in the OAV context but it is still substantial. In the following example retention of cell specificity of the PSME in combination with its own PSM promoter is also demonstrated when carried by a human adenovirus Type 5.

Example 13

Enhancer Function in Human Umbilical Artery Cells

PSMA has been shown to be expressed in the neovasculature of a range of tumour types, but not in normal vasculature. We have determined, using reverse transcriptase PCR, that PSMA is expressed in endothelial cells derived from the human umbilical artery (HUAECs) (data not shown). Other genes that are up-regulated in tumour vasculature are also expressed in HUAECs and related human umbilical vein cells (HUVECs), eg endoglin (45). Function of PSM regulatory sequences was therefore examined in these cells. The activity of the PSME coupled to the PSM 1 kb promoter was evaluated using a replication-defective adenovirus, human adenovirus Type 5, into which the expression cassette from the pPSMentrap vector with the En4 insert had been inserted. The virus, Ad525, carries the GFP gene with bovine growth hormone 3' polyadenylation sequences under the transcriptional control of PSME En4 sequences coupled to the PSM 1 kb promoter. A control virus, Ad526, in which the GFP gene was under the control of the ubiquitously-active EF-1 promoter was also used.

HUAECs and HUVECs were dissociated from umbilical arteries and cultured as described by Underwood and Bean (46) except that tissue culture dishes were coated with bovine, rather than chicken, fibronectin. HUACs, HUVECs, LNCaP and control human lung fibroblast MRC-5 cells were plated at $4 \times 10^4$ cells per chamber in fibronectin-coated microscope slide chambers. The following day they were infected with $5 \times 10^8$ optical particle units per chamber of either Ad525 or Ad526. Expression of the GFP gene was monitored by fluorescence microscopy 3 days after infection for the control Ad526 virus and after 6 days for the PSME driven Ad525.

Expression from the control virus (EIF, OAV526) was strong in all cell types. For the En4PSMGFP virus, clear expression was seen in HUAECs and LNCaP cells, weaker expression in HUVECs, but no expression could be detected in MRC-5 cells. The combination of PSME and the PSM promoter is thus able to specifically drive gene expression in these arterial cells that express the endogenous PSM gene and should prove useful in directing expression to tumour vasculature.

It will be appreciated by persons skilled in the art that numerous variations and/or modifications may be made to the invention as shown in the specific embodiments without departing from the spirit or scope of the invention as broadly described. The present embodiments are therefore, to be considered in all respects as illustrative and not restrictive.

REFERENCES

1. Brookes, D. E., D. Zandvliet, F. Watt, P. J. Russell and P. L. Molloy (1998) relative activity and specificity of promoters from prostate-expressed genes. The Prostate 35: 18–26

2. Cleutjens, K. B. J. M., C. C. E. M. Vaneekelen, H. A. G. M. Vanderkorput, A. O. Brinkmann and J. Trapman. (1996). "Two androgen response regions cooperate in steroid hormone regulated activity of the prostate-specific antigen promoter." J Biol. Chem. 271(11): 6379–6388.
3. Riegman. P. H. J., R. J. Vliestra, J. A. G. M. van der Korput, A. O. Brinkmann and J. Trapman. (1991). "The promoter of the prostate-specific antigen gene contains a functional androgen responsive element." Molec. Endocrinology. 5(12): 1921–1930.
4. Murtha, P., D. J. Tindall and C. Y. F. Young. (1993). "Androgen induction of a human Prostate-Specific kallikrein, hKLK2-characterization of an androgen response element in the 5' promoter region of the gene." Biochemistry. 32(25): 6459–6464.
5. Claessens, F., N. K. Rushmere, P. Davies, L. Celis, B. Peeters and W. A. Rombauts. (1990). "Sequence-specific binding of androgen-receptor complexes to prostatic binding protein genes." Mol. Cell. Endocrinol. 74: 203–212.
6. Rushmere, N. K., M. G. Parker and P. Davies. (1987). "Androgen-receptor binding regions of an androgen responsive gene." Mol. Cell. Endocrinol. 51: 259–265
7. Kasper, S., P. S. Rennie, N. Bruchovsky, P. C. Sheppard, H. Cheng, L. Lin, R. P. C. Shiu, R. Snoek and R. J. Matusik. (1994). "Cooperative binding of androgen receptors to two DNA sequences is required for androgen induction of the probasin gene." J. Biol. Chem. 269(50): 31763–31769.
8. Rennie, P. S., N. Bruchovsky, K. J. Leco, P. C. Sheppard, S. A. McQueen, H. Cheng, R. Snoek, A. Hamel, M. E. Bock, B. S. MacDonald, B. E. Nickel, C. Chang, S. Liao, P. A. Cattini and R. J. Matusik. (1993). "Characterization of two cis-acting DNA elements involved in the regulation of the probasin gene." Molec. Endocrinol. 7(1): 23–36.
9. Virkkunen, P., P. Hedberg, J. J. Palvimo, E. Birr, K. Porvari, M. Ruokonen, P. Taavitsainen, O. A. Jänne and P. Vihko. (1994). "Structural comparison of human and rat prostate-specific acid phosphatase genes and their promoters: identification of putative androgen response elements." Biochem. and Biophys. Res. Commun. 202(1): 49–57.
10. Celis, L., F. Claessens, B. Peeters. W. Heyns, G. Verhoeven and W. Rombauts. (1993). "Proteins interacting with an androgen-responsive unit in the C3(1) gene intron." Mol. Cell. Endocrinol. 94: 165–172.
11. Ho. K. C., K. B. Marschke, J. A. Tan, S. G. A. Power. E. M. Wilson and F. S. French. (1993). "A complex response element in intron-1 of the Androgen-Regulated 20-kDa protein gene displays cell Type-Dependent androgen receptor specificity." J Biol. Chem. 268(36): 27226–27235.
12. Zhang, Y.-L., M. G. Parker and O. Bakker. (1990). "Tissue-specific differences in the binding of nuclear proteins to a CCAAT motif in the promoter of the androgen-regulated C3 gene." Molec. Endocrinol. 4(8): 1219–1225.
13. Allison, J., Y.-L. Zhang and M. G. Parker. (1989). "Tissue-specific and hormonal regulation of the gene for rat prostatic steroid-binding protein in transgenic mice." Mol. Cell. Biol. 9: 2254–2257.
14. Maroulakou, I. G., M. Anver, L. Garrett and J. E. Green. (1994). "Prostate and mammary adenocarcinoma in transgenic mice carrying a rat c3(1) simian virus 40 large tumor antigen fusion gene." Proc Natl Acad Sci USA. 91(23): 11236–11240.
15. Greenberg, N. M., F. J. Demayo, P. C. Sheppard, R. Barrios, R. Lebovitz, M. Finegold, R. Angelopoulou, J. G. Dodd, M. L. Duckworth, J. M. Rosen and R. J. Matusik. (1994). "The rat probasin gene promoter directs hormonally and developmentally regulated expression of a heterologous gene specifically to the prostate in transgenic mice." Mol Endocrinol. 8(2): 230–239.
16. Matusik, R. J. Isolated DNA mol. contg. an androgen responsive element comprising a 5'-flanking region of the rat probasin gene, used to generate transgenic animals and for human prostate cancer therapy. International publication no. WO 94/03594
17. Greenberg, N. M., F. Demayo, M. J. Finegold, D. Medina, W. D. Tilley, J. O. Aspinall, G. R. Cunha, A. A. Donjacour, R. J. Matusik and J. M. Rosen. (1995). "Prostate cancer in a transgenic mouse." Proc Natl Acad Sci USA. 92(8): 3439–3443.
18. Gingrich, J. R. R. J. Barrios, M. W. Kattan, H. S. Nahm, M. J. Finegold and N. M. Greenberg (1997) Androgen independent prostate cancer progression in the TRAMP model. Cancer Res. 57: 4687–4691.
19. Schaffner, D. L., R. Barrios, M. R. Shaker, S. Rajagopalan, S. L. Huang, D. J. Tindall, C. Y. F. Young, P. A. Overbeek, R. M. Lebovitz and M. W. Lieberman. (1995). "Transgenic mice carrying a PSArasT24 hybrid gene develop salivary gland and gastrointestinal tract neoplasms." Lab Invest. 72(3): 283–290.
20. Belldegrun, A. S. and S. Pang. "Nucleic acid contg. prostate specific antigen promoter useful for prodn. of heterologous protein, or for gene therapy of prostatic cancer.": International publicationno. WO 96/14875
21. Pang, S., S. Taneja, K. Dardashti, P. Cohan, R. Kaboo, M. Sokoloff, C.-L. Tso, J. B. Dekernion and A. S. Belldegrun. (1995). "Prostate tissue specificity of the prostate-specific antigen promoter isolated from a patient with prostate cancer." Hum. Gene Ther. 6: 1417–1426.
22. Henderson, D. R. Transcriptional regulator specific for cells expressing prostate specific antigen used to express toxins, immunostimulants or anti-sense cpds., for treatment and prevention of prostatic cancer or hypertrophy. Internation publication no. WO 95/19434
23. Schuur, E. R., G. A. Henderson, L. A. Kmetec, J. D. Miller, H. G. Lamparski and D. R. Henderson. (1996). "Prostate-specific antigen expression is regulated by an upstream enhancer." J Biol. Chem. 271(12): 7043–7051.
24. Rodriguez, R., E. R. Schuur, H. Y. Lim, G. A. Henderson, J. W. Simons and D. R. Henderson (1997) Prostate attenuated replication competent adenovirus (ARCA) CN706: a selective cytotoxic for prostate-specific antigen-positive prostate cancer cells. Cancer Res.57: 2559–2563.
25. Horoszewicz, J. S., E. Kawinski and G. P. Murphy (1987) Monoclonal antibodies to a new antigenic marker in epithelial prostatic cells and serum of prostate cancer patients. Anticancer Res. 7: 927–936.
26. Troyer, J. K., Q. Feng, M. L. Beckett and G. L. Wright Jr. (1995) Biochemical characterization and mapping of the 7E11-C5.3 epitope of the prostate specific membrane antigen. Urol. Oncol. 1: 29–37.
27. Troyer, J. K., M. L. Beckett and G. L. Wright Jr. (1997) Location of the prostate specific membrane antigen in the LNCaP prostate carcinoma cell line. The Prostate 30: 232–242.
28. Liu, H., P. Moy, S. Kim, Y. Xia, A. Rajasekaran, V. Navarro, B. Knudsen and N. H. Bander (1997) Monoclonal antibodies to the extracellular domain of prostate-specific membrane antigen also react with tumor vascular endothelium. Cancer Res. 57: 3629–3634.
29. Murphy, G. P., W. J. Tino, E. H. Holmes. A. L. Boynton, S. J. Erikson, R. J. Bowes, R. J. Barren, B. A. Tjoa, S. L. Misrock, H. Ragde and G. M. Kenny. (1996) Measurement of prostate-specific membrane antigen in he serum with a new antibody. The Prostate 28: 266–271.
30. Israeli, R. S., C. T. Powell, W. R. Fair and W. D. Heston (1993) Molecular cloning of a complementary DNA encoding a prostate-specific membrane antigen. Cancer Res. 53: 227–230.
31. Su, S. L., I. P. Huang W. R. Fair and W. D. W. Heston (1995) Alternatively spliced variants of prostate-specific membrane antigen RNA: ratio of expression as a potential measurement of progression. Cancer Res. 55: 1441–1443.
32. Pinto, J. T., B. P. Suffoletto, T. M. Berzin, C. H. Qiao, S. Lin, W. P. Tong, F. May, B. Mukherjee and W. D. W. Heston (1996) Prostate-specific membrane antigen: a novel folate hydrolase in human prostatic carcinoma cells. Clinical Cancer Res. 2: 1445–1451.
33. Carter, R. E., A. R. Feldman and J. T. Coyle (1996) Prostate-specific membrane antigen is a hydrolase with substrate and pharmacologic characteristics of a neuropeptidase. Proc. Natl. Acad. Sci. USA 93: 749–753.
34. Wright, G. L., C. Haley, M. L. Beckett and P. F. Schellhammer (1995) Expression of prostate-specific membrane antigen in normal, benign, and malignant prostate tissues. Urol. Oncol. 1: 16–28.
35. Lopes, D., W. L. Davis, M. J. Rosenstraus, Uveges, A. J. and S. C. Gilman (1990) Immunohistochemical and pharmacokinetic characterization of the site-specific immunoconjugate CYT-356 derived from the antiprostate monoclonal antibody 7E11-C5. Cancer Res. 50: 6423–6429.
36. Silver, D. A., I. Pellicer, W. R. Fair, W. D. Heston and C. Cordon-Cardo (1997) Prostate-specific membrane antigen expression in normal and malignant tissues. Clin. Cancer Res. 3: 81–85.
37. Israeli, R. S., C. T. Powell, J. G. Corr, W. R. Fair and W. D. W. Heston (1994) Expression of the prostate-specific membrane antigen. Cancer Res. 54: 1807–1811.
38. Wright, G. L. Jr., M. Grob. C. Haley, K. Grossman, K. Newhall, D. Petrylak, J. Troyer, A. Konchuba, P. F. Schellhammer and R. Moriarty (1996) Upregulation of prostate-specific membrane antigen after androgen-deprivation therapy. Urology 48: 326–334.
39. Fair. W. R., R. S. Israeli and W. D. W. Heston (1997) Prostate-specific membrane antigen. The Prostate 32: 140–148.
40. O'Keefe, D. S., S. L. Su, D. J. Bacich, Y. Horiguchi, Y. Luo, C. T. Powell, D. Zandvliet. P. J. Russell, P. L. Molloy, N. J. Nowak, T. B. Shows, C. Mullins, R. A. Vonder Haar, W. R. Fair and W. D. W. Heston (1998) Mapping, genomic organization and promoter analysis of the human prostate-specific membrane antigen gene. Biochim et Biophys. Acta 1443: 113–127.
41. Lockett, L. J., Molloy, P. L., Russell, P. J. and Both, G. W. (1997) Relative Efficiency Of Tumour Cell Killing In Vitro By Two Enzyme-Prodrug Systems Delivered By Identical Adenovirus Vectors. Clinical Cancer Res. 3:2075–2080.
42. Xu ZZ, Hyatt A, Boyle DB, Both GW. (1997) Construction of ovine adenovirus recombinants by gene insertion or deletion of related terminal region sequences. Virology 230:62–71.
43. Vrati S, Macavoy ES, Xu ZZ, Smole C. Boyle DB, Both GW. (1996) Construction and transfection of ovine adenovirus genomic clones to rescue modified viruses. Virology 220:200–203.
44. Martiniello-Wilks, R., Garcia-Aragon, J., Daja, M., Russell, P., Both, G. W, Molloy, P. L., Lockett, L. J. and Russell, P. J. (1998) Human Gene Therapy 9: 99–106.
45. Graulich W., Nettlebeck, D. M., Fischer D., Kissell T and R. Muller (1999) Cell type specificity of the human endoglin promoter. Gene 227; 55–62.
46. Underwood, P. A. and P. A. Bean (1996) The effect of vitronectin and other extracellular matrix molecules on endothelial expansion and plasminogen activation. Cells and Materials 6: 193–207.

What is claimed is:

1. A recombinant polynucleotide comprising at least one enhancer element obtained from intron 3 of the PSM gene operably linked to a sequence encoding a heterologous polypeptide.

2. A recombinant polynucleotide according to claim 1 in which the recombinant polynucleotide further comprises a promoter.

3. A recombinant polynucleotide according to claim 1 in which the enhancer element comprises a sequence comprising nucleotides 14760 to 14930 as shown in FIG. 11 or a sequence which hybridises thereto under high stringency.

4. A recombinant polynucleotide according to claim 1 in which the enhancer element comprises a sequence comprising nucleotides 14760 to 15091 as shown in FIG. 11 or a sequence which hybridises thereto under high stringency.

5. A recombinant polynucleotide according to claim 1 in which the polynucleotide comprises two or more enhancer elements obtained from intron 3 of the PSM gene.

6. A recombinant polynucleotide according to claim 2 in which the promoter is located upstream from and is operably linked to the sequence encoding the heterologous polypeptide.

7. A recombinant polynucleotide according to claim 2 in which the promoter is selected from the group consisting of a herpes virus thymidine kinase (TK) promoter, a Rous sarcoma virus (RSV) promoter, a promoter active in the prostate, or a promoter active in the vascular endothelium.

8. A recombinant polynucleotide according to claim 6 in which the enhancer element comprises:
   (a) a sequence comprising nucleotides 14,045 to 15,804, nucleotides 14,760 to 15,804, nucleotides 14,760 to 16,575 or nucleotides 14,045 to 16,575 of the PSM gene; or
   (b) a nucleic acid sequence which hybridises under high stringency 0.1×SSC and 0.1% (w/v) SDS at 50° C. wash conditions to a sequence defined in paragraph (a).

9. A recombinant polynucleotide according to claim 7 in which the promoter active in the prostate is selected from the group consisting of a probasin promoter, a PSM promoter and a PSA promoter.

10. A recombinant polynucleotide according to claim 9 in which the promoter active in the prostate is a PSM promoter.

11. A recombinant expression cassette comprising at least one enhancer element obtained from intron 3 of the PSM gene operably linked to a promoter, and an insertion site into which a coding sequence is optionally inserted, the insertion site being operably linked to and downstream of the promoter.

12. A recombinant expression cassette according to claim 11 in which the enhancer element is upstream of the promoter.

13. A recombinant expression cassette according to claim 11 in which the enhancer element comprises
   (a) a sequence comprising nucleotides 14,045 to 15,804, nucleotides 14,760 to 15,804, nucleotides 14,760 to 16,575 or nucleotides 14,045 to 16,575 of the PSM gene; or
   (b) a nucleic acid sequence which hybridises under high stringency 0.1×SSC and 0.1% (w/v) SDS at 50° C. wash conditions to a sequence defined in paragraph (a).

14. A recombinant expression cassette according to claim 11 in which the enhancer element comprises a sequence comprising nucleotides 14760 to 14930 as shown in FIG. 11 or a sequence which hybridises thereto under high stringency 0.1×SSC and 0.1% (w/v) SDS at 50° C. wash conditions.

15. A recombinant expression cassette according to claim 11 in which the enhancer element comprises a sequence comprising nucleotides 14760 to 15091 as shown in FIG. 11 or a sequence which hybridises thereto under high stringency 0.1×SSC and 0.1% (w/v) SDS at 50° C. wash conditions.

16. A recombinant expression cassette according to claim 11 in which the expression cassette comprises two or more enhancer elements obtained from intron 3 of the PSM gene.

17. A recombinant expression cassette according claim 11 in which the expression cassette comprises a dimer or higher multimer comprising two or more enhancer elements obtained from intron 3 of the PSM gene.

18. A recombinant expression cassette according to claim 11 in which the promoter is selected from the group consisting of a herpes virus thymidine kinase (TK) promoter, a Rous sarcoma virus (RSV) promoter, a promoter active in the prostate, or a promoter active in the vascular endothelium.

19. A recombinant expression cassette according to claim 11 in which the expression cassette further comprises a polyadenylation signal located downstream from and operably linked to the coding sequence or downstream from the insertion site.

20. A recombinant expression cassette according to claim 18 in which the promoter active in the prostate is selected from the group consisting of a probasin promoter, a PSM promoter and a PSA promoter.

21. A recombinant expression cassette according to claim 20 in which the promoter active in the prostate is a PSM promoter.

22. A recombinant expression cassette according to claim 19 in which the polyadenylation signal is the SV40 polyadenylation signal or the bovine growth hormone polyadenylation signal.

23. A vector comprising a gene encoding a selectable marker and an isolated nucleic acid molecule, the nucleic acid molecule having enhancer activity and comprising:
   (a) a sequence comprising nucleotides 14760 to 14930 as shown in FIG. 11, or
   (b) a nucleic acid sequence which hybridises under high stringency 0.1×SSC and 0.1% (w/v) SDS at 50° C. wash conditions to the sequence defined in Paragraph (a).

24. A vector according to claim 23 in which the vector is a human adenovirus Type 5 or ovine adenovirus.

25. A method for directing expression of a coding sequence in a prostate cell, the method comprising introducing into the cell a recombinant expression cassette comprising at least one enhancer element obtained from intron 3 of the PSM gene, a promoter, and a coding sequence, wherein the enhancer element and promoter direct expression of the coding sequence.

26. A method according to claim 25 in which the enhancer element comprises
   (a) a sequence comprising nucleotides 14,045 to 15,804, nucleotides 14,760 to 15,804, nucleotides 14,760 to 16,575 or nucleotides 14,045 to 16,575 of the PSM gene; or
   (b) a nucleic acid sequence which hybridises under high stringency 0.1×SSC and 0.1% (w/v) SDS at 50° C. wash conditions to a sequence defined in paragraph (a).

27. A method according to claim 25 in which the enhancer element comprises a sequence comprising nucleotides 14760 to 14930 as shown in FIG. 11 or a sequence which hybridises thereto under high stringency 0.1×SSC and 0.1% (w/v) SDS at 50° C. wash conditions.

28. A method according to claim 25 in which the enhancer element comprises a sequence comprising nucleotides 14760 to 15091 as shown in FIG. 11 or a sequence which hybridises thereto under high stringency 0.1×SSC and 0.1% (w/v) SDS at 50° C. wash conditions.

29. A method according to claim 25 in which the promoter is selected from the group consisting of a herpes virus thymidine kinase (TK) promoter, a Rous sarcoma virus (RSV) promoter, or a promoter active in the prostate.

30. The method according to claim 25 in which the coding sequence encodes a toxin, a protein involved in viral replication, or an enzyme which converts a prodrug to a toxic drug.

31. A method according to claim 29 in which the promoter active in the prostate is selected from the group consisting of a probasin promoter, a PSM promoter and a PSA promoter.

32. A method according to claim 31 in which the promoter active in the prostate is a PSM promoter.

33. A method for the treatment of prostate cancer which method comprises administering to a subject a recombinant expression cassette comprising at least one enhancer element obtained from intron 3 of the PSM gene, a promoter, and a coding sequence, wherein the enhance element and promoter direct expression of the coding sequence.

34. A method according to claim 33 in which the enhancer element comprises
(a) a sequence comprising nucleotides 14,045 to 15,804, nucleotides 14,760 to 15,804, nucleotides 14,760 to 16,575 or nucleotides 14,045 to 16,575 of the PSM gene; or
(b) a nucleic acid sequence which hybridises under high stringency 0.1×SSC and 0.1% (w/v) SDS at 50° C. wash conditions to a sequence defined in paragraph (a).

35. A method according to claim 33 in which the enhancer element comprises a sequence comprising nucleotides 14760 to 14930 as shown in FIG. 11 or a sequence which hybridises thereto under high stringency 0.1×SSC and 0.1% (w/v) SDS at 50° C. wash conditions.

36. A method according to claim 33 in which the enhancer element comprises a sequence comprising nucleotides 14760 to 15091 as shown in FIG. 11 or a sequence which hybridises thereto under high stringency 0.1×SSC and 0.1% (w/v) SDS at 50° C. wash conditions.

37. A method according to claim 33 in which the promoter is selected from the group consisting of a herpes virus thymidine kinase (TK) promoter, a Rous sarcoma virus (RSV) promoter, a promoter active in the prostate, or a promoter active in the vascular endothelium.

38. A method according to claim 33 in which the coding sequence encodes the enzyme purine nucleoside phosphorylase (PNP).

39. The method according to claim 33 in which the coding sequence encodes a toxin, a protein involved in viral replication, or an enzyme which converts a prodrug to a toxic drug.

40. A method according to claim 37 in which the promoter active in the prostate is selected from the group consisting of a probasin promoter, a PSM promoter and a PSA promoter.

41. A method according to claim 40 in which the promoter active in the prostate is a PSM promoter.

42. A method for directing in vitro expression of a coding sequence in a cell, the method comprising introducing into the cell a recombinant expression cassette comprising at least one enhancer element obtained from intron 3 of the PSM gene, a promoter, and a coding sequence, wherein the enhancer element and promoter direct expression of the coding sequence.

43. The method according to claim 30 in which the coding sequence encodes an enzyme which converts a prodrug to a toxic drug.

44. The method according to claim 43 in which the enzyme is purine nucleoside phosphorylase (PNP).

45. The method according to claim 39 in which the coding sequence encodes an enzyme which converts a prodrug to a toxic drug.

46. The method according to claim 45 in which the enzyme is purine nucleoside phosphorylase (PNP).

47. A vector comprising a gene encoding a selectable marker and an isolated nucleic acid molecule, the nucleic acid molecule having enhancer activity and comprising:
(a) a sequence comprising nucleotides 14760 to 15091 as shown in FIG. 11, or
(b) a nucleic acid sequence which hybridises under high stringency 0.1×SSC and 0.1% (w/v) SDS at 50° C. wash conditions to the sequence defined in paragraph (a).

48. A vector according to claim 47 in which the vector is a human adenovirus Type 5 or ovine adenovirus.

* * * * *

UNITED STATES PATENT AND TRADEMARK OFFICE
CERTIFICATE OF CORRECTION

PATENT NO. : 7,074,400 B1  Page 1 of 1
APPLICATION NO. : 09/914651
DATED : July 11, 2006
INVENTOR(S) : Peter Laurence Molloy et al.

It is certified that error appears in the above-identified patent and that said Letters Patent is hereby corrected as shown below:

On the title page

Under section (73) Assignee, change "The Commonwealth of Australia, Campbell (AU)" to -- Commonwealth Scientific and Industrial Research Organisation, Campbell (AU) --

Under section (87) PCT Pub. Date:, change "Sep. 9, 2000" to -- Sep. 8, 2000 --

Signed and Sealed this

Twenty-sixth Day of December, 2006

JON W. DUDAS
*Director of the United States Patent and Trademark Office*

UNITED STATES PATENT AND TRADEMARK OFFICE
CERTIFICATE OF CORRECTION

PATENT NO.         : 7,074,400 B1
APPLICATION NO. : 09/914651
DATED              : July 11, 2006
INVENTOR(S)        : Peter Laurence Molloy It is certified that error appears in the above-identified patent and that said Letters Patent is hereby corrected as shown below:

Delete drawing sheets 1 of 14, 2 of 14, 3 of 14, 4 of 14 and 5 of 14 and substitute therefor the drawing sheets, consisting of figs. 1, 2, 3, 4 and 5 as shown on the attached pages.

Signed and Sealed this

Seventh Day of July, 2009

JOHN DOLL
*Acting Director of the United States Patent and Trademark Office*